US011066705B2

(12) United States Patent
Robins et al.

(10) Patent No.: US 11,066,705 B2
(45) Date of Patent: Jul. 20, 2021

(54) CHARACTERIZATION OF ADAPTIVE IMMUNE RESPONSE TO VACCINATION OR INFECTION USING IMMUNE REPERTOIRE SEQUENCING

(71) Applicants: ADAPTIVE BIOTECHNOLOGIES CORPORATION, Seattle, WA (US); FRED HUTCHINSON CANCER RESEARCH CENTER, Seattle, WA (US)

(72) Inventors: Harlan S. Robins, Seattle, WA (US); William Sumner DeWitt, III, Seattle, WA (US); Ryan O. Emerson, Seattle, WA (US)

(73) Assignees: Adaptive Biotechnologies Corporation, Seattle, WA (US); Fred Hutchinson Cancer Research Center, Seattle, WA (US)

( * ) Notice: Subject to any disclaimer, the term of this patent is extended or adjusted under 35 U.S.C. 154(b) by 1062 days.

(21) Appl. No.: 15/529,943

(22) PCT Filed: Nov. 24, 2015

(86) PCT No.: PCT/US2015/062494
§ 371 (c)(1),
(2) Date: May 25, 2017

(87) PCT Pub. No.: WO2016/086029
PCT Pub. Date: Jun. 2, 2016

(65) Prior Publication Data
US 2017/0362653 A1 Dec. 21, 2017

Related U.S. Application Data

(60) Provisional application No. 62/084,470, filed on Nov. 25, 2014.

(51) Int. Cl.
*C12Q 1/6881* (2018.01)
*C12Q 1/6886* (2018.01)
*C12Q 1/6883* (2018.01)

(52) U.S. Cl.
CPC ......... *C12Q 1/6881* (2013.01); *C12Q 1/6883* (2013.01); *C12Q 1/6886* (2013.01); *C12Q 2600/156* (2013.01)

(58) Field of Classification Search
CPC .. C12Q 1/6881; C12Q 1/6886; C12Q 1/6883; C12Q 2600/156
See application file for complete search history.

(56) References Cited

U.S. PATENT DOCUMENTS 5,213,960 A  5/1993 Chang
5,296,351 A  3/1994 Morley
(Continued)

FOREIGN PATENT DOCUMENTS

CN  101225441 A  7/2008
CN  102272327 A  12/2011
(Continued)

OTHER PUBLICATIONS

US 8,642,750 B2, 02/2014, Faham et al. (withdrawn)
(Continued)

*Primary Examiner* — Jeremy C Flinders
(74) *Attorney, Agent, or Firm* — Edward J. Baba; Shweta Chandra; Bozicevic, Field & Francis LLP

(57) ABSTRACT

Methods of monitoring and measuring dynamic adaptive immune cell responses are provided. High-throughput sequencing of T cell receptor and immunoglobulin loci is used to characterize the breadth of an effector cell response to a stimulus, such as a vaccine or infection. Unique responding effector cell clones and abundance thereof can be determined. Additionally, methods for determining the con-
(Continued)

tribution of responding effector cells to the immunological memory compartment are provided.

22 Claims, 13 Drawing Sheets

(56) References Cited

U.S. PATENT DOCUMENTS

| | | |
|---|---|---|
| 5,298,396 A | 3/1994 | Kotzin et al. |
| 5,326,696 A | 7/1994 | Chang |
| 5,336,598 A | 8/1994 | Kotzin et al. |
| 5,418,134 A | 5/1995 | Morley |
| 5,627,037 A | 5/1997 | Ward |
| 5,627,052 A | 5/1997 | Schrader |
| 5,635,354 A | 6/1997 | Kourilsky et al. |
| 5,635,400 A | 6/1997 | Brenner |
| 5,667,967 A | 9/1997 | Steinman et al. |
| 5,741,676 A | 4/1998 | Fuller |
| 5,776,708 A | 7/1998 | Kotzin et al. |
| 5,776,737 A | 7/1998 | Dunn |
| 5,837,447 A | 11/1998 | Gorski |
| 5,846,719 A | 12/1998 | Brenner et al. |
| 5,925,517 A | 7/1999 | Tyagi et al. |
| 5,935,793 A | 8/1999 | Wong |
| 5,981,176 A | 11/1999 | Wallace |
| 6,087,096 A | 7/2000 | Dau et al. |
| 6,091,000 A | 7/2000 | Haynes |
| 6,172,214 B1 | 1/2001 | Brenner |
| 6,258,568 B1 | 7/2001 | Nyren |
| 6,300,070 B1 | 10/2001 | Boles et al. |
| 6,312,690 B1 | 11/2001 | Edelman et al. |
| 6,416,948 B1 | 7/2002 | Pilarski et al. |
| 6,440,706 B1 | 8/2002 | Vogelstein et al. |
| 6,458,530 B1 | 10/2002 | Morris et al. |
| 6,489,103 B1 | 12/2002 | Griffiths et al. |
| 6,524,829 B1 | 2/2003 | Seegar |
| 6,569,627 B2 | 5/2003 | Wittwer et al. |
| 6,596,492 B2 | 7/2003 | Avery et al. |
| 6,753,147 B2 | 6/2004 | Vogelstein et al. |
| 6,787,308 B2 | 9/2004 | Balasubramanian et al. |
| 6,964,850 B2 | 11/2005 | Bevilacqua |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,228 B2 | 1/2007 | Hashmi et al. |
| 7,157,274 B2 | 1/2007 | Bohm et al. |
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,665 B2 | 7/2008 | Brenner |
| 7,432,084 B2 | 10/2008 | Shoemaker |
| 7,537,897 B2 | 5/2009 | Brenner et al. |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer et al. |
| 7,700,323 B2 | 4/2010 | Willis et al. |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | Macevicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham |
| 8,628,927 B2 | 1/2014 | Faham |
| 8,685,678 B2 | 4/2014 | Casbon |
| 8,691,510 B2 | 4/2014 | Faham |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham |
| 8,759,036 B2 | 6/2014 | Wang |
| 8,795,970 B2 | 8/2014 | Faham |
| 8,826,321 B2 | 9/2014 | Cronin et al. |
| 8,835,358 B2 | 9/2014 | Fodor |
| 9,012,148 B2 | 4/2015 | Han et al. |
| 9,043,160 B1 | 5/2015 | Moorhead et al. |
| 9,150,905 B2 | 10/2015 | Robins et al. |
| 9,181,590 B2 | 11/2015 | Robins et al. |
| 9,217,176 B2 | 12/2015 | Faham et al. |
| 9,228,232 B2 | 1/2016 | Faham et al. |
| 9,416,420 B2 | 8/2016 | Faham et al. |
| 9,512,487 B2 | 12/2016 | Faham et al. |
| 9,809,813 B2 | 11/2017 | Robins et al. |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0162197 A1 | 8/2003 | Morley et al. |
| 2003/0207300 A1 | 11/2003 | Matray et al. |
| 2004/0033490 A1 | 2/2004 | Laird et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0214779 A1 | 10/2004 | Ma et al. |
| 2004/0235061 A1 | 11/2004 | Wilkie et al. |
| 2004/0248172 A1 | 12/2004 | Samoszuk et al. |
| 2005/0037356 A1 | 2/2005 | Gullberg et al. |
| 2005/0064421 A1 | 3/2005 | Gehrmann et al. |
| 2005/0142577 A1 | 6/2005 | Jones et al. |
| 2005/0250147 A1 | 11/2005 | Macevicz |
| 2005/0255482 A1 | 11/2005 | Morley et al. |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2006/0263789 A1 | 11/2006 | Kincaid |
| 2007/0020640 A1 | 1/2007 | McCloskey et al. |

(56) References Cited

U.S. PATENT DOCUMENTS

| | | |
|---|---|---|
| 2007/0020670 A1 | 1/2007 | Loken et al. |
| 2007/0105105 A1 | 5/2007 | Clelland et al. |
| 2007/0117134 A1 | 5/2007 | Kou |
| 2007/0160994 A1 | 7/2007 | Lim et al. |
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |
| 2008/0166704 A1 | 7/2008 | Marche et al. |
| 2008/0166718 A1 | 7/2008 | Lim et al. |
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Burczynski et al. |
| 2008/0286777 A1 | 11/2008 | Candeias et al. |
| 2009/0026082 A1 | 1/2009 | Rothberg et al. |
| 2009/0053184 A1 | 2/2009 | Morgan et al. |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |
| 2009/0233301 A1 | 9/2009 | Lee |
| 2009/0253581 A1 | 10/2009 | Van Eijk et al. |
| 2009/0264299 A1 | 10/2009 | Drmanac et al. |
| 2009/0280489 A1 | 11/2009 | Devinder et al. |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021896 A1 | 1/2010 | Han |
| 2010/0021984 A1 | 1/2010 | Edd |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0105886 A1 | 4/2010 | Wondenberg |
| 2010/0137143 A1 | 6/2010 | Rothberg et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0285984 A1 | 11/2010 | Wettstein et al. |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0330571 A1 | 12/2010 | Robins et al. |
| 2011/0003291 A1 | 1/2011 | Pasqual et al. |
| 2011/0014659 A1 | 1/2011 | Balazs et al. |
| 2011/0097712 A1 | 4/2011 | Cantor et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0183863 A1 | 7/2011 | Wagner et al. |
| 2011/0195253 A1 | 8/2011 | Hinz et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0251099 A1 | 10/2011 | Visvanathan et al. |
| 2012/0035062 A1 | 2/2012 | Schultz et al. |
| 2012/0058902 A1 | 3/2012 | Livingston et al. |
| 2012/0071331 A1 | 3/2012 | Casbon et al. |
| 2012/0073667 A1 | 3/2012 | Schultz et al. |
| 2012/0122714 A1 | 5/2012 | Samuels |
| 2012/0135409 A1 | 5/2012 | Faham |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0220466 A1 | 8/2012 | Fire et al. |
| 2013/0005584 A1 | 1/2013 | Faham |
| 2013/0017957 A1 | 1/2013 | Faham et al. |
| 2013/0065768 A1 | 3/2013 | Zheng |
| 2013/0116130 A1 | 5/2013 | Fu |
| 2013/0123120 A1 | 5/2013 | Zimmermann et al. |
| 2013/0136799 A1 | 5/2013 | Faham et al. |
| 2013/0150252 A1 | 6/2013 | Faham |
| 2013/0196328 A1 | 8/2013 | Pepin |
| 2013/0196861 A1 | 8/2013 | Quake |
| 2013/0202718 A1 | 8/2013 | Pepin |
| 2013/0236895 A1 | 9/2013 | Faham |
| 2013/0253842 A1 | 9/2013 | Sherwood et al. |
| 2013/0267427 A1 | 10/2013 | Faham |
| 2013/0288237 A1 | 10/2013 | Robins et al. |
| 2013/0302801 A1 | 11/2013 | Asbury |
| 2013/0324422 A1 | 12/2013 | Faham et al. |
| 2013/0344066 A1 | 12/2013 | Faham |
| 2014/0057799 A1 | 2/2014 | Johnson et al. |
| 2014/0094376 A1 | 4/2014 | Han |
| 2014/0127699 A1 | 5/2014 | Han |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0234835 A1 | 8/2014 | Pepin |
| 2014/0235454 A1 | 8/2014 | Faham |
| 2014/0255929 A1 | 9/2014 | Zheng |
| 2014/0255944 A1 | 9/2014 | Carlton |
| 2014/0256567 A1 | 9/2014 | Robins et al. |
| 2014/0256592 A1 | 9/2014 | Faham |
| 2014/0315725 A1 | 10/2014 | Faham et al. |
| 2014/0322716 A1 | 10/2014 | Robins et al. |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham et al. |
| 2014/0356339 A1 | 12/2014 | Faham et al. |
| 2015/0017652 A1 | 1/2015 | Robins et al. |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham et al. |
| 2015/0051089 A1 | 2/2015 | Robins et al. |
| 2015/0065352 A1 | 3/2015 | Faham et al. |
| 2015/0167080 A1 | 6/2015 | Moorhead et al. |
| 2015/0203897 A1 | 7/2015 | Robins et al. |
| 2015/0218656 A1 | 8/2015 | Kirsch et al. |
| 2015/0247198 A1 | 9/2015 | Klinger et al. |
| 2015/0247201 A1 | 9/2015 | Faham et al. |
| 2015/0252419 A1 | 9/2015 | Moorhead et al. |
| 2015/0252422 A1 | 9/2015 | Faham et al. |
| 2015/0259734 A1 | 9/2015 | Asbury et al. |
| 2015/0299785 A1 | 10/2015 | Livingston et al. |
| 2016/0002731 A1 | 1/2016 | Robins et al. |
| 2016/0115532 A1 | 4/2016 | Faham |
| 2016/0201133 A1 | 7/2016 | Faham et al. |
| 2016/0251721 A1 | 9/2016 | Robins et al. |
| 2016/0251728 A1 | 9/2016 | Faham et al. |
| 2016/0340729 A1 | 11/2016 | Emerson et al. |
| 2017/0335386 A1 | 11/2017 | Livingston et al. |
| 2017/0349954 A1 | 12/2017 | Faham et al. |
| 2018/0030543 A1 | 2/2018 | Robins et al. |
| 2018/0073015 A1 | 3/2018 | Robins et al. |
| 2018/0080090 A1 | 3/2018 | Faham et al. |
| 2018/0112278 A1 | 4/2018 | Faham et al. |

FOREIGN PATENT DOCUMENTS

| | | |
|---|---|---|
| CN | 103097888 A | 5/2013 |
| EP | 0303459 A2 | 2/1989 |
| EP | 0799897 A1 | 10/1997 |

(56) References Cited

FOREIGN PATENT DOCUMENTS

| | | |
|---|---|---|
| EP | 1544308 A1 | 6/2005 |
| EP | 1549764 B1 | 7/2005 |
| EP | 0972081 B1 | 6/2007 |
| EP | 1544308 B1 | 1/2009 |
| EP | 2062982 A1 | 5/2009 |
| EP | 2088432 A1 | 8/2009 |
| EP | 2364368 B1 | 1/2014 |
| JP | 4262799 A | 9/1992 |
| JP | 2002-503954 A | 2/2001 |
| JP | 2005-245381 A | 9/2005 |
| JP | 2006-501842 A | 1/2006 |
| JP | 2007-515955 A | 6/2007 |
| JP | 2007-536939 A | 12/2007 |
| JP | 2008-099588 A | 5/2008 |
| JP | 2012-508011 A | 4/2012 |
| JP | 2013-524848 A | 6/2013 |
| JP | 2013-524849 A | 6/2013 |
| WO | WO 1993/001838 A1 | 2/1993 |
| WO | WO 1995/028481 A1 | 10/1995 |
| WO | WO 1997/013877 A1 | 4/1997 |
| WO | WO 1997/018330 A1 | 5/1997 |
| WO | WO 1997/046706 A1 | 12/1997 |
| WO | WO 1998/001738 A2 | 1/1998 |
| WO | WO 1998/044151 A1 | 10/1998 |
| WO | WO 1999/019717 A1 | 4/1999 |
| WO | WO 1999/020798 A1 | 4/1999 |
| WO | WO 2002/024322 A2 | 3/2002 |
| WO | WO 2003/044225 A2 | 5/2003 |
| WO | WO 2003/052101 A1 | 6/2003 |
| WO | WO 2003/059155 A2 | 7/2003 |
| WO | WO 2004/003820 A2 | 1/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/096985 A2 | 11/2004 |
| WO | WO 2005/005651 A2 | 1/2005 |
| WO | WO 2005/042774 A2 | 5/2005 |
| WO | WO 2005/053603 A2 | 6/2005 |
| WO | WO 2005/056828 A1 | 6/2005 |
| WO | WO 2005/059176 A1 | 6/2005 |
| WO | WO 2005/084134 A2 | 9/2005 |
| WO | WO 2005/111242 A2 | 11/2005 |
| WO | WO 2005/113803 A1 | 12/2005 |
| WO | WO 2006/076025 A2 | 7/2006 |
| WO | WO 2006/076205 A2 | 7/2006 |
| WO | WO 2006/110855 A2 | 10/2006 |
| WO | WO 2006/116155 A2 | 11/2006 |
| WO | WO 2006/138284 A2 | 12/2006 |
| WO | WO 2007/134220 A2 | 11/2007 |
| WO | WO 2008/026927 A2 | 3/2008 |
| WO | WO 2008/039694 A2 | 4/2008 |
| WO | WO 2008/108803 A2 | 9/2008 |
| WO | WO 2008/147879 A1 | 12/2008 |
| WO | WO 2009/015296 A1 | 1/2009 |
| WO | WO 2009/019657 A2 | 2/2009 |
| WO | WO 2009/021215 A1 | 2/2009 |
| WO | WO 2009/045898 A2 | 4/2009 |
| WO | WO 2009/070767 A2 | 6/2009 |
| WO | WO 2009/095567 A2 | 8/2009 |
| WO | WO 2009/108860 A2 | 9/2009 |
| WO | WO 2009/108866 A2 | 9/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |
| WO | WO 2009/158521 A2 | 12/2009 |
| WO | WO 2010/011894 A1 | 1/2010 |
| WO | WO 2010/036352 A1 | 4/2010 |
| WO | WO 2010/053587 A2 | 5/2010 |
| WO | WO 2010/151416 A1 | 12/2010 |
| WO | WO 2011/083296 A1 | 7/2011 |
| WO | WO 2011/083996 A2 | 7/2011 |
| WO | WO 2011/106738 A2 | 9/2011 |
| WO | WO 2011/107595 A1 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2012/027503 A2 | 3/2012 |
| WO | WO 2012/048340 A2 | 4/2012 |
| WO | WO 2012/048341 A1 | 4/2012 |
| WO | WO 2012/055929 A1 | 5/2012 |
| WO | WO 2012/061832 A1 | 5/2012 |
| WO | WO 2012/083069 A2 | 6/2012 |
| WO | WO 2012/083225 A2 | 6/2012 |
| WO | WO 2012/142213 A2 | 10/2012 |
| WO | WO 2012/159754 A2 | 11/2012 |
| WO | WO 2013/033721 A1 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/130512 A2 | 9/2013 |
| WO | WO 2013/131074 A1 | 9/2013 |
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |
| WO | WO 2013/169957 A1 | 11/2013 |
| WO | WO 2013/181428 A2 | 12/2013 |
| WO | WO 2013/188471 A2 | 12/2013 |
| WO | WO 2013/188831 A1 | 12/2013 |
| WO | WO 2014/018460 A1 | 1/2014 |
| WO | WO 2014/026031 A1 | 2/2014 |
| WO | WO 2014/055561 A1 | 4/2014 |
| WO | WO 2014/062945 A1 | 4/2014 |
| WO | WO 2014/062959 A1 | 4/2014 |
| WO | WO 2014/066184 A1 | 5/2014 |
| WO | WO 2014/130685 A1 | 8/2014 |
| WO | WO 2015/002908 A1 | 1/2015 |
| WO | WO 2015/013461 A2 | 1/2015 |
| WO | WO 2015/058159 A1 | 4/2015 |
| WO | WO 2015/106161 A1 | 7/2015 |
| WO | WO 2016/086029 A1 | 6/2016 |

OTHER PUBLICATIONS

Klinger et al. (PLoS, 2013, 8(9):e74231) (Year: 2013).*

Abbott, et al. "Design and use of signature primers to detect carry-over of amplified material", *J Virol Methods*, 46(1):51-59, Abstract Only (1994).

Ahmadzadeh et al. "FOXP3 expression accurately defines the population of intratumoral regulatory T cells that selectively accumulate in metastatic melanoma lesions", *Blood*, 112(13): 4953-4960 (2008).

Akatsuka, Y. et al., "Rapid screening of T-cell receptor (TCR) variable gene usage by multiplex PCR: Application for assessment of clonal composition", *Tissue Antigens*, 53(2):122-134 (1999).

Alatrakchi et al. "T-cell clonal expansion in patients with B-cell lymphoproliferative disorders", *Journal of Immunotherapy*, 21(5):363-370 (1998).

Alexandre, D. et al. "*H. sapiens* rearranged T-cell receptor gamma chain gene, V2-JP1", GenBank accession No. X57737, NCBI, Nov. 14, 2006, 8 pages [online] [retrieved on Jun. 26, 2013] Retrieved from the internet <URL:http://www.ncbi.nlm.nih.gov/nuccore/x57737>.

Alexandre, D. et al. "*H. sapiens* rearranged T-cell receptor gamma chain gene, V3RS-J1 (hybrid joint)", GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.

Altman, et al. "Phenotypic analysis of antigen-specific T lymphocytes", *The Journal of Immunology*, 187(1):7-9 (2011).

(56) References Cited

OTHER PUBLICATIONS

Andreasson, et al. "The human IgE-encoding transcriptome to assess antibody repertoires and repertoire evolution", *J Mol Biol.*, 362(2):212-227 (2006). Epub Aug. 14, 2006.
Armand, P. et al., "Detection of circulating tumour DNA in patients with aggressive B-cell non-Hodgkin lymphoma", *Brit. J. Haematol.*, vol. 163, pp. 123-126 (2013).
Arstila, T.P., et al., "A direct estimate of the human αβ T cell receptor diversity," *Science*, 286(5441): 958-961 (1999).
Aslanzadeh. "Preventing PCR amplification carryover contamination in a clinical laboratory", *Ann Clin Lab Sci.*, 34(4):389-396 (2004).
Assaf, et al. "High Detection Rate of T-Cell Receptor Beta Chain Rearrangements in T-Cell Lymphoproliferations by Family Specific Polymerase Chain Reaction in Combination with the Genescan Technique and DNA Sequencing", *Blood*, 96(2): 640-646 (2000).
Babrzadeh et al. "Development on High-throughput Sequencing Technology: emPCR Titration and Barcode Design", *Stanford School of Medicine*, 2 pages (2011).
Bagnara, et al. "IgV gene intraclonal diversification and clonal evolution in B-cell chronic lymphocytic leukaemia", *British Journal of Haematology*, 133(1):50-58 (2006).
Barker, et al. "A second type II restriction endonuclease from Thermus aquaticus with an unusual sequence specificity", *Nucleic Acids Res.*, 12(14): 5567-5581 (1984).
Baum and McCune et al. "Direct measurement of T-cell receptor repertoire diversity with AmpliCot", *Nat Methods*, 3(11): 895-901 (2006).
Becton-Dickinson, CD marker handbook. bdbiosciences.com/go/mousecdmarkers, p. 1-47 (2010).
Becton-Dickinson T-Cell Research Tools, "Novel multicolor flow cytometry tools for the study of CD4+ T-cell differentiation and plasticity", 16 pages (2009).
Beishuizen, et al. "Analysis of Ig and T-cell receptor genes in 40 childhood acute lymphoblastic leukemias at diagnosis and subsequent relapse: implications for the detection of minimal residual disease by polymerase chain reaction analysis", *Blood*, 83(8):2238-2247 (1994).
Béné and Kaeda, "How and why minimal residual disease studies are necessary in leukemia: a review from WP10 and WP12 of the European LeukaemiaNet", *Haematologica*, 94(8):1135-1150 (2009).
Benichou, J. et al., "Rep-Seq: uncovering the immunological repertoire through next-generation sequencing", *Immunology*, 135(3): 183-191 (2011).
Benichou, J. et al., "The restricted DH gene reading frame usage in the expressed human antibody repertoire is selected based upon its amino acid content", *J Immunol.*, 190(11): 5567-77, 29 pages (2013).
Berger, et al. "The clonotypic T cell receptor is a source of tumor-associated antigens in cutaneous T cell lymphoma", *Annals of the New York Academy of Sciences*, 941:106-122, Abstract Only (2001).
Berget, et al. "Detection of clonality in follicular lymphoma using formalin-fixed, paraffin-embedded tissue samples and BIOMED-2 immunoglobulin primers", J Clin Pathol., 64(1):37-41 (2011). doi: 10.1136/jcp.2010.081109. Epub Oct. 28, 2010.
Bernard et al. "Color multiplexing hybridization probes using the apolipoprotein E locus as a model system for genotyping", Anal Biochem., 273(2):221-228 (1999).
Bernardin, F. et al., "Estimate of the total number of CD8+ clonal expansions in healthy adults using a new DNA heteroduplex-tracking assay for CDR3 repertoire analysis", *Journal of Immunological Methods*, 274(1-2):159-175 (2003).
Bertness, et al. "T-Cell Receptor Gene Rearrangements as Clinical Markers of Human T-Cell Lymphomas", *The New England Journal of Medicine*, 313:534-538 (1985).
Biggerstaff, et al. "Enumeration of leukocyte infiltration in solid tumors by confocal laser scanning microscopy", *BMC Immunol.*, 7:16, 13 pages (2006).

Brochet et al. "IMGT/V-QUEST: the highly customized and integrated system for IG and TR standardized V-J and V-D-J sequence analysis", *Nucleic Acids Research*, vol. 36, Web Server issue W503-W508 (2008).
Bolotin, D.A. et al., "Next generation sequencing for TCR repertoire profiling: Platform-specific features and correction algorithms", *Eur. J. Immunol.*, 42:3073-3083 (2012).
Bonarius, H.P.J. et al. "Monitoring the T-Cell Receptor Repertoire at Single-Clone Resolution", *PLOS One*, 1(e55):1-10 (2006).
Boria, et al. "Primer sets for cloning the human repertoire of T cell receptor variable regions", *BMC Immunology*, 9:50, 9 pages (2008).
Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.
Boudinot et al. "New perspectives for large-scale repertoire analysis of immune receptors", *Molecular Immunology*, 45: 2437-2445 (2008).
Boyce, et al. "Human regulatory T-cell isolation and measurement of function", *BD Biosciences*, pp. 1-20 (2010).
Boyd, S.D. et al., "Individual Variation in the Germline Ig Gene Repertoire Inferred from Variable Region Gene Rearrangements", *The Journal of Immunology*, 184(12): 6986-6992 (2010). Epub 2010.
Boyd, S.D. et al., "Measurement and Clinical Monitoring of Human Lymphocyte Clonality by Massively Parallel V-D-J Pyrosequencing," *Science Translational Medicine*, 1:12ra23, 40 pages, including Supplementary Materials (2009).
Bradfield, et al. "Graft-versus-leukemia effect in acute lymphoblastic leukemia: the importance of tumor burden and early detection", Leukemia, 18(6): 1156-1158 (2004).
Brehm-Stecher and Johnson. "Single-cell microbiology: tools, technologies, and applications", *Microbiology and Molecular Biology Reviews*, 68(3):538-559 (2004).
Brenan, C. et al., "High throughput, nanoliter quantitative PCR," *Drug Discovery Today: Technologies*, 2(3):247-253 (2005).
Brisco, et al. "Determining the repertoire of IGH gene rearrangements to develop molecular markers for minimal residual disease in B-lineage acute lymphoblastic leukemia", *J Mol Diagn.*, 11(3):194-200 (2009).
Brisco, et al. "Outcome prediction in childhood acute lymphoblastic leukaemia by molecular quantification of residual disease at the end of induction", *Lancet*, 343:196-200 (1994).
Brody, et al. "Active and passive immunotherapy for lymphoma: proving principles and improving results", J Clin Oncol., 29(14):1864-1875, Abstract Only (2011). doi: 10.1200/JCO.2010.33.4623. Epub Apr. 11, 2011.
Brody, et al., "Immunotransplant for mantle cell lymphoma: Phase I/II study preliminary results", *Journal of Clinical Oncology*, ASCO Annual Meeting Abstracts Part 1, Suppl; abstr 2509: vol. 29, No. 15, 1 page (2011).
Brüggemann, et al. "Clinical significance of minimal residual disease quantification in adult patients with standard-risk acute lymphoblastic leukemia", *Blood*, 107(3):1116-1123 (2006). Epub Sep. 29, 2005.
Brüggemann, et al. "Rearranged T-cell receptor beta genes represent powerful targets for quantification of minimal residual disease in childhood and adult T-cell acute lymphoblastic leukemia", *Leukemia*, 18(4): 709-719 (2004).
Brüggemann, et al. "Standardized MRD quantification in European ALL trials: proceedings of the Second International Symposium on MRD assessment in Kiel, Germany, Sep. 18-20, 2008", *Leukemia*, 24(3):521-535 (2010). doi: 10.1038/leu.2009.268. Epub Dec. 24, 2009.
Buccisano, et al. "Prognostic and therapeutic implications of minimal residual disease detection in acute myeloid leukemia", Blood, 119(2):332-341 (2012). doi: 10.1182/blood-2011-08-363291. Epub Oct. 28, 2011.
Buccisano, et al. "Monitoring of minimal residual disease in acute myeloid leukemia", Curr Opin Oncol., 21(6):582-588, Abstract Only (2009). doi: 10.1097/CCO.0b013e3283311856.

(56) References Cited

OTHER PUBLICATIONS

Butkus, B. "Hutch Team Uses ddPCR to Quantify T-Cell Response in Tumors; Adaptive Biotech Eyes Market", *PCR Insider*, Dec. 12, 2013, 3 pages http://www.genomeweb.com/print/1323296.
Bystrykh. "Generalized DNA Barcode Design Based on Hamming Codes", *PLoS ONE*, 7(5): e36852, 1-8 (2012).
Campana. "Minimal residual disease in acute lymphoblastic leukemia", *Semin Hematol.*,46(1):100-106 (2009).
Campana, et al. "Role of minimal residual disease monitoring in adult and pediatric acute lymphoblastic leukemia", *Hematol Oncol Clin North Am.*, 23(5): 1083-1098 (2009). doi: 10.1016/j.hoc.2009.07.010.
Campbell et al. "Subclonal phylogenetic structures in cancer revealed by ultra-deep sequencing," *PNAS*, 105(35):13081-13086 (2008).
Caporaso, J.G. et al. "Global patterns of 16S rRNA diversity at a depth of millions of sequences per sample", *PNAS*, 108(Suppl. 1):4516-4522 (2010).
Carlotti, et al. "Transformation of follicular lymphoma to diffuse large B-cell lymphoma may occur by divergent evolution from a common progenitor cell or by direct evolution from the follicular lymphoma clone", *Blood*, 113(15): 3553-3557 (2009). doi: 10.1182/blood-2008-08-174839. Epub Feb. 6, 2009.
Carlson et al. "Profiling the repertoire of TCRB usage in induced and natural Treg cells", *The Journal of Immunology*, 186: 62.5, Abstract (2011).
Carlson, et al. "Deep sequencing of the human TCRγ and TCRβ repertoires provides evidence that TCRβ rearranges after αβ, γδT cell commitment". Presented at the ASHG 2011 Conference. Oct. 2011. Poster. 1 page.
Carlson, C.S. et al. "Using synthetic templates to design an unbiased multiplex PCR assay", *Nature Communications*, 4:2680, pp. 1-9 (2013).
Casali, et al. "Human monoclonals from antigen-specific selection of B lymphocytes and transformation by EBV", *Science*, 234(4775): 476-479, Abstract Only (1986).
Casbon et al. "A method for counting PCR template molecules with application to next-generation sequencing", *Nucleic Acids Research*, 39(12): e81, 8 pages (2011).
Catherwood, M.A. et al., "Improved clonality assessment in germinal centre/post germinal centre non-Hodgkin's lymphomas with high rates of somatic hypermutation", *J. Clin. Pathol.*, 60:524-528, Abstract (2007).
Chan et al. "Evaluation of Nanofluidics Technology for High-Throughput SNP Genotyping in a Clinical Setting", *The Journal of Molecular Diagnostics*, 13(3): 305-312 (2011).
Chen et al. "A novel approach for the analysis of T-cell reconstitution by using a T-cell receptor β-based oligonucleotide microarray in hematopoietic stem cell transplantation", *Exp Hematol.*, 35(5):831-841 (2007).
Chen, et al. "Microfluidic cell sorter with integrated piezoelectric actuator", *Biomed Microdevices*, 11(6): 1223-1231 (2009). doi: 10.1007/s10544-009-9341-5.
Chen, Y. et al., "T-cell receptor gene expression in tumour-infiltrating lymphocytes and peripheral blood lymphocytes of patients with nasopharyngeal carcinoma", *British Journal of Cancer*, 72(1): 117-22 (1995).
Chinese Patent Application No. 2013800628866, English translation of Search Report dated Apr. 11, 2017, 2 pages.
Chinese Patent Application No. 2014800254909, Search Report and English translation, dated May 25, 2017, mailed by the Chinese Patent Office dated Jun. 6, 2017, 5 pages.
Chiu, et al. "Non-invasive prenatal assessment of trisomy 21 by multiplexed maternal plasma DNA sequencing: large scale validity study", *BMJ*, 342:c7401, 9 pages (2011). doi: 10.1136/bmj.c7401.
Choi, et al. "Relapse in children with acute lymphoblastic leukemia involving selection of a preexisting drug-resistant subclone", *Blood*, 110(2):632-639 (2007).
Choi, et al. "Clonal evolution in B-lineage acute lymphoblastic leukemia by contemporaneous $V_H$-$V_H$ gene replacements and $V_H$-$DJ_H$ gene rearrangements", *Blood*, 87(6):2506-2512 (1996).
Chothia, C. et al. "Canonical structures for the hypervariable regions of immunoglobulins," *J. Mol. Biol.*, 196:901-917, Abstract only (1987).
Chothia, C. et al. "Conformations of immunoglobulin hypervariable regions," *Nature*, 342:877-883 (1989).
Churchill and Waterman. "The Accuracy of DNA Sequences: Estimating Sequence Quality", *Genomics*, 14:89-98 (1992).
Chute, et al. "Detection of immunoglobulin heavy chain gene rearrangements in classic Hodgkin lymphoma using commercially available BIOMED-2 primers", *Diagn Mol Pathol.*, 17(2): 65-72 (2008). doi: 10.1097/PDM.0b013e318150d695.
Citri et al. "Comprehensive qPCR profiling of gene expression in single neuronal cells", *Nature Protocols*, 7(1): 118-127 (2012).
Cleary, et al. "Production of complex nucleic acid libraries using highly parallel in situ oligonucleotide synthesis", *Nat Methods*, 1(3): 241-248 (2004). Epub Nov. 18, 2004.
Clemente, et al. "Deep sequencing of the T-cell receptor repertoire in CD8+ T-large granular lymphocyte leukemia identifies signature landscapes", Blood, 122(25): 4077-85 (2013). doi: 10.1182/blood-2013-05-506386. Epub Oct. 22, 2013.
Craig et al. "Identification of genetic variants using bar-coded multiplex sequencing", *Nature Methods*, 5(10): 887-893 (2008) and Supplemental Materials.
Cronin, et al. "Comprehensive next-generation cancer genome sequencing in the era of targeted therapy and personalized oncology", *Biomark Med.*, 5(3):293-305 (2011). (Abstract only). doi: 10.2217/bmm.11.37.
Cronn et al. "Multiplex sequencing of plant chloroplast genomes using Solexa sequencing-by-synthesis technology", *Nucleic Acids Research*, 36(19):e122, 1-11 (2008).
Curran et al. "Nucleotide sequencing of psoriatic arthritis tissue before and during methotrexate administration reveals a complex inflammatory T cell infiltrate with very few clones exhibiting features that suggest they drive the inflammatory process by recognizing autoantigens", *The Journal of Immunology*, 172:1935-1944 (2004).
Curran-Everett, D., "Multiple comparisons: philosophies and illustrations", *Am J Physiol Regulatory Integrative Comp Physiol.*, 279:R1-R8 (2000).
Currier and Robinson. "Spectratype/immunoscope analysis of the expressed TCR repertoire", *Current Protocols in Immunology*, Supplement 38:10.28.1-10.28.24 (2000).
Davi, et al. "Lymphocytic progenitor cell origin and clonal evolution of human B-lineage acute lymphoblastic leukemia", *Blood*, 88(2):609-621 (1996).
Davis, et al. "Interrogating the repertoire: broadening the scope of peptide-MHC multimer analysis", *Nat Rev Immunol.*, 11(8):551-558 (2011). doi: 10.1038/nri3020.
Davis, et al. "Staining of cell surface human CD4 with 2'-F-pyrimidine-containing RNA aptamers for flow cytometry", *Nucleic Acids Research*, 26(17):3915-3924 (1998).
Dean, et al. "Rapid amplification of plasmid and phage DNA using Phi 29 DNA polymerase and multiply-primed rolling circle amplification", *Genome Res.*, 11(6): 1095-1099 (2001).
Dedhia, et al. "Evaluation of DNA extraction methods and real time PCR optimization on formalin-fixed paraffin-embedded tissues", *Asian Pac J Cancer Prev.*, 8(1): 55-59 (2007).
DeKosky et al. "High-throughput sequencing of the paired human immunoglobulin heavy and light chain repertoire", *Nature Biotechnology*, 31(2): 166-169 (2013).
Deng et al. "Gene profiling involved in immature CD4+ T lymphocyte responsible for systemic lupus erythematosus", *Molecular Immunology*, 43:1497-1507 (2006).
Denkert, Carsten, et al. "Tumor-Associated Lymphocytes as an Independent Predictor of Response to Neoadjuvant Chemotherapy in Breast Cancer." Journal of Clinical Oncology (2009); 28(1): 105-113.
Deschoolmeester, et al. "Tumor infiltrating lymphocytes: an intriguing player in the survival of colorectal cancer patients", *BMC Immunology*, 11:19, 12 pages (2010). doi: 10.1186/1471-2172-11-19.
Desmarais, et al. High-throughput sequencing of memory and naïve T cell receptor repertoires at the RNA and DNA levels reveals

(56) References Cited

OTHER PUBLICATIONS differences in relative expression of expanded TCR clones. Adaptive Technologies. Seattle W A. Poster, 1 page. Presented May 5, 2012.

Desmarais and Robins. "High-throughput sequencing of memory and naïve T cell receptor repertoires at the RNA and DNA levels reveals differences in relative expression of expanded TCR clones", The Journal of Immunology, 182: 178.12 (2012).

Dictor et al. "Resolving T-cell receptor clonality in two and genotype in four multiplex polymerase chain reactions", *Haematologica*, 90(11): 1524-1532 (2005).

Diederichsen, et al. "Prognostic value of the CD4+/CD8+ ratio of tumour infiltrating lymphocytes in colorectal cancer and HLA-DR expression on tumour cells", *Cancer Immunol Immunother.*, 52(7):423-428 (2003). Epub Apr. 15, 2003.

Diehl, et al. "BEAMing: single-molecule PCR on microparticles in water-in-oil emulsions", *Nat Methods*, 3(7):551-559, Abstract Only (2006).

Ding, et al. "Clonal evolution in relapsed acute myeloid leukaemia revealed by whole-genome sequencing", *Nature*, 481(7382):506-510 (2012). doi: 10.1038/nature10738.

Diviacco, et al. "A novel procedure for quantitative polymerase chain reaction by coamplification of competitive templates", *Gene*, 122(2):313-320 (1992).

Dobosy, J. et al. "RNase H-dependent PCR (rhPCR): improved specificity and single nucleotide polymorphism detection using blocked cleavable primers", *BMC Biotechnology*, 11(80):1-18 (2011).

Dohm, et al. "Substantial biases in ultra-short read data sets from high throughput DNA sequencing", *Nucleic Acids Research*, 36:e105, 10 pages (2008).

Dou, et al. "Analysis of T cell receptor $V_\beta$ gene usage during the course of disease in patients with chronic hepatitis B", *Journal of Biomedical Science*, 5(6):428-434 (1998).

Dressman, et al. "Transforming single DNA molecules into fluorescent magnetic particles for detection and enumeration of genetic variations", PNAS, 100(15):8817-8822 (2003). Epub Jul. 11, 2003.

Drmanac, et al. "Human genome sequencing using unchained base reads on self-assembling DNA nanoarrays", *Science*, 327(5961):78-81 (2010). doi: 10.1126/science.1181498. Epub Nov. 5, 2009.

Droege, et al. "The Genome Sequencer FLX System—longer reads, more applications, straight forward bioinformatics and more complete data sets", *J Biotechnol.*, 136(1-2):3-10 (2008). doi: 10.1016/j.jbiotec.2008.03.021. Epub Jun. 21, 2008.

Droese, J., et al. "Validation of BIOMED-2 multiplex PCR tubes for detection of TCRB gene rearrangements in T-cell malignancies," *Leukemia*, 18:1531-1538 (2004).

Du et al. "TCR spectratyping revealed T lymphocytes associated with graft-versus-host disease after allogeneic hematopoietic stem cell transplantation", *Leukemia & Lymphoma*, 48(8):1618-1627 (2007).

Dunn, et al. "Focus on TILs: Prognostic significance of tumor infiltrating lymphocytes in human glioma", *Cancer Immun.*, 7:12, 16 pages (2007).

Dziubianau, M., et al., "TCR repertoire analysis by next generation sequencing allows complex differential diagnosis of T cell-related pathology." Am J Transplant (2013); 13(11): 2842-2854. doi: 10.1111/ajt.12431. Epub Sep. 10, 2013.

Eason et al. "Characterization of synthetic DNA bar codes in *Saccharomyces cerevisiae* gene-deletion strains," PNAS, 101(30): 11046-11051 (2004).

Edd et al. "Controlled encapsulation of single cells into monodisperse picoliter drops", *Lab Chip*, 8(8):1262-1264 (2008).

Eichler, et al. "Haplotype and interspersion analysis of the FMR1 CGG repeat identifies two different mutational pathways for the origin of the fragile X syndrome", *Hum Mol Genet.*, 5(3):319-330 (1996).

Eichler, et al. "Length of uninterrupted CGG repeats determines instability in the FMR1 gene", *Nat Genet.*, 8(1):88-94, Abstract Only (1994).

Eid et al. "Real-time DNA sequencing from single polymerase molecules", *Science*, 323(5910):133-138 (2009). doi: 10.1126/science.1162986. Epub Nov. 20, 2008.

Eis, et al. "An invasive cleavage assay for direct quantitation of specific RNAs", *Nat Biotechnol.*, 19(7):673-676, Abstract Only (2001).

Eisenstein. "Personalized, sequencing-based immune profiling spurs startups", Nat Biotechnol., 31(3):184-186 (2013). doi: 10.1038/nbt0313-184b.

Elkord et al. "T regulatory cells in cancer: recent advances and therapeutic potential", *Expert Opinion on Biological Therapy*, 10(11): 1573-1586 (2010).

Emerson, et al. "Correlation of TCR diversity with immune reconstitution after cord blood transplant", Presented at the American Society of Clinical Oncology's annual meeting. May, 2012. Poster. 1 page.

Emerson et al. "Defining the Alloreactive T Cell Repertoire Using High-Throughput Sequencing of Mixed Lymphocyte Reaction Culture", *PLoS One*, 9(11): e111943 (2014).

Emerson, R.O. et al. "High-throughput sequencing of T-cell receptors reveals a homogeneous repertoire of tumour-infiltrating lymphocytes in ovarian cancer", *Journal of Pathology*, 231: 433-440 (2013).

Emerson, et al. "CD4+ and CD8+ T cell β antigen receptors have different and predictable V and J gene usage and CDR3 lengths", Presented at the Annual Meeting of the American Association of Immunologists 2012 in Boston, MA May, 2012. Poster.

Emerson, et al. "Estimating the ratio of CD4+ to CD8+ T cells using high-throughput sequence data", J Immunol Methods, 391(1-2):14-21 (2013). doi: 10.1016/j.jim.2013.02.002. Epub Feb. 18, 2013.

Estorninho, et al. "A novel approach to tracking antigen-experienced CD4 T cells into functional compartments via tandem deep and shallow TCR clonotyping", J Immunol., 191(11): 5430-5440 (2013). doi: 10.4049/jimmunol.I300622. Epub Oct. 25, 2013.

European Application No. 09764927.1, Notice of Opposition dated Oct. 14, 2014, Reference# 547-7.

European Application No. 09764927.1, Notice of Opposition dated Oct. 14, 2014, Reference# BR0-0001EP.

European Application No. 09764927.1, European Opposition dated Oct. 15, 2014 (in French only).

Esendagli et al. "Malignant and non-malignant lung tissue areas are differentially populated by natural killer cells and regulatory T cells in non-small cell lung cancer", *Lung Cancer*, 59(1): 32-40 (2008).

European Patent Application No. 13195379.6, European Search Report and Opinion dated Mar. 13, 2014, 6 pages.

European Patent Application No. 11777704.5, European Search Report dated Jul. 26, 2013, 6 pages.

European Patent Application No. 16183402.3, Extended European Search Report dated Feb. 21, 2017, 8 pages.

European Patent Application No. 12854963.1, Extended European Search Report dated Jun. 10, 2015, 5 pages.

European Patent Application No. 15735285.7, Extended European Search Report dated Jul. 19, 2017, 7 pages.

European Patent Application No. 09764927.1, EPO's Communication of Notices of Opposition, dated Nov. 21, 2014.

European Patent Application No. 09764927.1, Patentee's Observations/Response dated May 27, 2015.

European Patent Application No. 09764927.1, Opponent's Response to Submission of the Patentee dated Nov. 23, 2015.

Faham, M. et al. "Deep-sequencing approach for minimal residual disease detection in acute lymphoblastic leukemia", *Blood*, 120(26): 5173-5180 (2012).

Ferradini et al. "Analysis of T Cell Receptor Variability in Tumor-infiltrating Lymphocytes from a Human Regressive Melanoma", *J. Clin. Invest.*, pp. 1183-1190 (1993).

Ferrero, et al. "Multiple myeloma shows no intra-disease clustering of immunoglobulin heavy chain genes", *Haematologica*, 97(6): 849-853 (2012). doi: 10.3324/haematol.2011.052852. Epub Dec. 29, 2011.

Flaherty et al. "Ultrasensitive detection of rare mutations using next-generation targeted resequencing", *Nucleic Acids Research*, 40(1): e2, 12 pages (2012).

(56) References Cited

OTHER PUBLICATIONS

Flohr, T., et al. "Minimal residual disease-directed risk stratification using real-time quantitative PCT analysis of immunoglobulin and T-cell receptor gene rearrangements in the international multicenter trial AIEOP-BFM ALL 2000 for childhood acute lymphoblastic leukemia", *Leukemia*, 22:771-782 (2008).

Frank. "BARCRAWL and BARTAB: software tools for the design and implementation of barcoded primers for highly multiplexed DNA sequencing," *BMC Bioinformatics*, 10: 362 (2009).

Frederiksson et al., "Multiplex amplification of all coding sequences within 10 cancer genes by Gene-Collector", Nucleic Acids Research, 35(7): e47 (2007).

Freeman, et al. "Quantitative RT-PCR: Pitfalls and Potential", *Biotechniques*, 6(1): 112-125 (1999).

Freeman, J.D., et al. "Profiling the T-Cell Receptor Beta-Chain Repertoire by Massively Parallel Sequencing", *Genome Research*, 19(10):1817-1824 (2009). Epub Jun. 18, 2009.

Fridman, et al. "Prognostic and predictive impact of intra- and peritumoral immune infiltrates", *Cancer Research*, 71(17): 5601-5605 (2011). doi: 10.1158/0008-5472.CAN-11-1316. Epub Aug. 16, 2011.

Fritz et al. "Alterations in the spinal cord T cell repertoire during relapsing experimental autoimmune encephalomyelitis," *J Immunol*, 164:6662-6668 (2000).

Fu et al. "Counting individual DNA molecules by the stochastic attachment of diverse labels", *PNAS*, 108(22): 9026-9031 and Supporting Materials, 8 pages (2011).

Fuller, et al. "The challenges of sequencing by synthesis", *Nat Biotechnol.*, 7(11): 1013-1023 (2009) (Abstract only). doi: 10.1038/nbt.1585. Epub Nov. 6, 2009.

García-Castillo and Núñez, et al. "Detection of clonal immunoglobulin and T-cell receptor gene recombination in hematological malignancies: monitoring minimal residual disease", *Cardiovascular & Haematological Disorders-Drug Targets*, 9:124-135 (2009).

Gauss, et al. "Mechanistic constraints on diversity in human V(D)J recombination", *Mol Cell Biol.*, 16(1):258-269 (1996).

Gawad, et al. "Massive evolution of the immunoglobulin heavy chain locus in children with B precursor acute lymphoblastic leukemia", *Blood*, 120(22):4407-4417 (2012). doi: 10.1182/blood-2012-05-429811. Epub Aug. 28, 2012.

Gerlinger and Swanton. "How Darwinian models inform therapeutic failure initiated by clonal heterogeneity in cancer medicine", *British Journal of Cancer*, 103(8):1139-1143 (2010). doi: 10.1038/sj.bjc.6605912. Epub Sep. 28, 2010.

Gerlinger, M. et al. "Ultra deep T cell receptor sequencing reveals the complexity and intratumour heterogeneity of T cell clones in renal cell carcinomas", *Journal of Pathology*, 231:424-432 (2013).

Germano, et al. "Clonality profile in relapsed precursor-B-ALL children by GeneScan and sequencing analyses. Consequences on minimal residual disease monitoring", *Leukemia*, 17(8):1573-1582 (2003).

Giannoni, et al. Allelic exclusion and peripheral reconstitution by TCR transgenic T cells arising from transduced human hematopoietic stem/progenitor cells, Mol Ther., 21(5):1044-1054 (2013). doi: 10.1038/mt.2013.8. Epub Feb. 5, 2013.

Gilbert, et al. "The isolation of nucleic acids from fixed, paraffin-embedded tissues—which methods are useful when?", *PLoS One*, 2(6):e537, 12 pages (2007).

Giuggio, et al. "Evolution of the intrahepatic T cell repertoire during chronic hepatitis C virus infection", *Viral Immunology*, 18(1):179-189 (2005).

Gloor et al. "Microbiome profiling by Illumina sequencing of combinatorial sequence-tagged PCR products," *PLoS ONE*, 5(10): e15406, 15 pages (2010).

Godelaine, et al. "Polyclonal CTL responses observed in melanoma patients vaccinated with dendritic cells pulsed with a MAGE-3.A1 peptide", *J Immunol.*, 171(9):4893-4897 (2003).

Golembowski, et al. "Clonal evolution in a primary cutaneous follicle center B cell lymphoma revealed by single cell analysis in sequential biopsies", *Immunobiology*, 201(5):631-644 (2000).

Gonzalez, et al. "Incomplete DJH rearrangements of the IgH gene are frequent in multiple myeloma patients: immunobiological characteristics and clinical implications", *Leukemia*, 17:1398-1403 (2003).

Gonzalez et al., "Incomplete DJH rearrangements as a novel tumor target for minimal residual disease quantitation in multiple myeloma using real-time PCR", *Leukemia*, 17:1051-1057 (2003).

Gonzalez, S.F., et al. "Trafficking of B Cell Antigen in Lymph Nodes", *Ann. Rev. Immunol.*, 29: 215-233 (2011).

Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.

Gorski, et al. "Circulating T cell repertoire complexity in normal individuals and bone marrow recipients analyzed by CDR3 size spectratyping. Correlation with immune status", *J Immunol.*, 152(10):5109-5119 (1994).

Gottenberg, et al. "Markers of B-lymphocyte activation are elevated in patients with early rheumatoid arthritis and correlated with disease activity in the ESPOIR cohort", *Arthritis Res Ther.*, 11(4): R114 (2009). doi: 10.1186/ar2773. Epub Jul. 23, 2009.

Gratama and Kern. "Flow cytometric enumeration of antigen-specific T lymphocytes", *Cytometry A*, 58(1): 79-86 (2004).

Gratama, et al. "Measuring antigen-specific immune responses", 2008 update. *Cytometry A.*, 73(11): 971-974 (2008). doi: 10.1002/cyto.a.20655.

Green, et al. "Clonal diversity of Ig and T-cell-receptor gene rearrangements identifies a subset of childhood B-precursor acute lymphoblastic leukemia with increased risk of relapse", *Blood*, 92(3):952-958 (1998).

Greenberg, et al. "Profile of immunoglobulin heavy chain variable gene repertoires and highly selective detection of malignant clonotypes in acute lymphoblastic leukemia" J Leukoc Biol., 57(6):856-864 (1995).

Greenman, et al. "Patterns of somatic mutation in human cancer genomes", *Nature*, 446(7132): 153-158 (2007).

Grupp, et al. "Chimeric antigen receptor-modified T cells for acute lymphoid leukemia", N Engl J Med., 368(16):1509-1518 (2013). doi: 10.1056/NEJMoa1215134. Epub Mar. 25, 2013.

Gulliksen, et al. "Real-time nucleic acid sequence-based amplification in nanoliter volumes", *Anal Chem.*, 76(1): 9-14, Abstract Only (2004).

Gunderson et al. "Decoding Randomly Ordered DNA Arrays", *Genome Research*, 14: 870-877 (2004).

Guo, et al. "Sequence changes at the V-D junction of the $V_H1$ heavy chain of anti-phosphocholine antibodies alter binding to and protection against *Streptococcus pneumoniae*", Int Immunol., 9(5):665-677 (1997).

Gurrieri, et al. "Chronic lymphocytic leukemia B cells can undergo somatic hypermutation and intraclonal immunoglobulin $V_HDJ_H$ gene diversification", *J Exp Med.*, 196(5):629-639 (2002).

Hadrup, et al. "Parallel detection of antigen-specific T-cell responses by multidimensional encoding of MHC multimers", *Nat Methods*, 6(7): 520-526 (2009) (Abstract Only). doi: 10.1038/nmeth.1345. Epub Jun. 21, 2009.

Halldórsdóttir, et al. "Application of BIOMED-2 clonality assays to formalin-fixed paraffin embedded follicular lymphoma specimens: superior performance of the IGK assays compared to IGH for suboptimal specimens", *Leukemia & Lymphoma*, 48(7): 1338-1343 (2007).

Hamady, et al. "Error-correcting barcoded primers for pyrosequencing hundreds of samples in multiplex", *Nature Methods*, 5(3):235-237 (2008). doi: 10.1038/nmeth.1184. Epub Feb. 10, 2008.

Han et al. "Immunorepertoire analysis by multiplex PCR amplification and high throughput sequencing", *The Journal of Immunology*, 182:42.6, 1 page (2009).

Hanahan, et al. "Hallmarks of cancer: the next generation", *Cell*, 144(5): 646-674 (2011). doi: 10.1016/j.cell.2011.02.013.

Harismendy et al. "Evaluation of next generation sequencing platforms for population targeted sequencing studies", *Genome Biology*, 10:R32, 13 pages (2009).

Hawkins, et al. "Whole genome amplification—applications and advances", *Curr Opin Biotechnol.*, 13(1): 65-67 (2002).

(56) References Cited

OTHER PUBLICATIONS

He, et al. "IgH gene rearrangements as plasma biomarkers in Non-Hodgkin's lymphoma patients", *Oncotarget*, 2(3): 178-185 (2011).
Heger, M. "Studies Highlight Challenges of Immune Repertoire Sequencing's Clinical Applicability", available at http://www.genomeweb.com/sequencing/studies-highlight-challenges-immune-repertoire-sequencings-clinical-applicabilit?hq_e=el&hq_m=966798&hq_l=10&hq_v=2357e2f0b3. Accessed Apr. 6, 2011.
Henegariu, O. et al., "Multiplex PCR: Critical Parameters and Step-By-Step Protocol," Biotechniques, Informa HealthCare, 23(3):504-511 (1997).
Hensel et al. "Simultaneous identification of bacterial virulence genes by negative selection", *Science*, 269(5222): 400-403 (1995).
Hill, et al. "Using ecological diversity measures with bacterial communities", *FEMS Microbiol Ecol.*, 43(1):1-11 (2003). doi: 10.1111/j.1574-6941.2003.tb01040.x.
Hirohata, et al. "Regulation of human B cell function by sulfasalazine and its metabolites", *Int Immunopharmacol.*, 2(5): 631-640, Abstract Only (2002).
Hodges, E. et al. "Diagnostic role of tests for T cell receptor (TCR) genes", *J Clin Pathol.*, 56(1): 1-11 (2003).
Holt. "Q &A: BC cancer agency's Robert Holt on sequencing the immune repertoire in immune reconstitution," *Genome Web* (www.genomeweb.com) Jun. 30, 2009.
Holt and Jones. "The new paradigm of flow cell sequencing", *Genome Research*, 18:839-846 (2008).
Hoogenboom, et al. "Multi-subunit proteins on the surface of filamentous phage: methodologies for displaying antibody (Fab) heavy and light chains", *Nucleic Acids Res.*, 19(15): 4133-4137 (1991).
Hoogendoorn, et al. "Primary allogeneic T-cell responses against mantle cell lymphoma antigen-presenting cells for adoptive immunotherapy after stem cell transplantation", *Clin Cancer Res.*, 11(14): 5310-5318 (2005).
Hoos, et al. "Improved endpoints for cancer immunotherapy trials", *J Natl Cancer Inst.*, 102(18): 1388-1397 (2010). doi: 10.1093/jnci/djq310. Epub Sep. 8, 2010.
Hosono, et al. "Unbiased whole-genome amplification directly from clinical samples", *Genome Res.*, 13(5): 954-964 (2003). Epub Apr. 14, 2003.
Hoven, et al. "Detection and isolation of antigen-specific B cells by the fluorescence activated cell sorter (FACS)", *J Immunol Methods*, 117(2): 275-284, Abstract Only, 2 pages (1989).
Howe, et al. "T cell receptor clonotype analysis of T cell responses: Diagnostic application of a clonotypic database", *Blood*, 102:Abstract 3918 (2003).
Huh, et al. "Microfluidics for flow cytometric analysis of cells and particles", *Physiol Meas.*, 26(3): R73-98, Abstract Only (2005). Epub Feb. 1, 2005.
Huijsmans, et al. "Comparative analysis of four methods to extract DNA from paraffin-embedded tissues: effect on downstream molecular applications", *BMC Res Notes*, 3:239, 9 pages (2010). doi: 10.1186/1756-0500-3-239.
Huse, et al. "Generation of a large combinatorial library of the immunoglobulin repertoire in phage lambda", *Science*, 246(4935): 1275-1281, Abstract Only (1989).
Hwang, H.Y. et al. "Identification of a Commonly used CDR3 Region of Infiltrating T Cells Expressing Vβ13 and Vβ15 Derived from Psoriasis Patients", *The Journal of Investigative Dermatology*, 120(3):359-364 (2003).
Iancu, et al. "Profile of a serial killer: cellular and molecular approaches to study individual cytotoxic T-cells following therapeutic vaccination", *J Biomed Biotechnol.*, 2011: 452606 (2011). doi: 10.1155/2011/452606. Epub Nov. 14, 2010.
Illumina. Data Sheet: Sequencing. Genomic Sequencing. Pub. No. 770.2008-016 Reference states: "Current as of Jan. 30, 2009", 6 pages, Copyright 2010.
Illumina. Data Sheet, "TruSeq™ exome enrichment kit", 5 pages (2011).

Illumina Systems & Software, Technology Spotlight, DNA Sequencing with Solexa® Technology, Illumina, Inc., Pub. No. 770-2007-002, 4 pages (2007).
Illumina. "Technical Note: Systems and Software. Calling sequencing SNPs", 3 pages (2010).
Illumina. TruSeq Sample Preparation Kit and Data Sheet. Illumina, Inc., San Diego, CA, 4 pages (2011).
Ishii et al. "Isolation and expression profiling of genes upregulated in the peripheral blood cells of systemic lupus erythematosus patients," *DNA Research*, 12:429-439 (2005).
Jabara et al. "Accurate sampling and deep sequencing of the HIV-1 protease gene using a Primer ID", *PNAS*, 108(50): 20166-20171 (2011).
Jacobi et al. "Activated memory B cell subsets correlate with disease activity in systemic lupus erythematosus: delineation by expression of CD27, IgD, and CD95", *Arthritis & Rheumatism*, 58(6):1762-1773 (2008).
Jacobi et al. "Correlation between circulating $CD27^{high}$ plasma cells and disease activity in patients with systemic lupus erythematosus" *Arthritis & Rheumatism*, 48(5):1332-1342 (2003).
Jaffe, et al. "Classification of lymphoid neoplasms: the microscope as a tool for disease discovery", *Blood*, 112(12): 4384-4399 (2008). doi: 10.1182/blood-2008-07-077982.
Jalla, et al. "Enumeration of lymphocyte subsets using flow cytometry: Effect of storage before and after staining in a developing country setting", *Indian J Clin Biochem.*, 19(2): 95-99 (2004). doi: 10.1007/BF02894264.
Jena, et al. "Amplification of genes, single transcripts and cDNA libraries from one cell and direct sequence analysis of amplified products derived from one molecule", *J. Immunol. Methods*, 190:199-213 (1996).
Jochems and Schlom. "Tumor-infiltrating immune cells and prognosis: the potential link between conventional cancer therapy and immunity", *Exp Biol Med* (Maywood), 236(5): 567-579 (2011). doi: 10.1258/ebm.2011.011007. Epub Apr. 12, 2011.
Jung, et al. "Unraveling V(D)J recombination; insights into gene regulation", *Cell*, 116(2): 299-311 (2004).
Jurkat, Clone 6-1 (ATCC TIB-152) Webpage retrievable from the ATCC under http://www.lgcstandards-atcc.org/Products/All MB-152.aspx#characteristics. Accessed Oct. 14, 2014.
Kanda, et al. "Immune recovery in adult patients after myeloablative dual umbilical cord blood, matched sibling, and matched unrelated donor hematopoietic cell transplantation", Biol Blood Marrow Transplant, 18(11):1664-1676 (2012). doi: 10.1016/j.bbmt.2012.06.005. Epub Jun. 12, 2012.
Kato et al. "Analysis of accumulated T cell clonotypes in patients with systemic lupus erythematosus," *Arthritis & Rheumatism*, 43(12):2712-2721 (2000).
Katz, S.C. et al. "T Cell Infiltrate Predicts Long-Term Survival Following Resection of Colorectal Cancer Liver Metastases," Ann. Surg. Oncol., 16:2524-2530 (2009).
Kedzierska, et al. "Tracking phenotypically and functionally distinct T cell subsets via T cell repertoire diversity", *Mol Immunol.*, 45(3): 607-618 (2008). Epub Aug. 24, 2007.
Kiianitsa, et al., "Development of Tools for T-Cell Repertoire Analysis (TCRB Spectratyping) for the Canine Model of Hematopoietic Cell Transplantation", *Blood*, ASH—Annual Meeting Abstracts, 110:Abstract 4873, 2 pages (2007).
Kim, et al. "An efficient and reliable DNA extraction method for preimplantation genetic diagnosis: a comparison of allele drop out and amplification rates using different single cell lysis methods", *Fertility and Sterility*, 92: 814-818 (2009).
Kim, et al. "Polony multiplex analysis of gene expression (PMAGE) in mouse hypertrophic cardiomyopathy", *Science*, 316(5830):1481-1484 (2007).
Kinde et al. "Detection and quantification of rare mutations with massively parallel sequencing," *PNAS*, 108(23): 9530-9535 and Supporting Information, 16 pages (2011).
Kircher, et al. "Improved base calling for the Illumina Genome Analyzer using machine learning strategies", *Genome Biol.*, 10(8): R83, 9 pages (2009). doi: 10.1186/gb-2009-10-8-r83. Epub Aug. 14, 2009.

(56) References Cited

OTHER PUBLICATIONS

Kirsch, et al. "High-throughput TCR sequencing provides added value in the diagnosis of cutaneous T-cell lymphoma", Presented for the 2014 ASH Annual meeting. Poster. 1 page. Dec. 5-9, 2014.
Kita, et al. "T cell receptor clonotypes in skin lesions from patients with systemic lupus erythematosus", *Journal of Investigative Dermatology*,110(1): 41-46 (1988).
Kivioja et al. "Counting absolute numbers of molecules using unique molecular identifiers," *Nature Methods*, 9(1): 72-76 (2012).
Klarenbeek, P.L. et al. "Human T-cell memory consists mainly of unexpanded clones", *Immunology Letters*, 133: 42-48 (2010).
Klenerman, et al. "Tracking T cells with tetramers: new tales from new tools", *Nat Rev Immunol.*, 2(4):263-272 (2002).
Kneba, M., et al. "Analysis of Rearranged T-cell Receptor β-Chain Genes by Polymerase Chain Reaction (PCR) DNA Sequencing and Automated High Resolution PCR Fragment Analysis",*Blood*, 86:3930-3937 (1995).
Kneba, et al. "Characterization of clone-specific rearrangement T-cell receptor gamma-chain genes in lymphomas and leukemias by the polymerase chain reaction and DNA sequencing",*Blood*, 84(2):574-581 (1994).
Kobari, et al. "T cells accumulating in the inflamed joints of a spontaneous murine model of rheumatoid arthritis become restricted to common clonotypes during disease progression", *Int Immunol.*, 16(1):131-138 (2004).
Koboldt et al., "VarScan: variant detection in massively parallel sequencing of individual and pooled samples", *Bioinformatics*, 25(17): 2283-2285 (2009).
Koch, et al. "Tumor infiltrating T lymphocytes in colorectal cancer: Tumor-selective activation and cytotoxic activity in situ," *Ann Surg.*, 244(6): 986-992; discussion 992-993 (2006).
Kojima et al. "PCR amplification from single DNA molecules on magnetic beads in emulsion: application for high-throughput screening of transcription factor targets", *Nucleic Acids Research*, 33: 17, e150, 9 pages (2005).
Kohlmann, et al. "Integration of next-generation sequencing into clinical practice: are we there yet'?", *Semin Oncol.*, 39(1): 26-36, Abstract Only (2012). doi: 10.1053/j.seminoncol.2011.11.008.
Kotlan, Beatrix, et al. "Immunoglobulin variable regions usage by B-lymphocytes infiltrating a human breast medullary carcinoma." Immunology Letters (1999); 65(3): 143-151.
Krause et al. "Epitope-Specific Human Influenza Antibody Repertoires Diversify by B Cell Intraclonal Sequence Divergence and Interclonal Convergence", *The Journal of Immunology*, 187: 3704-3711 (2011).
Krueger, et al. "Large scale loss of data in low-diversity illumina sequencing libraries can be recovered by deferred cluster calling", *PLoS One*, 6(1): e16607, 7 pages (2011). doi: 10.1371/journal.pone. 0016607.
Ku, et al. "Exome sequencing: dual role as a discovery and diagnostic tool", *Ann Neurol.*, 71(1):5-14, Abstract Only (2012). doi: 10.1002/ana.22647.
Kumar, et al. "PEG-labeled nucleotides and nanopore detection for single molecule DNA sequencing by synthesis", *Sci Rep.*, 2:684, 8 pages (2012). Epub Sep. 21, 2012.
Kwak, et al. "Induction of immune responses in patients with B-cell lymphoma against the surface-immunoglobulin idiotype expressed by their tumors", *N Engl J Med.*, 327(17):1209-1215 (1992).
Kyu et al. "Frequencies of human influenza-specific antibody secreting cells or plasmablasts post vaccination from fresh and frozen peripheral blood mononuclear cells", *Journal of Immunological Methods*, 340: 42-47 (2009).
Ladetto, et al., "Next-generation sequencing and real-time quantitative PCR for minimal residual disease (MRD) detection using the immunoglobulin heavy chain variable region: A methodical comparison in acute lymphoblastic leukemia (ALL), mantle cell lymphoma (MCL) and multiple myeloma (MM)", *Blood*, vol. 120 , No. 21, Abstract 788 (Conference Abstract), Entire Abstract (2012).

Ladetto, M. et al. "Real-time polymerase chain reaction in multiple myeloma: Quantitative analysis of tumor contamination of stem cell harvests", *Experimental Hematology*, 30:529-536 (2002).
Ladetto, M. et al. "Real-Time Polymerase Chain Reaction of Immunoglobulin Rearrangements for Quantitative Evaluation of Minimal Residual Disease in Multiple Myeloma", *American Society for Blood and Marrow Transplantation*, 6(3):241-253 (2000).
Langerak, et al. "Immunoglobulin/T-cell receptor clonality diagnostics", *Expert Opin. Med. Diagn.*, 1(3):451-461 (2007).
Langerak, et al. "Polymerase chain reaction-based clonality testing in tissue samples with reactive lymphoproliferations: usefulness and pitfalls. A report of the BIOMED-2 Concerted Action BMH4-CT98-3936", *Leukemia*, 21(2):222-229 (2007).
Laplaud et al. "Blood T-cell receptor β chain transcriptome in multiple sclerosis. Characterization of the T cells with altered CDR3 length distribution", *Brain*, 127:981-995 (2004).
Laplaud et al. "Serial blood T cell repertoire alterations in multiple sclerosis patients; correlation with clinical and MRI parameters", *Journal of Neuroimmunology*, 177(1-2):151-160 (2006).
Larimore, K., et al. "Shaping of Human Germline IgH Repertoires Revealed by Deep Sequencing", *The Journal of Immunology*, 189(6): 3221-3230 (2012).
Lassmann, et al. "Application of BIOMED-2 primers in fixed and decalcified bone marrow biopsies: analysis of immunoglobulin H receptor rearrangements in B-cell non-Hodgkin's lymphomas", *J Mol Diagn.*, 7(5): 582-591 (2005).
Lee, et al. "Characterization of circulating T cells specific for tumor-associated antigens in melanoma patients", *Nat Med.*, 5(6): 677-685, Abstract Only (1999).
Lee, et al. "Prognostic implications of type and density of tumour-infiltrating lymphocytes in gastric cancer", *Br J Cancer*, 99(10): 1704-1711 (2008). doi: 10.1038/sj.bjc.6604738. Epub Oct. 21, 2008.
Lefranc. "IMGT, the international ImMunoGeneTics database", *Nucleic Acids Res.*, 31(1):307-310 (2003).
Leiden, J.M. et al. "The Complete Primary Structure of the T-Cell Receptor Genes From an Alloreactive Cytotoxic Human T-Lymphocyte Clone", Immunogenetics, 24(1): 17-23 (1986).
Leisner, et al. "One-pot, mix-and-read peptide-MHC tetramers", *PLoS One*, 3(2):e1678, 11 pages (2008). doi: 10.1371/journal.pone. 0001678.
Leone, et al. "Molecular beacon probes combined with amplification by NASBA enable homogeneous, real-time detection of RNA", *Nucleic Acids Research*, 26(9): 2150-2155 (1998).
Leproust, et al. "Synthesis of high-quality libraries of long (150mer) oligonucleotides by a novel depurination controlled process", *Nucleic Acids Res.*, 38(8): 2522-2540 (2010). doi: 10.1093/nar/gkq163. Epub Mar. 22, 2010.
Lessin, et al. "Molecular diagnosis of cutaneous T-cell lymphoma: polymerase chain reaction amplification of T-cell antigen receptor beta-chain gene rearrangements", *J Invest Dermatol.*, 96(3): 299-302 (1991).
Li, et al. "Utilization of Ig heavy chain variable, diversity, and joining gene segments in children with B-lineage acute lymphoblastic leukemia: implications for the mechanisms of VDJ recombination and for pathogenesis", *Blood*, 103(12):4602-4609 (2004).
Li, et al. "An improved one-tube RT-PCR protocol for analyzing single-cell gene expression in individual mammalian cells", *Anal. Bioanal. Chem.*, 397: 1853-1859 (2010).
Li, et al. "β cell-specific CD4+ T cell clonotypes in peripheral blood and the pancreatic islets are distinct", *J Immunol.* , 183(11): 7585-7591 (2009). doi: 10.4049/jimmunol.0901587. Epub Nov. 16, 2009.
Li, et al. "Clonal rearrangements in childhood and adult precursor B acute lymphoblastic leukemia: a comparative polymerase chain reaction study using multiple sets of primers", *Eur J Haematol.*, 63(4):211-218 (1999).
Li, et al. "Detailed clonality analysis of relapsing precursor B acute lymphoblastic leukemia: implications for minimal residual disease detection", *Leukemia Research*, 25:1033-1045 (2001).
Li, et al. "Sequence analysis of clonal immunoglobulin and T-cell receptor gene rearrangements in children with acute lymphoblastic leukemia at diagnosis and at relapse: implications for pathogenesis

(56) References Cited

OTHER PUBLICATIONS and for the clinical utility of PCR-based methods of minimal residual disease detection", *Blood*, 102:4520-4526 (2003).
Liedtke, et al. "A comparison of methods for Rna extraction from lymphocytes for RT-PCR", *PCR Methods and Applications*, 4(3): 185-187 (1994).
Lin, et al. "Multiplex genotype determination at a large number of gene loci", *Proc Natl Acad Sci USA*, 93(6): 2582-2587 (1996).
Liu, et al. "CD127 expression inversely correlates with FoxP3 and suppressive function of human CD4+T reg cells", *J Exp Med.*, 203(7): 1701-1711 (2006). Epub Jul. 3, 2006.
Logan, et al., "High-throughput immunoglobulin gene sequencing quantifies minimal residual disease in CLL with 10e-6 sensitivity and strongly predicts relapse after allogeneic hematopoietic cell transplantation", *Blood*, vol. 118 (21), Abstract 2542 (2011).
Logan, A.C. et al. "High-throughput VDJ sequencing for quantification of minimal residual disease in chronic lymphocytic leukemia and immune reconstitution assessment", *PNAS*, 108(52): 21194-21199 (2011). Epub Dec. 12, 2011.
Logan, et al., "Massively parallel immunoglobulin gene sequencing provides ultra-sensitive minimal residual disease detection and predicts post-transplant relapse in acute lymphoblastic leukemia by three to six months", *Blood*, vol. 118 (21), Abstract 4104 (2011).
Lossos, et al. "Transformation of follicular lymphoma to diffuse large-cell lymphoma: alternative patterns with increased or decreased expression of c-myc and its regulated genes", *PNAS*, 99(13): 8886-8891 (2002). Epub Jun. 19, 2002.
Lovisa, et al. "IGH and IGK gene rearrangements as PCR targets for pediatric Burkitt's lymphoma and mature B-ALL MRD analysis", *Lab Invest.*, 89(10):1182-1186 (2009).
Lowman, et al. "Monovalent phage display: a method for selecting variant proteins from random libraries", *Methods: A Companion to Methods in Enzymology*, 3: 205-216, Abstract Only (1991).
Lúcid, P. et al. "Flow cytometric analysis of normal B cell differentiation: a frame of reference for the detection of minimal residual disease in precursor-B-ALL", *Leukemia*, 13:419-427 (1999).
Lyamichev, et al. "Polymorphism identification and quantitative detection of genomic DNA by invasive cleavage of oligonucleotide probes", *Nat Biotechnol.*, 17(3): 292-396 (1999).
Luo et al. "Analysis of the interindividual conservation of T cell receptor α- and β-chain variable regions gene in the peripheral blood of patients with systemic lupus erythematosus", *Clinical & Experimental Immunology*, 154(3):316-324 (2008).
Mackay, et al. "Real-time PCR in virology", *Nucleic Acids Res.*, 30(6): 1292-1305 (2002).
Malyguine, et al. "ELISPOT Assay for Monitoring Cytotoxic T Lymphocytes (CTL) Activity in Cancer Vaccine Clinical Trials", *Cells*, 1(2): 111-126 (2012). doi: 10.3390/cells1020111.
Manion et al., "Reducing Error in Next Generation Sequencing Data with NextGENe Software's Condensation Tool™", Mar. 2009, pp. 1-3.
Manrao, et al. "Reading DNA at single-nucleotide resolution with a mutant MspA nanopore and phi29 DNA polymerase", *Nat Biotechnol.*, 30(4): 349-353 (2012). doi: 10.1038/nbt.2171.
Mar et al. "Inferring steady state single-cell gene expression distributions from analysis of mesoscopic samples", *Genome Biology*, 7(12): R119, 12 pages (2006).
Mardis. "Next-generation DNA sequencing methods", *Annu. Rev. Genomics Hum. Genet.*, 9:387-402 (2008). doi: 10.1146/annurev.genom.9.081307.164359.
Margulies, et al. "Genome sequencing in microfabricated high-density picolitre reactors", *Nature*, 437(7057):376-380 (2005). Epub Jul. 31, 2005.
Mariani, S. et al., "Comprehensive assessment of the TCRBV repertoire in small T-cell samples by means of an improved and convenient multiplex PCR method," *Experimental Hematology*, 37(6):728-738 (2009).
Markoulatos, P. et al., "Multiplex Polymerase Chain Reaction: A Practical Approach", Journal of Clinical Laboratory Analysis, 16:47-51 (2002).

Martin-Jimenez, et al. "Molecular characterization of heavy chain immunoglobulin gene rearrangements in Waldenström's macroglobulinemia and IgM monoclonal gammopathy of undetermined significance", *Haematologica*, 92(5): 635-642 (2007).
Mary et al. "Analysis of gene expression at the single-cell level using microdroplet-based microfluidic technology", *Biomicrofluidics*, 5: 024109-1-024109-10 (2011).
Maryanski, J.L. et al., "A quantitative, single-cell PCR analysis of an antigen-specific TCR repertoire 8 selected during an in vivo CD8 response: direct evidence for a wide range of clone sizes with uniform tissue distribution", Molecular Immunology, 36:745-753 (1999).
Maślanka, K. et al., "Molecular Analysis of T-Cell Repertoires: Spectratypes Generated by Multiplex Polymerase Chain Reaction and Evaluated by Radioactivity or Fluorescence", *Human Technology*, 44(1):28-34 (1995).
Mato et al. "Correlation of clonal T cell expansion with disease activity in systemic lupus erythematosus", *Int Immunol.*, 9(4):547-554 (1997).
Matolcsy, et al. "Clonal evolution of B cells in transformation from low- to high-grade lymphoma", *Eur. J. Immunol.*,29(4):1253-1264 (1999).
Matsumoto et al. "CDR3 spectratyping analysis of the TCR repertoire in Myasthenia Gravis", *The Journal of Immunology*, 176:5100-5107 (2006).
Matsumoto et al. "Complementarity-determining region 3 spectratyping analysis of the TCR repertoire in multiple sclerosis", *The Journal of Immunology*, 170:4846-4853 (2003).
Mazor et al. "Antibody internalization studied using a novel IgG binding toxin fusion", *Journal of Immunological Methods*, 321: 41-59 (2007).
Mazumder, et al., "Detection of multiple myeloma cells in peripheral blood using high-throughput sequencing assay" *Blood*, vol. 120, No. 21, Abstract 321 (Conference Abstract), Entire Abstract (2012).
McCloskey et al. "Encoding PCR products with batch-stamps and barcodes," *Biochem. Genet.*, 45: 761-767 (2007).
Mei et al. "Blood-borne human plasma cells in steady state are derived from mucosal immune responses", *Blood*, 113(11): 2461-2469 (2009).
Meijer et al. "Isolation of Human Antibody Repertoires with Preservation of the Natural Heavy and Light Chain Pairing", *J. Mol. Biol.*, 358: 764-772 (2006).
Meier, et al. "Fractal organization of the human T cell repertoire in health and after stem cell transplantation", Biol Blood Marrow Transplant., 19(3):366-77 (2013). doi: 10.1016/j.bbmt.2012.12.004. Epub Jan. 11, 2013.
Meier et al. "Simultaneous evaluation of T-cell and B-cell clonality, t(11;14) and t(14;18), in a single reaction by a four-color multiplex polymerase chain reaction assay and automated High-Resolution fragment analysis", *American Journal of Pathology*, 159(6): 2031-2043 (2001).
Meier, et al. "The influence of different stimulation conditions on the assessment of antigen-induced CD154 expression on CD4+T cells", *Cytometry A.*, (11):1035-1042 (2008). doi: 10.1002/cyto.a. 20640.
Meleshko, et al. "Rearrangements of IgH, TCRD and TCRG genes as clonality marker of childhood acute lymphoblastic leukemia", *Experimental Oncology*, 27(4):319-324 (2005).
Menezes et al. "A public T cell clonotype within a heterogeneous autoreactive repertoire is dominant in driving EAE", *J Clin Invest*, 117(8):2176-2185 (2007).
Merriam-Webster, 2 pages, (definition of "e.g.," accessed Apr. 25, 2014).
Merriam-Webster, 4 pages (definition of "substantial," accessed Apr. 25, 2014).
Metzker, "Sequencing Technologies—The Next Generation", *Nature Reviews, Genetics*, 11:31-46 (2010).
Meyer et al. "Targeted high-throughput sequencing of tagged nucleic acid samples", *Nucleic Acids Research*, 35(15): e97, 5 pages (2007).
Miceli and Parnes. "The roles of CD4 and CD8 in T cell activation", *Seminars in Immunology*, 3(3): 133-141 (1991). Abstract only.

(56) References Cited

OTHER PUBLICATIONS

Michálek, et al. "Detection and long-term in vivo monitoring of individual tumor-specific T cell clones in patients with metastatic melanoma", *J Immunol.*, 178(11):6789-6795 (2007).

Michálek, et al. "Identification and monitoring of graft-versus-host specific T-cell clone in stem cell transplantation", *The Lancet*, 361(9364): 1183-1185 (2003).

Miller, et al., "Assembly algorithms for next-generation sequencing data", Genomics, 95(6): 315-327 (2010).

Miltenyi, et al. "High gradient magnetic cell separation with MACS", *Cytometry*, 11(2): 231-238 (1990).

Miner et al. "Molecular barcodes detect redundancy and contamination in hairpin-bisulfite PCR", *Nucleic Acids Research*, 32(17): e135, 4 pages (2004).

Miqueu, P. et al. "Statistical analysis of CDR3 length distributions for the assessment of T and B cell repertoire biases", *Molecular Immunology*, 44:1057-1064 (2007).

Mitra, et al. "Fluorescent in situ sequencing on polymerase colonies", *Anal Biochem.*, 320(1): 55-65, Abstract Only (2003).

Miyashita, et al. "N-Methyl substituted 2',4'—BNANC: a highly nuclease-resistant nucleic acid analogue with high-affinity RNA selective hybridization", *Chem Commun* (Camb), (36): 3765-3767, Abstract Only (2007). Epub Jul. 9, 2007.

Moen, et al. "Immunoglobulin G and A antibody responses to Bacteroides forsyth and Prevotella intermedia in sera and synovial fluids of arthritis patients", *Clin Diagn Lab Immunol.*, 10(6): 1043-1050 (2003).

Molloy, et al. "Soluble T cell receptors: novel immunotherapies", *Curr Opin Pharmacol.*, 5(4): 438-443 (2005) (Abstract Only).

Monod, M.Y. et al. "IMGT/JunctionAnalysis: the first tool for the analysis of the immunoglobulin and T cell receptor complex V-J and V-D-J JUNCTIONs", *Bioinformatics*, 20(Suppl 1):i379-385 (2004).

Moody, et al. "Antigen-specific B cell detection reagents: use and quality control", *Cytometry A.*, 73(11): 1086-1092 (2008). doi: 10.1002/cyto.a.20599.

Morgan, et al. "Cancer regression in patients after transfer of genetically engineered lymphocytes", *Science*, 314(5796): 126-129 (2006). Epub Aug. 31, 2006.

Morozova et al. "Applications of New Sequencing Technologies for Transcriptome Analysis", *Annu. Rev. Genomics Hum. Genet.*, 10: 135-151 (2009).

Morris, H., et al., "Tracking donor-reactive T cells: Evidence for clonal deletion in tolerant kidney transplant patients." Sci Transl Med. (2015); 7(272): 272ra10.

Morrissy et al. "Next-generation tag sequencing for cancer gene expression profiling", *Genome Research*, 19: 1825-1835 (2009).

Moss, et al. "The human T cell receptor in health and disease", *Annu. Rev. Immunol.*, 10:71-96 (1992).

Moura, et al. "Alterations on peripheral blood B-cell subpopulations in very early arthritis patients", *Rheumatology* (Oxford), 49(6): 1082-1092 (2010). doi: 10.1093/rheumatology/keq029. Epub Mar. 7, 2010.

Muraro et al. "Molecular tracking of antigen-specific T cell clones in neurological immune-mediated disorders", *Brain*, 126(Pt 1):20-31 (2003).

Murugan, et al. "Statistical inference of the generation probability of T-cell receptors from sequence repertoires", *PNAS*, 109(40): 16161-16166 (2012). doi: 10.1073/pnas.1212755109. Epub Sep. 17, 2012.

Naito, et al. "CD8+ T cells infiltrated within cancer cell nests as a prognostic factor in human colorectal cancer", *Cancer Research*, 58(16): 3491-3494 (1998).

Nardi, et al. "Quantitative monitoring by polymerase colony assay of known mutations resistant to ABL kinase inhibitors", *Oncogene*, 27(6):775-782 (2008). Epub Aug. 6, 2007, 1-8.

Navarrete, et al. "Upfront immunization with autologous recombinant idiotype Fab fragment without prior cytoreduction in indolent B-cell lymphoma", *Blood*, 117(5): 1483-1491 (2011). doi: 10.1182/blood-2010-06-292342. Epub Nov. 2, 2010.

Neale, et al. "Comparative analysis of flow cytometry and polymerase chain reaction for the detection of minimal residual disease in childhood acute lymphoblastic leukemia", *Leukemia*, 18(5):934-938 (2004).

Needleman and Wunsch. "A general method applicable to the search for similarities in the amino acid sequence of two proteins", *J Mol Biol.*, 48(3): 443-453 (1970).

Nelson. "CD20+ B cells: the other tumor-infiltrating lymphocytes", *The Journal of Immunology*, 185(9): 4977-4982 (2010). doi: 10.4049/jimmunol.1001323.

Newman, et al. "Identification of an antigen-specific B cell population", *J Immunol Methods*, 272(1-2): 177-187, Abstract Only (2003).

Nguyen et al. "Identification of errors introduced during high throughput sequencing of the T cell receptor repertoire" *BMC Genomics*, 12: 106, 13 pages (2011).

Nielsen, et al. "Peptide nucleic acid (PNA). A DNA mimic with a pseudopeptide backbone", *Chem. Soc. Rev.*, 26:73-78, Abstract Only (1997).

Nosho, et al. "Tumour-infiltrating T-cell subsets, molecular changes in colorectal cancer, and prognosis: cohort study and literature review", *J Pathol.*, 222(4): 350-366 (2010). doi: 10.1002/path.2774.

Novak, et al. "Single Cell Multiplex Gene Detection and Sequencing Using Microfluidically-Generated Agarose Emulsions", *Angew Chem Int Ed Engl.*, 50(2): 390-395, with supplemental materials (2011).

Oble, et al. "Focus on TILs: prognostic significance of tumor infiltrating lymphocytes in human melanoma", *Cancer Immunity*, 9: 3, 20 pages (2009).

Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.

Ogle, et al. "Direct measurement of lymphocyte receptor diversity", *Nucleic Acids Research*, 31(22):e139, 6 pages (2003).

Ohtani. "Focus on TILs: prognostic significance of tumor infiltrating lymphocytes in human colorectal cancer", *Cancer Immunity*, 7: 4, 9 pages (2007).

Okajima et al. "Analysis of T cell receptor Vβ diversity in peripheral CD4+ and CD8+ T lymphocytes in patients with autoimmune thyroid diseases", *Clinical & Experimental Immunology*, 155:166-172 (2008).

Okello et al. "Comparison of methods in the recovery of nucleic acids from archival formalin-fixed paraffin-embedded autopsy tissues", *Anal Biochem.*, 400(1): 110-117 (2010). doi: 10.1016/j.ab.2010.01.014. Epub Jan. 15, 2010.

Ottensmeier, et al. "Analysis of VH genes in follicular and diffuse lymphoma shows ongoing somatic mutation and multiple isotype transcripts in early disease with changes during disease progression", *Blood*, 91(11): 4292-4299 (1998).

Packer and Muraro. "Optimized clonotypic analysis of T-cell receptor repertoire in immune reconstitution", *Experimental Hematology*, 35(3):516-521 (2007).

Palmowski, et al. "The use of HLA class I tetramers to design a vaccination strategy for melanoma patients", *Immunol Rev.*, 188: 155-163 (2002) (Abstract Only).

Pan, et al. "A new FACS approach isolates hESC derived endoderm using transcription factors", *PLoS One*, 6(3): e17536, 9 pages (2011). doi: 10.1371/journal.pone.0017536.

Panzer-Grümayer et al. "Immunogenotype changes prevail in relapses of young children with *TEL-AML1*-positive acute lymphoblastic leukemia and derive mainly from clonal selection", *Clin Cancer Research*, 11(21):7720-7727 (2005).

Parameswaran et al. "A pyrosequencing-tailored nucleotide barcode design unveils opportunities for large-scale sample multiplexing", *Nucleic Acids Research*, 35(19): e130, 9 pages (2007).

Parmigiani, et al. "Design and analysis issues in genome-wide somatic mutation studies of cancer", *Genomics*, 93(1): 17-21 (2009). doi: 10.1016/j.ygeno.2008.07.005. Epub Aug. 23, 2008.

Pasqual et al. "Quantitative and qualitative changes in V-J alpha rearrangements during mouse thymocytes differentiation: implication for a limited T cell receptor alpha chain repertoire", *Journal of Experimental Medicine*, 196(9): 1163-1173 (2002). XP002322207 ISSN: 0022-1007.

(56) References Cited

OTHER PUBLICATIONS

Peet. "The Measurement of Species Diversity", *Annual Review of Ecology and Systematics*, 5: 285-307, Abstract Only (1974).
Petrosino, et al. "Metagenomic pyrosequencing and microbial identification", *Clin Chem.*, 55(5): 856-866 (2009). doi: 10.1373/clinchem.2008.107565. Epub Mar. 5, 2009.
PCT/US2009/006053, International Search Report dated Jun. 15, 2010, 6 pages.
PCT/US2009/006053, Written Opinion dated Jun. 15, 2010, 4 pages.
PCT/US2009/006053, International Preliminary Report on Patentability dated May 10, 2011, 5 pages.
PCT/US2010/037477, International Search Report and Written Opinion dated Sep. 24, 2010, 10 pages.
PCT/US2010/037477, International Preliminary Report on Patentability dated Jan. 4, 2012, 7 pages.
PCT/US2011/000791, International Search Report and Written Opinion dated Sep. 22, 2011, 13 pages.
PCT/US2011/000791, International Preliminary Report on Patentability dated Nov. 6, 2012, 10 pages.
PCT/US2011/049012, International Search Report and Written Opinion dated Apr. 10, 2012, 9 pages.
PCT/US2011/049012, International Preliminary Report on Patentability dated Feb. 26, 2013, 5 pages.
PCT/US2015/010904, International Search Report dated May 6, 2015, 4 pages.
PCT/US2015/010904, Written Opinion dated May 6, 2015, 4 pages.
PCT/US2015/010904, International Preliminary Report on Patentability dated Jul. 12, 2016, 14 pages.
PCT/US2012/053530, International Preliminary Report on Patentability dated FMar. 12, 2014, 7 pages.
PCT/US2012/053530, International Search Report and Written Opinion dated Feb. 26, 2013, 13 pages.
PCT/US2012/058989, International Preliminary Report on Patentability dated Apr. 15, 2014, 8 pages.
PCT/US2012/058989, International Search Report and Written Opinion dated Mar. 29, 2013, 12 pages.
PCT/US2012/068631, International Preliminary Report on Patentability dated Jun. 10, 2014, 7 pages.
PCT/US2012/068631, International Search Report and Written Opinion dated Feb. 26, 2013, 8 pages.
PCT/US2012/069187, International Preliminary Report on Patentability dated May 5, 2015, 6 pages.
PCT/US2012/069187, International Search Report and Written Opinion dated Feb. 22, 2013, 8 pages.
PCT/US2013/029181, International Search Report and Written Opinion dated May 31, 2013, 6 pages.
PCT/US2013/029181, International Preliminary Report on Patentability dated Sep. 9, 2014, 5 pages.
PCT/US2013/062925, International Preliminary Report on Patentability dated Apr. 16, 2015, 30 pages.
PCT/US2013/062925, International Search Report and Written Opinion dated Nov. 25, 2013, 11 pages.
PCT/US2013/062925, Second Written Opinion dated Jan. 23, 2015, 7 pages.
PCT/US2014/047909, International Preliminary Report on Patentability dated Jan. 26, 2016.
PCT/US2014/047909, International Search Report dated Nov. 17, 2014.
PCT/US2014/047909, Written Opinion dated Nov. 17, 2014, 9 pages.
PCT/US2015/062494, International Search Report and Written Opinion dated Mar. 31, 2016, 29 pages.
PCT/US2015/062494, International Preliminary Report on Patentability, dated May 30, 2017, 22 pages.
Pekin, D. et al. "Quantitative and sensitive detection of rare mutations using droplet-based microfluidics", *Lab Chip*, 11(3): 2156-2166 (2011).
Pels et al. "Clonal evolution as pathogenetic mechanism in relapse of primary CNS lymphoma", *Neurology*, 63(1):167-169 (2004).
Perkel, J. "Overcoming the Challenges of Multiplex PCR", *Biocompare Editorial Article*, Oct. 23, 2012, 6 Pages, can be retrieved at URL:http://www.biocompare.com/Editorial-Articles/117895-Multiplex-PCR/>.
Pira et al. "Human naive CD4 T-cell clones specific for HIV envelope persist for years in vivo in the absence of antigenic challenge", *J Acquir Immune Defic Syndr.*, 40(2):132-139 (2005).
Plasilova et al. "Application of the Molecular Analysis of the T-Cell Receptor Repertoire in the Study of Immune-Mediated Hematologic Diseases", *Hematology*, 8(3): 173-181 (2003).
Pohl, G. and Shih. "Principle and applications of digital PCR", *Expert Rev. Mol. Diagn.*, 4(1):41-47 (2004).
Pop and Salzberg. "Bioinformatics challenges of new sequencing technology", *NIH, Trends Genet.*, 24(3): 142-149 (2008).
Pourmand, et al. "Direct electrical detection of DNA synthesis", *PNAS*, 103(17): 6466-6470 (2006). Epub Apr. 13, 2006.
Polz and Cavanaugh. "Bias in Template-to-Product Ratios in Multitemplate PCR", *Applied and Environmental Microbiology*, 64(10): 3724-3730 (1998).
Porter, et al. "Chimeric antigen receptor-modified T cells in chronic lymphoid leukemia", N Engl J Med., 365(8):725-33 (2011). doi: 10.1056/NEJMoa1103849. Epub Aug. 10, 2011.
Prabakaran et al. "454 antibody sequencing—error characterization and correction", *BMC Research Notes*, 4: 404 (2011).
Puisieux, I. et al., "Oligoclonality of Tumor-Infiltrating Lymphocytes from Human Melanomas," *The Journal of Immunology*, 153:2807-2818 (1994).
Putnam, et al. "Clinical grade manufacturing of human alloantigen-reactive regulatory T cells for use in transplantation", Am J Transplant., 13(11): 3010-3020 (2013). doi: 10.1111/ajt.12433. Epub Sep. 18, 2013.
Qiu et al. "DNA sequence-based "bar codes" for tracking the origins of expressed sequence tags from a maize cDNA library constructed using multiple mRNA sources", *Plant Physiology*, 133(2): 475-481 (2003).
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].
Ramsden, et al. "V(D)J recombination: Born to be wild", *Semin Cancer Biol.*, 20(4): 254-260 (2010). doi: 10.1016/j.semcancer.2010.06.002. Epub Jul. 1, 2010.
Rao, Sridhar, "B cell activation and Humoral Immunity", Jan. 22, 2009 (Jan. 22, 2009), pp. 1-9, XP055192552, Retrieved from the Internet: URL:http://www.microrao.com/micronotes/pg/humoral_immunity.pdf [retrieved on Jan. 6, 2015].
Rasmussen, T. et al. "Quantitation of minimal residual disease in multiple myeloma using an allele-specific real-time PCR assay", *Experimental Hematology*, 28:1039-1045 (2000).
Ray, et al. "Single cell multiplex PCR amplification of five dystrophin gene exons combined with gender determination", *Molecular Human Reproduction*, 7(5): 489-494 (2001).
Reddy, et al. "Monoclonal antibodies isolated without screening by analyzing the variable-gene repertoire of plasma cells", *Nature Biotechnology*, 28(9): 965-969 (2010). doi: 10.1038/nbt.1673. Epub Aug. 29, 2010.
Reddy and Georgiou. "Systems analysis of adaptive immunity by utilization of high-throughput technologies", *Current Opinion in Biotechnology*, 22(4): 584-589 (2011).
Reinartz et al. "Massively parallel signature sequencing (MPSS) as a tool for in-depth quantitative gene expression profiling in all organisms", *Brief Funct Genomic Proteomic.*, 1(1):95-104 (2002).
Reischl and Kochanowski. "Quantitative PCR. A Survey of the Present Technology", *Molecular Biotechnology*, 3:55-71 (1995).
Ria, et al. "Collagen-specific T-cell repertoire in blood and synovial fluid varies with disease activity in early rheumatoid arthritis", *Arthritis Res Ther.*, 10(6):R135, 18 pages (2008). Epub Nov. 17, 2008.
Rickinson and Moss. "Human cytotoxic T lymphocyte responses to Epstein-Barr virus infection", *Annu Rev Immunol.*, 15:405-431 (1997).
Rieder, et al. "A normalization procedure for removal of residual multiplex PCR amplification bias from ultra-deep sequencing of the

(56) References Cited

OTHER PUBLICATIONS

TCR repertoire", (Program #530W). Presented at the 62nd Annual Meeting of the American Society of Human Genetics, Nov. 7, 2012 in San Francisco, California. 2 pages.

Rieder, et al. "A normalization procedure for removal of residual multiplex PCR amplification bias from ultra-deep sequencing of the TCR repertoire", Presented at the Annual Meeting of the American Society of Hematology 2012 in Atlanta, Georgia Dec. 8-11, 2012. Poster. 1 page.

Risitano et al. "In-vivo dominant immune responses in aplastic anaemia: molecular tracking of putatively pathogenetic T-cell clones by TCRβ-CDR3 sequencing", *Lancet*, 364:355-364 (2004).

Robert, et al. "CTLA4 blockade broadens the peripheral T-cell receptor repertoire", Clin Cancer Res., 20(9):2424-32 (2014). doi: 10.1158/1078-0432.CCR-13/2648. Epub Feb. 28, 2014.

Robins, H. et al. "Ultra-sensitive detection of rare T cell clones", *Journal of Immunological Methods*, 375(1-2): 14-19 (2012). Epub Sep. 10, 2011.

Robins, et al. "CD4+ and CD8+ T cell 13 antigen receptors have different and predictable V and J gene usage and CDR3 lengths", *J. Immunol.*, 188: 115.10, Abstract (2012).

Robins et al. "Detecting and monitoring lymphoma with high-throughput sequencing" *Oncotarget*, 2:287-288 (2011).

Robins, H. et al. "Digital Genomic Quantification of Tumor Infiltrating Lymphocytes", *Science Translational Medicine*, 5:214ra169, 19 pages, Supplementary Materials (2013).

Robins, H. et al. "Comprehensive assessment of T-cell receptor β-chain diversity in αβ T cells", *Blood*, 114(19):4099-4107 (and Supplemental Materials) (2009).

Robins, et al. "Effects of aging on the human adaptive immune system revealed by high-throughput DNA sequencing of T cell receptors", *J Immunol.*, 188: 47.16, Abstract (2012).

Robins, et al. "High-throughput sequencing of T-cell receptors." Sep. 2010. Poster. 1 page.

Robins, et al. "Immune profiling with high-throughput sequencing." Presented for the ASHI 2011 conference. Oct. 2011. Poster. 1 page.

Robins, et al. "Immunosequencing: applications of immune repertoire deep sequencing", *Curr Opin Immunol.*, 25(5): 646-652 (2013). doi: 10.1016/j.coi.2013.09.017. Epub Oct. 16, 2013.

Robins, H. et al. "Overlap and Effective Size of the Human CD8+ T Cell Receptor Repertoire", *Science Transitional Medicine*, 2(47, 47ra64):17 pages, Supplemental Materials (2010).

Robins, et al. "Overlap of the human CD8+ T cell receptor repertoire." Oct. 2010. Poster. 1 page.

Robins. "Overlap and effective size of the human CD8+ T cell repertoire", Keystone Symposia held Oct. 27, 2010 to Nov. 1, 2010. Immunological Mechanisms of Vaccination (Abstract). Available online Sep. 27, 2010, 1 page.

Robins, H. et al. "The Computational Detection of Functional Nucleotide Sequence Motifs in the Coding Regions of Organisms", *Exp Biol Med*, 233(6): 665-673 (2008).

Ronaghi, et al. "A sequencing method based on real-time pyrophosphate", *Science*, 281(5375): 363, 365, 5 pages (1998).

Rosenberg, S.A. et al. "New Approach to the Adoptive Immunotherapy of Cancer with Tumor-Infiltrating Lymphocytes", *Science*, 233(4770): 1318-1321 (1986).

Rosenquist, et al. "Clonal evolution as judged by immunoglobulin heavy chain gene rearrangements in relapsing precursor-B acute lymphoblastic leukemia", *Eur J Haematol.*, 63(3):171-179 (1999).

Rothberg, et al. "An integrated semiconductor device enabling non-optical genome sequencing", *Nature*, 475(7356): 348-352 (2011). doi: 10.1038/nature10242.

Rougemont, et al. "Probabilistic base calling of Solexa sequencing data", *BMC Bioinformatics*, 9:431, 12 pages (2008).

Ryan et al. "Clonal evolution of lymphoblastoid cell lines", *Laboratory Investigation*, 86(11):1193-1200 (2006). Epub Oct. 2, 2006.

Saada, R. et al. "Models for antigen receptor gene rearrangement: CDR3 length", *Immunology and Cell Biology*, 85:323-332 (2007).

Salzberg. "Mind the gaps", *Nature Methods*, 7(2): 105-106 (2010).

Sanchez-Freire et al. "Microfluidic single-cell real-time PCR for comparative analysis of gene expression patterns", *Nature Protocols*, 7(5): 829-838 (2012).

Sandberg et al. "BIOMED-2 Multiplex Immunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).

Sandberg, et al. "Capturing whole-genome characteristics in short sequences using a naïve Bayesian classifier", *Genome Res.*, 11(8): 1404-9 (2001).

Santamaria, P. et al. "Beta-Cell-Cytotoxic CD8 T Cells from Nonobese Diabetic Mice Use Highly Homologous T Cell Receptor a-Chain CDR3 Sequences", *The Journal of Immunology*, 154(5):2494-2503 (1995).

Sato et al. "Intraepithelial CD8+ tumor-infiltrating lymphocytes and a high CD8+/regulatory T cell ratio are associated with favorable prognosis in ovarian cancer", *PNAS*, 102(51): 18538-18543 (2005). Epub Dec. 12, 2005.

Satoh et al. "Pretreatment with restriction enzyme or bovine serum albumin for effective PCR amplification of Epstein-Barr virus DNA in DNA extracted from paraffin-embedded gastric carcinoma tissue", *J Clin Microbiol.*, 36(11): 3423-3425 (1998).

Schaufelberger et al. "An uneven expression of T cell receptor V genes in the arterial wall and peripheral blood in giant cell arteritis", *Inflammation*, 31(6):372-383 (2008).

Schlissel, M.S. et al. "Leukemia and lymphoma: a cost of doing business for adaptive immunity", *Genes Dev.*, 20(12): 1539-1544 (2006).

Schloss, PD et al. Reducing the Effects of PCR Amplification and Sequencing Artifacts on 16S Rrna-Based Studies. PLoS One. Dec. 14, 2011, vol. 6, No. 12; e27310; DOI: 1 0.1371/journal.pone. 0027310.

Schmitt et al. "Detection of ultra-rare mutations by next-generation sequencing," *PNAS*, 109(36): 14508-14513 and Supporting Information, 9 pages (2012).

Schøller et al. "Analysis of T cell receptor αβ variability in lymphocytes infiltrating melanoma primary tumours and metastatic lesions", *Cancer Immunol Immunother*. 39(4):239-248 (1994).

Schrappe, M. et al. "Late MRD response determines relapse risk overall and in subsets of childhood T-cell ALL: results of the AIEOP-BFM-ALL 2000 study", *Blood*, 118(8): 2077-2084 (2011).

Schreiber et al. "Cancer immunoediting: integrating immunity's roles in cancer suppression and promotion", *Science*, 331(6024): 1565-1570 (2011). doi: 10.1126/science.1203486.

Schwab et al. "CD8+ T-cell clones dominate brain infiltrates in Rasmussen encephalitis and persist in the periphery", *Brain*, 132:1236-1246 (2009).

Schweiger et al. "Genome-wide massively parallel sequencing of formaldehyde fixed-paraffin embedded (FFPE) tumor tissues for copy-number- and mutation-analysis", *PLoS One*, 4(5): e5548, 7 pages (2009). doi: 10.1371/journal.pone.0005548. Epub May 14, 2009.

Chinese Patent Application No. 201510054401.X, Search Report dated Jul. 14, 2016, 2 pages.

Sebastian, E. et al., "Molecular Characterization of immunoglobulin gene rearrangements in diffuse large B-cell lymphoma", *Am. J. Pathol.*, 181: 1879-1888, Abstract (2012). (Epub: Sep. 28, 2012).

Sehouli et al. "Epigenetic quantification of tumor-infiltrating T-lymphocytes" *Epigenetics*, 6(2): 236-246 (2011). Epub Feb. 1, 2011.

Seitz, et al. "Reconstitution of paired T cell receptor α- and β-chains from microdissected single cells of human inflammatory tissues", *PNAS*, 103: 12057-12062 (2006).

Seo, et al. "Four-color DNA sequencing by synthesis on a chip using photocleavable fluorescent nucleotides", *PNAS*, 102(17): 5926-5931 (2005). Epub Apr. 13, 2005.

Sfanos et al. "Human Prostate-Infiltrating CD8+ T Lymphocytes are Oligoclonal and PD-1+", *The Prostate*, 69(15): 1694-1703 (2009).

Sfanos et al. "Phenotypic analysis of prostate-infiltrating lymphocytes reveals TH17 and Treg skewing", *Clinical Cancer Research*, 14(11):3254-3261 (2008). doi: 10.1158/1078-0432.CCR-07-5164.

Shen et al. "Comparing platforms for *C. elegans* mutant identification using high-throughput whole-genome sequencing", *PLoS One*, 3(12):e4012, 6 pages (2008).

(56) References Cited

OTHER PUBLICATIONS

Shendure, et al. "Advanced sequencing technologies: methods and goals", *Nat Rev Genet.*, 5(5): 335-344 (2004).

Shendure and JI. "Next-generation DNA sequencing", *Nature Biotechnology*, 26(10):1135-1145 (2008).

Sherwood, A. et al. "Deep Sequencing of the Human TCRγ and TCRβ Repertoires Suggests that TCRβ Rearranges After αβ and γδ T Cell Commitment, Science Translational Medicine", *Sci. Transl. Med.*, 3(90): 1-7 (2011).

Sherwood, et al. "New Technologies for Measurements of Tumor Infiltrating Lymphocytes", Presented Nov. 7, 2012 Moscone Center, Exhibit Halls ABC.

Sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.

Shino, et al. "Usefulness of immune monitoring in lung transplantation using adenosine triphosphate production in activated lymphocytes", *The Journal of Heart and Lung Transplant*, 31: 996-1002 (2012).

Shiroguchi et al. "Digital RNA sequencing minimizes sequence-dependent bias and amplification noise with optimized single-molecule barcodes", *PNAS*, 109(4): 1347-1352 (2012).

Shoemaker et al. "Quantitative phenotypic analysis of yeast deletion mutants using a highly parallel molecular bar-coding strategy," *Nature Genetics*, 14(4): 450-456 (1996).

Shumaker, et al. "Mutation detection by solid phase primer extension", *Hum Mutat.*, 7(4): 346-354, Abstract Only (1996).

Sia, et al. "Microfluidic devices fabricated in poly(dimethylsiloxane) for biological studies", *Electrophoresis*, 24(21): 3563-3576, Abstract Only (2003).

Sims, et al. "Fluorogenic DNA sequencing in PDMS microreactors", *Nat Methods*, 8(7): 575-580 (2011). doi: 10.1038/nmeth.1629.

Sims, et al. "MHC-peptide tetramers for the analysis of antigen-specific T cells", *Expert Rev Vaccines*, 9(7): 765-774 (2010). doi: 10.1586/erv.10.66.

Sing et al. "A molecular comparison of T Lymphocyte populations infiltrating the liver and circulating in the blood of patients with chronic hepatitis B: evidence for antigen-driven selection of a public complementarity-determining region 3 (CDR3) motif", *Hepatology*, 33(5):1288-1298 (2001).

Sint, D., et al. "Advances in multiplex PCR: balancing primer efficiencies and improving detection success", *Methods in Ecology and Evolution*, 3(5): 898-905 (2012).

Skulina et al. "Multiple Sclerosis: Brain-infiltrating CD8+ T cells persist as clonal expansions in the cerebrospinal fluid and blood", *PNAS*, 101(8):2428-2433 (2004).

Smith, et al. "Comparison of biosequences", *Advances in Applied Mathematics*, 2: 482-489 (1981).

Smith et al. "Rapid generation of fully human monoclonal antibodies specific to a vaccinating antigen", *Nature Protocols*, 4(3): 372-384 and CORRIGENDA (2009).

Smith et al. "Rapid whole-genome mutational profiling using next-generation sequencing technologies", *Genome Research*, 18: 1638-1642 (2008).

Sobrino, et al. "SNPs in forensic genetics: a review on SNP typing methodologies", *Forensic Sci Int.*, 154(2-3): 181-194, Abstract Only (2005). Epub Jan. 11, 2005.

Speiser et al., "A novel approach to characterize clonality and differentiation of human melanoma-specific T cell responses: spontaneous priming and efficient boosting by vaccination." *The Journal of Immunology*, 177(2): 1338-1348 (2006).

Spreafico, et al. "A circulating reservoir of pathogenic-like CD4+ T cells shares a genetic and phenotypic signature with the inflamed synovial micro-environment", *Ann Rheum Dis.*, 0: 1-7 (2014). doi: 10.1136/annrheumdis-2014-206226. [Epub ahead of print].

Sramkova, et al. "Detectable minimal residual disease before allogeneic hematopoietic stem cell transplantation predicts extremely poor prognosis in children with acute lymphoblastic leukemia", *Pediatr. Blood Cancer*, 48(1):93-100 (2007).

Srinivasan et al. "Effect of fixatives and tissue processing on the content and integrity of nucleic acids", *Am J Pathol.*, 161(6): 1961-1971 (2002).

Srivastava and Robins. "Palindromic nucleotide analysis in human T cell receptor rearrangements", PLoS One, 7(12):e52250 (2012). doi: 10.1371/journal.pone.0052250. Epub Dec. 21, 2012.

Steenbergen, et al. "Distinct ongoing Ig heavy chain rearrangement processes in childhood B-precursor acute lymphoblastic leukemia", *Blood*, 82(2):581-589 (1993).

Steenbergen, et al. "Frequent ongoing T-cell receptor rearrangements in childhood B-precursor acute lymphoblastic leukemia: implications for monitoring minimal residual disease", *Blood*, 86(2): 692-702, Abstract Only (1995).

Stemmer, et al. "Single-step assembly of a gene and entire plasmid from large numbers of oligodeoxyribonucleotides", *Gene*, 164(1): 49-53 (1995).

Steward et al. "A polymerase chain reaction study of the stability of Ig heavy-chain and T-cell receptor delta gene rearrangements between presentation and relapse of childhood B-lineage acute lymphoblastic leukemia", *Blood*, 83(5):1355-1362 (1994).

Stewart and Schwartz. "Immunoglobulin V regions and the B cell", *Blood*, 83(7): 1717-1730 (1994).

Stickler, et al. "An in vitro human cell-based assay to rank the relative immunogenicity of proteins", *Toxicol Sci.*, 77(2): 280-289 (2004). Epub Dec. 22, 2003.

Stiller et al. "Direct multiplex sequencing (DMPS)—a novel method for targeted high-throughput sequencing of ancient and highly degraded DNA", *Genome Research*, 19: 1843-849 (2009).

Straten, Per thor, et al. "T-cell clonotypes in cancer", *Journal of Translational Medicine*, 2(1): 11, 10 pages (2004).

Stratton. "Exploring the genomes of cancer cells: progress and promise", *Science*, 331(6024): 1553-1558 (2011). doi: 10.1126/science.1204040.

Striebich, et al. "Selective Accumulation of Related CD41 T Cell Clones in the Synovial Fluid of Patients with Rheumatoid Arthritis", *J Immunol.*, 161(8): 4428-4436 (1998).

Struyk et al. "T cell receptors in rheumatoid arthritis", *Arthritis & Rheumatism*, 38(5):577-589 (1995).

Sumida et al. "T cell receptor repertoire of infiltrating T cells in lips of Sjögren's syndrome patients", *J Clin Invest.*, 89:681-685 (1992).

Sumida et al. "T cell receptor Vα repertoire of infiltrating T cells in labial salivary glands from patients with Sjögren's syndrome", *J Rheumatol.*, 21:1655-1661 (1994).

Swarup and Rajeswari. "Circulating (cell-free) nucleic acids—a promising, non-invasive tool for early detection of several human diseases", *FEBS Letters*, 581(5): 795-799 (2007). Epub Feb. 2, 2007.

Szczepanski et al. "Comparative analysis of Ig and TCR gene rearrangements at diagnosis and at relapse of childhood precursor-B-ALL provides improved strategies for selection of stable PCR targets for monitoring of minimal residual disease", *Blood*, 99(7):2315-2323 (2002).

Szczepanski, T. et al. "Minimal residual disease in leukemia patients", *Lancet Oncology*, 2:409-417 (2001).

Szczepanski et al. "Why and how to quantify minimal residual disease in acute lymphoblastic leukemia'?", *Leukemia*, 21(4):622-626 (2007). Epub Feb. 15, 2007.

Tackenberg et al. "Clonal expansions of CD4+ β helper T cells in autoimmune myasthenia gravis", *European Journal of Immunology*, 37(3):849-863 (2007).

Tajiri et al. "Cell-microarray analysis of antigen-specific B-cells: single cell analysis of antigen receptor expression and specificity", *Cytometry Part A*, 71A: 961-967 (2007).

Takamatsu, et al., "A comparison between next-generation sequencing and ASO-qPCR for minimal residual disease detection in multiple myeloma", *J. Clin. Oncol.*, 31(Supplement 1): Abstract 8601 (Conference Abstract), Entire Abstract (2013).

Tanaka et al. "Single-Cell Analysis of T-Cell Receptor Repertoire of HTLV-1 Tax-Specific Cytotoxic T Cells in Allogeneic Transplant Recipients with Adult T-Cell Leukemia/Lymphoma", *Cancer Research*, 70: 6181-6192 (2010).

(56) References Cited

OTHER PUBLICATIONS

Taubenheim et al. "High Rate of Antibody Secretion Is not Integral to Plasma Cell Differentiation as Revealed by XBP-1 Deficiency", *The Journal of Immunology*, 189: 3328-3338 (2012).
Tautz, et al. "Cryptic simplicity in DNA is a major source of genetic variation", *Nature*, 322(6080): 652-656 (1986).
Tawfik, et al. "Man-made cell-like compartments for molecular evolution", *Nat Biotechnol.*, 16(7): 652-656, Abstract Only (1998).
Taylor et al., "Intraclonal homogeneity of clonotypic immunoglobulin M and diversity of nonclinical post-switch isotypes in multiple myeloma: insights into the evolution of the myeloma clone", Clin Cancer Res., 8(2): 502-513 (2002).
Ten Bosch et al. "Keeping Up With the Next Generation Massively Parallel Sequencing in Clinical Diagnostics", *Journal of Molecular Diagnostics*, 10(6): 484-492 (2008).
Tewhey, R. et al. "Microdroplet-based PCR enrichment for large-scale targeted sequencing," *Nature Biotechnology*, 27(11):1025-1031 (2009).
Thiel, et al. "Antigen-specific cytometry—new tools arrived!", *Clin Immunol.*, 111(2): 155-161, Abstract Only (2004).
Thornhill et al. "A comparison of different lysis buffers to assess allele dropout from single cells for preimplantation genetic diagnosis", *Prenatal Diagnosis*, 21:490-497 (2001).
Tokimitsu et al. "Single lymphocyte analysis with a microwell array chip", *Cytometry Part A*, 71A:1003-1010 (2007).
Toriello et al. "Integrated microfluidic bioprocessor for single-cell gene expression analysis", *PNAS*, 105(51): 20173-20178 (2008).
Triebel, F. et al. "A Unique V-J-C-Rearranged Gene Encodes A γ Protein Expressed on the Majority of CD3+ T Cell Receptor -a/fr Circulating Lymphocytes", *J. Exp. Med.*, 167:694-699 (1988).
Tsankova, et al. "Peripheral T-cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.
Tschumper, et al. "Comprehensive assessment of potential multiple myeloma immunoglobulin heavy chain V-D-J intraclonal variation using massively parallel pyrosequencing", *Oncotarget*, 3(4): 502-513 (2012).
Turcotte and Rosenberg. "Immunotherapy for metastatic solid cancers", *Adv Surg.*, 45: 341-360 (2011).
UK combined search and examination report dated Mar. 20, 2013 for GB 1300533.5.
UK Combined Search Report and Office action dated Jun. 29, 2012 for UK application No. GB1209668.1.
UK Combined Search Report and Office action dated May 27, 2011 for UK application No. GB1105068.9.
UK Search Report and office action dated Jan. 13, 2012 for UK application No. GB1120209.0.
UK Search Report and office action dated Jul. 7, 2010 for UK application No. GB1009641.0.
Umibe et al. "Clonal expansion of T cells infiltrating in the airways of non-atopic asthmatics", *Clinical & Experimental Immunology*, 119(3):390-397 (2000).
Unrau and Deugau. "Non-cloning amplification of specific DNA fragments from whole genomic DNA digests using DNA 'indexers'", *Gene.*, 145(2): 163-169, Abstract Only, 2 pages (1994).
Uppaluri et al. "Focus on TILs: prognostic significance of tumor infiltrating lymphocytes in head and neck cancers", *Cancer Immunity*, 8:16, 10 pages (2008).
Urban, et al. "A systematic and quantitative analysis of PCR template contamination", *J Forensic Sci.*, 45(6): 1307-1311 (2000).
Van Dervelden, V.H.J., et al. "Analysis of minimal residual disease by Ig/TCR gene rearrangements: guidelines for interpretation of real-time quantitative PCR data," *Leukemia*, 21:604-611 (2007).
Van Dervelden, V.H.J., et al. "Detection of minimal residual disease in hematologic malignancies by realtime quantitative PCR: principles, approaches, and laboratory aspects," *Leukemia*, 17:1013-1034 (2003).
Van Der Velden, V.H.J., et al. "Real-time quantitative PCR for detection of minimal residual disease before allogeneic stem cell transplantation predicts outcome in children with acute lymphoblastic leukemia", *Leukemia*, 15:1485-1487 (2001).
Van Dongen, J.J.M. et al. "Design and standardization of PCR primers and protocols for detection of clonal immunoglobulin and I-cell receptor gene recombinations in suspect lymphoproliferations: Report of the BIOMED-2 Concerted Action BMHC-CT98-3936", *Leukemia*, 17:2257-2317 (2003).
Van Dongen, J.J.M. et al. "Prognostic value of minimal residual disease in acute lymphoblastic leukaemia in childhood", *The Lancet*, 352:1731-1738 (1998).
Varley and Mitra. "Nested patch PCR enables highly multiplexed mutation discovery in candidate genes", *Genome Research*, 18: 1844-1850 (2008).
Venturi, et al. "A mechanism for TCR sharing between T cell subsets and individuals revealed by pyrosequencing", *J Immunol.*, 186(7): 4285-4294 (2011). doi: 10.4049/jimmunol.1003898. Epub Mar. 7, 2011.
Venturi, V. et al. "TCR β-Chain Sharing in Human CD8$^+$ T Cell Responses to Cytomegalovirus and EBV[1]", *The Journal of Immunology*, 181:7853-7862 (2008).
Vester, et al. "LNA (locked nucleic acid): high-affinity targeting of complementary RNA and DNA", *Biochemistry*, 43(42): 13233-13241, Abstract Only (2004).
Vlassov, et al. "Circulating nucleic acids as a potential source for cancer biomarkers", *Curr Mol Med.*, 10(2): 142-165 (2010).
Vogelstein et al. "Cancer genome landscapes", *Science*, 339(6127): 1546-1558 (2013). doi: 10.1126/science.1235122.
Wälchli, et al. "A practical approach to T-cell receptor cloning and expression", *PLoS One*, 6(11): e27930, 11 pages (2011). doi: 10.1371/journal.pone.0027930. Epub Nov. 21, 2011.
Wang, et al. "Balanced-PCR amplification allows unbiased identification of genomic copy changes in minute cell and tissue samples", *Nucleic Acids Research*, 32(9): e76, 10 pages (2004).
Wang, et al. "High throughput sequencing reveals a complex pattern of dynamic interrelationships among human T cell subsets", *PNAS*, 107(4): 1518-1528 (2010).
Wang et al. "Immunorepertoire analysis by multiplex PCR amplification and high throughput sequencing", Poster—Program 42.6, The 96th Annual Meeting of the America Association of Immunologists, Seattle, USA, May 8-12, 2009, 1 page.
Wang, X. et al. "Quantitative Measurement of Pathogen Specific Human Memory T Cell Repertoire Diversity using a CDR3 B-Specific Microarray", *BMC Genomics*, 8(329): 1-13 (2007).
Warren et al. "Exhaustive T-cell repertoire sequencing of human peripheral blood samples reveals signatures of antigen selection and a directly measured repertoire size of at least 1 million clonotypes", *Genome Res.*, 21(5): 790-797 (2011). Epub Feb. 24, 2011.
Warren et al. "Profiling model T-cell metagenomes with short reads", *Bioinformatics*, 25(4):458-464 (2009).
Weiss et al. "Clonal Rearrangements of T-Cell Receptor Genes in Mycosis Fungoides and Dermatopathic Lymphadenopathy", *The New England Journal of Medicine*, 313(9):539-544 (1985).
Welch and Link. "Genomics of AML: clinical applications of next-generation sequencing", *American Society of Hematology*, 2011: 30-35 (2011). doi: 10.1182/asheducation-2011.1.30.
Wells, et al. "Rapid evolution of peptide and protein binding properties in vitro", *Curr Opin Biotechnol.*, 3(4): 355-362, Abstract Only (1992).
Wells, et al. "Strategies for preimplantation genetic diagnosis of single gene disorders by DNA amplification", *Prenatal Diagnosis*, 18(13):1389-1401 (1998).
Weng, et al. "Minimal residual disease monitoring with high-throughput sequencing of T cell receptors in cutaneous T cell lymphoma", Sci Transl Med., 5(214):214ra171 (2013). doi: 10.1126/scitranslmed.3007420.
Westermann and Pabst. "Distribution of lymphocyte subsets and natural killer cells in the human body", *Clin Investig.*, 70(7): 539-544 (1992).
Wetmur and Chen. "An emulsion polymerase chain reaction-based method for molecular haplotyping", *Methods in Molecular Biology*, 410: 351-361 (1996).

(56) References Cited

OTHER PUBLICATIONS

Wetmur and Chen. "Linking emulsion PCR haplotype analysis", chapter 11, Park, D.J. (ed.), *PCR Protocols, Methods in Molecular Biology*, 687: 165-175 (2011).
Wetmur et al. "Molecular haplotyping by linking emulsion PCR: analysis of paraoxonase 1 haplotypes and phenotypes", *Nucleic Acids Research*, 33(8):2615-2619 (2005).
Weusten, et al. "Principles of quantitation of viral loads using nucleic acid sequence-based amplification in combination with homogeneo detection using molecular beacons", Nucleic Acids Res., 30(6): e26, 7 pages (2002).
White et al. "High-throughput microfluidic single-cell RT-qPCR", *PNAS*, 108(34): 13999-14004 (2011).
Whiteford, et al. "Swift: primary data analysis for the Illumina Solexa sequencing platform", *Bioinformatics*, 25(17): 2194-2199 (2009). doi: 10.1093/bioinformatics/btp383. Epub Jun. 23, 2009.
Wlodarski et al. "Molecular strategies for detection and quantitation of clonal cytotoxic T-cell responses in aplastic anemia and myelodysplastic syndrome", *Blood*, 108(8):2632-2641 (2006).
Wlodarski et al. "Pathologic clonal cytotoxic T-cell responses: nonrandom nature of the T-cell-receptor restriction in large granular lymphocyte leukemia", *Blood*, 106:2769-2779 (2005).
Wolfl, et al. "Activation-induced expression of CD137 permits detection, isolation, and expansion of the full repertoire of CD8+ T cells responding to antigen without requiring knowledge of epitope specificities", *Blood*, 110(1): 201-210 (2007). Epub Mar. 19, 2007.
Wolfl, et al. "Use of CD137 to study the full repertoire of CD8+ T cells without the need to know epitope specificities", *Cytometry A.*, 73(11): 1043-1049 (2008). doi: 10.1002/cyto.a.20594.
Wood, et al. "Using next-generation sequencing for high resolution multiplex analysis of copy number variation from nanogram quantities of DNA from formalin-fixed paraffin-embedded specimens", *Nucleic Acids Research*, 38(14): e151, 11 pages (2010). doi: 10.1093/nar/gkq510. Epub Jun. 4, 2010.
Wrammert et al. "Rapid cloning of high-affinity human monoclonal antibodies against influenza virus", *Nature*, 453: 667-672 (2008).
Wu, et al. "High-throughput sequencing detects minimal residual disease in acute T lymphoblastic leukemia", Sci Transl Med., 4(134):134ra63 (2012). doi: 10.1126/scitranslmed.3003656.
Wu, et al. "High-throughput sequencing of T-cell receptor gene loci for minimal residual disease monitoring in T Lymphoblastic Leukemia", Blood, 118: 2545 (Abstr) (2011).
Wu, Y-C. et al. "High-throughput immunoglobulin repertoire analysis distinguishes between human IgM memory and switched memory B-cell populations", *Blood Journal*, 116(7): 1070-1078, 22 pages (2010).
Wu et al. "Focused Evolution of HIV-1 Neutralizing Antibodies Revealed by Structures and Deep Sequencing", *Science*, 333: 1593-1602 (2011).
Wu, H.D. et al. "The Lymphocytic Infiltration in Calcific Aortic Stenosis Predominantly Consists of Clonally Expanded T Cells", *The Journal of Immunology*, 178(8): 5329-5339 (2007).
Xiong, et al. "Non-polymerase-cycling-assembly-based chemical gene synthesis: strategies, methods, and progress", *Biotechnol Adv.*, 26(2): 121-134, Abstract Only (2008). Epub Nov. 7, 2007.
Xu, W. et al. "A Novel Universal Primer-Multiplex-PCR Method with Sequencing Gel Electrophoresis Analysis", *PLoS One*, 7(1): e22900, 10 pages (2012).
Xu, et al. "Simultaneous isolation of DNA and RNA from the same cell population obtained by laser capture microdissection for genome and transcriptome profiling", *J Mol Diagn.*, 10(2):129-134 (2008). doi: 10.2353/jmoldx.2008.070131. Epub Feb. 7, 2008.
Yao, et al. "Analysis of the CDR3 length repertoire and the diversity of TCRα chain in human peripheral blood T Lymphocytes", Cell Mol Immunol., 4(3): 215-220 (2007).
Yeh, et al. "Regulating DNA translocation through functionalized soft nanopores", *Nanoscale*, 4(8): 2685-4693, Abstract Only (2012). doi: 10.1039/c2nr30102d. Epub Mar. 15, 2012.
Yassai, M.B. et al. "A clonotype nomenclature for T cell receptors", *Immunogenetics*, 61:493-502 (2009).
Yin et al. "Antiretroviral therapy restores diversity in the T-cell receptor Vβ repertoire of CD4 T-cell subpopulations among human immunodeficiency virus type 1-infected children and adolescents", *Clinical and Vaccine Immunology*, 16(9):1293-1301 (2009).
Yon and Fried. "Precise gene fusion by PCR", *Nucleic Acids Research*, 17(12):4895, 1 page (1989).
York, et al. "Highly parallel oligonucleotide purification and functionalization using reversible chemistry", *Nucleic Acids Res.*, 40(1): e4, 7 pages (2012). doi: 10.1093/nar/gkr910. Epub Oct. 29, 2011.
Yu and Fu. "Tumor-infiltrating T lymphocytes: friends or foes?", *Lab Invest.*, 86(3): 231-245 (2006).
Zagnoni, et al. "Droplet Microfluidics for High-throughput Analysis of Cells and Particles", *Methods in Cell Biology*, Chapter 2, 102: 23-48 (2011).
Zaliova, et al. "Quantification of fusion transcript reveals a subgroup with distinct biological properties and predicts relapse in BCR/ABL-positive ALL: implications for residual disease monitoring", *Leukemia*,23(5):944-951 (2009).
Zehentner et al. "Minimal Disease Detection and Confirmation in Hematologic Malignancies: Combining Cell Sorting with Clonality Profiling", *Clinical Chemistry*, 52(3): 430-437 (2006).
Zeng et al. "High-performance single cell genetic analysis using microfluidic emulsion generator arrays", *Anal. Chem.*, 82(8):3183-3190 (2010).
Zhang, Minying, et al. "A New Approach to Simultaneously Quantify Both TCR α- and β-Chain Diversity after Adoptive Immunotherapy." Clinical Cancer Research (2012); 18(17): 4733-4742.
Zhong, Q. et al. "Multiplex digital PCR: breaking the one target per color barrier of quantitative PCR", Lab Chip, 11:2167-2174 (2011).
Zhou et al. "High throughput analysis of TCR-β rearrangement and gene expression in single cells", *Laboratory Investigation*, 86: 314-321 (2006).
Zhou et al. "Isolation of purified and live Foxp3+ regulatory T cells using FACS sorting on scatter plot", *J Mol Cell Biol.*, 2(3): 164-169 (2010). doi: 10.1093/jmcb/mjq007. Epub Apr. 29, 2010.
Zimmerman and Mannhalter. "Technical aspects of quantitative competitive PCR", *Biotechniques*, 21: 268-279 (1996).
Curran, et al., "PD-1 and CTLA-4 combination blockade expands infiltrating T cells and reduces regulatory T and myeloid cells within B16 melanoma tumors." PNAS (2010); 107: 4275-4280.
DeWitt, et al., "Dynamics of the Cytotoxic T Cell Response to a Model of Acute Viral Infection." J. Virol. (2015); 89 (8): 4517-4526.
European Patent Application No. 17199432.0, Extended European Search Report dated Feb. 14, 2018, 10 pages.
European Patent Application No. 15864123.3, Extended European Search Report dated Mar. 19, 2018, 8 pages.
Fang, et al., "Immunotherapy for Advanced Melanoma." Journal of Investigative Dermatology (2008); 128: 2596-2605.
Födinger et al., "Multiplex PCR for rapid detection of T-cell receptor-gamma chain gene rearrangements in patients with lymphoproliferative diseases." British Journal of Haematology (1996); 94(1): 136-139.
Georgiou, G., et al., "The promise and challenge of high-throughput sequencing of the antibody repertoire." Nat Biotechnol (2014); 32(2): 158-168.
Hamid, et al., "A prospective phase II trial exploring the association between tumor microenvironment biomarkers and clinical activity of ipilimumab in advanced melanoma." Journal of Translational Medicine (2011); 9: 204, internet pp. 1-16.
Howie, et al., "High throughput pairing of T cell receptor α and β sequences." Science Translational Medicine (2015); 7(301): 301ra131, and supplementary materials, 19 pages.
Panzara, et al., "Analysis of the T cell repertoire using the PCR and specific oligonucleotide primers." Biotechniques (1992); 12(5): 728-735.
Sensi, et al., "T Cell Receptor (TCR) Structure of Autologous Melanoma-reactive Cytotoxic T Lymphocyte (CTL) Clones: Tumor-infiltrating Lymphocytes Overexpress In Vivo the TCR β Chain Sequence Used by an HLA-A2-restricted and Melanocyte-lineage-specific CTL Clone." Journal of Experimental Medicine (1993); 178: 1231-1246.

(56) References Cited

OTHER PUBLICATIONS

Sotomayor, et al., "Conversion of tumor-specific CD4+ T-cell tolerance to T-cell priming through in vivo ligation of CD40." Nature Medicine (1999); 5(7): 780-787.

Szczepek, et al., "A high frequency of circulating B cells share clonotypic Ig heavy-chain VDJ rearrangements with autologous bone marrow plasma cells in multiple myeloma, as measured by single-cell and in situ reverse transcriptase-polymerase chain reaction." Blood (1998); 92(8): 2844-2855.

Tarhini, et al., "Neoadjuvant ipilimumab in locally/regionally advanced melanoma: Clinical outcome and immune monitoring." J Clinical Oncology (2012); 30 (suppl; abstract 8533), presented Jun. 2, 2012, 2 pages.

Willenbrock, et al., "Analysis of T-Cell Subpopulations in T-Cell Non-Hodgkin's Lymphoma of Angioimmunoblastic Lymphadenopathy with Dysproteinemia Type by Single Target Gene Amplification of T Cell Receptor-β Gene Rearrangements." Am J Pathol. (2001); 158(5): 1851-1857.

Yagi, et al., "Detection of clonotypic IGH and TCR rearrangements in the neonatal blood spots of infants and children with B-cell precursor acute lymphoblastic leukemia." Blood (2000); 96(1): 264-268.

* cited by examiner

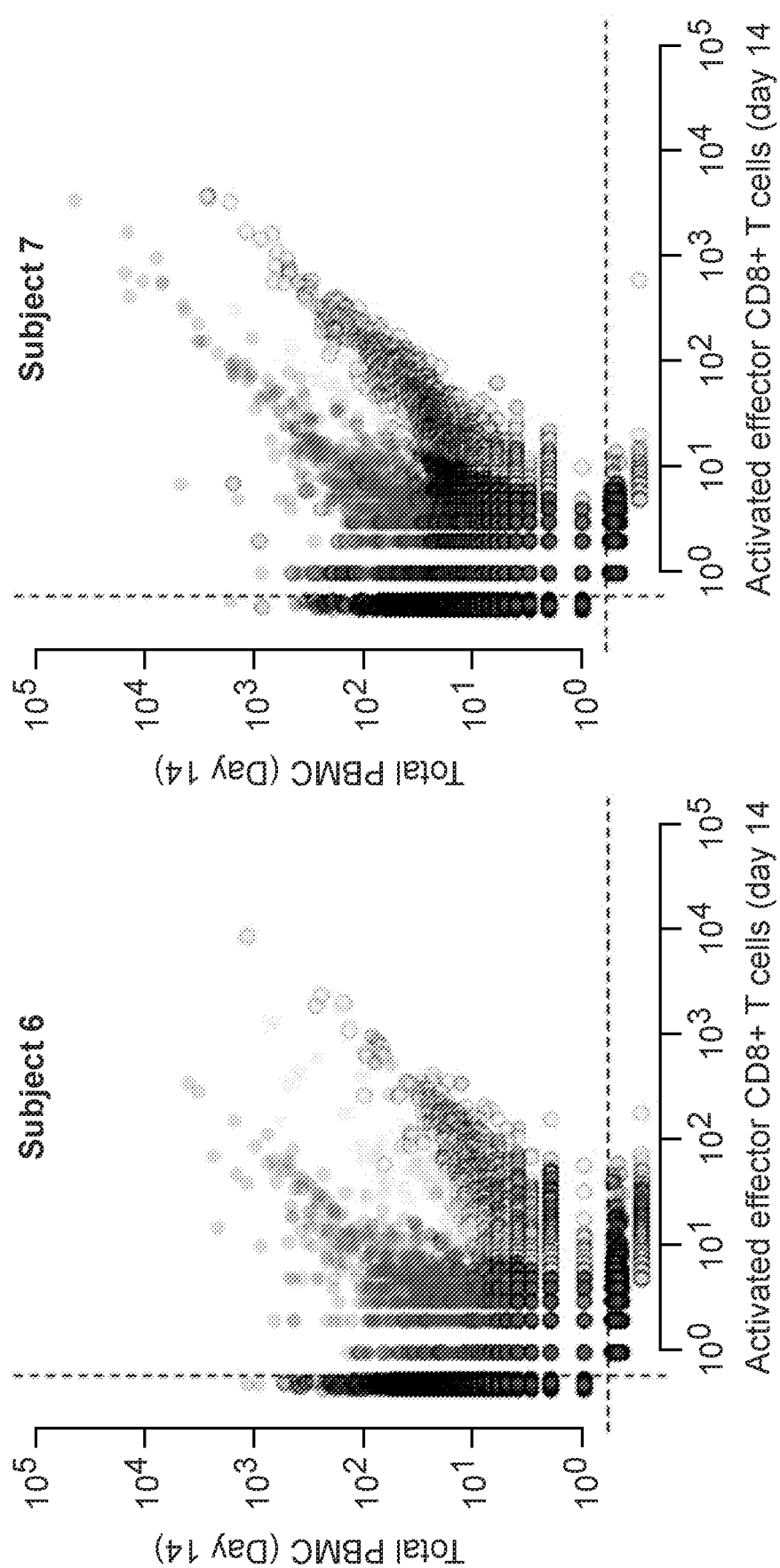

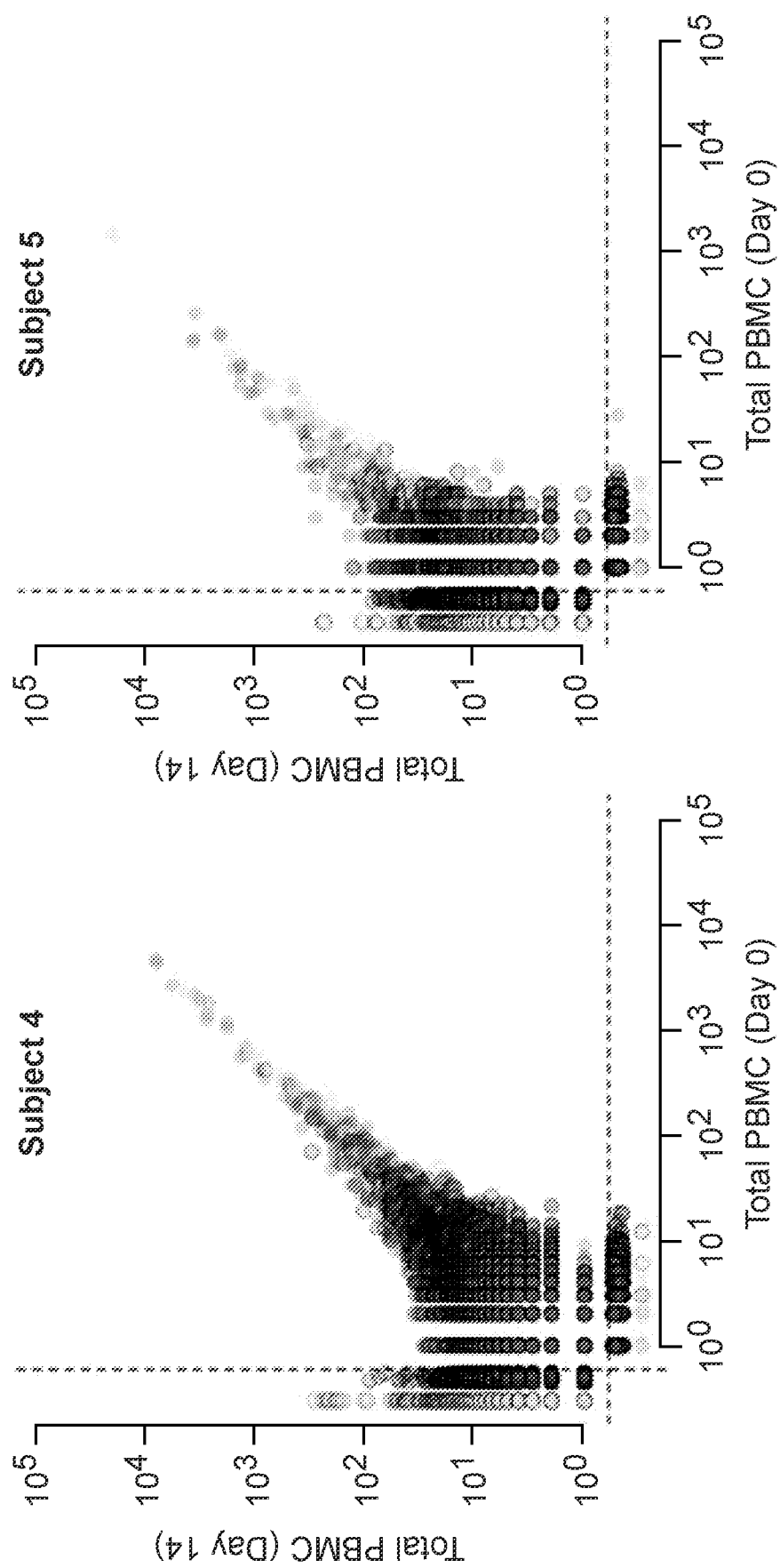

CHARACTERIZATION OF ADAPTIVE IMMUNE RESPONSE TO VACCINATION OR INFECTION USING IMMUNE REPERTOIRE SEQUENCING

CROSS REFERENCE TO RELATED APPLICATIONS

This application is the national stage of International Patent Application No. PCT/US2015/062494, filed on Nov. 24, 2015, which claims the benefit of U.S. Provisional Application No. 62/084,470, filed Nov. 25, 2014, which is hereby incorporated in its entirety by reference.

STATEMENT REGARDING FEDERALLY SPONSORED RESEARCH OR DEVELOPMENT

This invention was made with government support under AI081860 awarded by the National Institutes of Health. The government has certain rights in the invention.

BACKGROUND OF THE INVENTION

Field of the Invention

The disclosure relates to methods of characterizing an adaptive immune response to an infection or a vaccination by analyzing the repertoire of rearranged CDR3 regions of T cell receptor genes or immunoglobulin genes.

Description of the Related Art

Researchers have attempted to study the adaptive immune response to an infection caused by foreign pathogens, such as parasites, bacteria or viruses, which can inform the dynamics of the response to the infection or the effectiveness of a treatment.

For instance, the detailed characterization of the dynamics and breadth of the human immune response to a vaccination can greatly contribute to a basic understanding of the immune system and guide the design of effective new vaccines. Both neutralizing antibodies produced by B cells and effector T cells, especially CD8+ T cells (cytotoxic T lymphocytes, or CTLs), have been shown to be critical for the effective resolution of acute viral infections.

Moreover, during the acute response to a viral infection, viral antigen-specific effector B cell and T cell clones become activated and expand as they recognize and eliminate infected host cells (Kaech and Wherry, 2007, Immunity 27:393-405; Wherry et al. 2007 Immunity 27:670-684). The antigen specificity of a B cell clone and a T cell clone is determined by the B cell receptor (BCR) and T cell receptor (TCR), respectively, which are encoded by random, RAG-mediated V(D)J recombination. Thus, each T cell clone may be identified by its unique TCRβ CDR3 region, formed from the joining of the V, D and J gene segments, with CDR3 being the primary determinant of antigen specificity (Engel and Hedrick, 1988, Cell 54:473-484; Jorgensen et al. 1992, Nature 355:224-230). Similarly, each B cell clone may be identified by its unique immunoglobulin heavy chain (IgH) CDR3 region, formed from the joining of the V, D and J gene segments.

The identification and tracking of virus-specific T cell clones has resulted in the extensive characterization of the phenotype and function of virus-specific T cells (McHeyzer-Williams and Davis, 1995, Science 268:106-111; Miller et al. 2008, Immunity 28:710-722; Newell et al. 2012, Immunity 36:142-152; Precopio et al. 2007, The Journal of Experimental Medicine 204:1405-1416). Importantly, responses to chronic and acute viruses seem to be characterized by different patterns of activation and waning of effector cells, as well as different memory cell phenotypes, which might be related to the different patterns of exposures to viral antigens in the two types of infections (Ahmed and Akondy, 2011, Immunology and cell biology 89:340-345).

The identification of virus-specific T cells during the course of an infection has allowed the measurement of the number of unique clones responding to a particular viral epitope (Akondy et al. 2009, Journal of immunology 183:7919-7930; Co et al. 2002, Virology 293:151-163; Turner et al. 2003, Immunity 18:549-559). These studies suggest that the magnitude of the T cell clonal response to different viral antigens is not uniform. For example, in the case of the yellow fever vaccine (YFV), peptide NS4b induces a more robust T cell response than peptide NS5 (Akondy et al. 2009, Journal of immunology 183:7919-7930; Blom et al. 2013, Journal of immunology 190:2150-2158). Moreover, there is extensive variability in the number of unique clones activated by a particular viral epitope (Manuel et al. 2006, Journal of virology 80:12032-12040; Miconnet et al. 2011, Journal of immunology 186:7039-7049), which depends on both the quantity of peptide presented (Henrickson et al. 2013, Immunity 39:496-507) and on the microenvironment of the lymph node where the T cell encounters antigen (Newell et al. 2012, Immunity 36:142-152). Finally, major histocompatibility complexes (MHC) polymorphisms lead to variable epitope presentation in different individuals (Achour et al. 2002, Immunity 17:757-768; Eckle et al. 2013, Current Opinion in Immunology 25:653-659), complicating the characterization of dominant and non-dominant clonal CTL responses.

The formation of virus-specific memory cells is also believed to be dependent on the magnitude of the clonal response to antigen (Hou et al. 1994, Nature 369:652-654; Vezys et al. 2009, Nature 457:196-199). After an acute infection is resolved, the virus-specific effector cell pool contracts (Badovinac et al. 2002, Nature immunology 3:619-626), and a much smaller number of long-lived memory cells that are capable of responding to subsequent infections are maintained (Sung et al. 2012, Cell 150:1249-1263). It is thought that effector cell clones present in high abundance are recruited to the memory repertoire with higher frequency than less abundant clones (Turner et al. 2003, Immunity 18:549-559; Flynn et al. 1998, Immunity 8:683-691; Sourdive et al. 1998, The Journal of experimental medicine 188:71-82), but it is not clear whether this simply reflects the limitations of currently available techniques. Therefore highly sensitive techniques are necessary to establish the contribution of less abundant clones to the memory pool (Blom et al. 2013, Journal of Immunology 190:2150-2158). Furthermore, to date, it has not been possible to relate the magnitude and diversity of the effector cell response to the subsequent abundance of individual clones in the memory cell repertoire.

Since exposure to YFV is geographically limited, and YFV is a very effective vaccine that elicits an optimal, long-term protective immune response upon administration of a single dose, this model has been used extensively to explore the human immune response to a controlled, self-resolving acute viral infection (reviewed in Ahmed R, Akondy R S. 2011. Insights into human CD8(+) T-cell memory using the yellow fever and smallpox vaccines. Immunol Cell Biol 89: 340-345, and Pulendran B. 2009. Learning immunology from the yellow fever vaccine: innate immunity to systems vaccinology. Nat Rev Immunol 9:741-747). These seminal studies have shown that (i) the ability of YF-17D to infect dendritic cells and signal through multiple Toll-like receptors may be related to the effectiveness of this vaccine (Querec T, et al. 2006. Yellow fever vaccine YF-17D activates multiple dendritic cell subsets via TLR2, 7, 8, and 9 to stimulate polyvalent immunity. J Exp Med 203:413-424.); (ii) neutralizing antibodies (nAbs) are the best surrogate marker for protection against YFV and remain detectable for many years (Jonker E F, et al. 2013. Advances and controversies in yellow fever vaccination. Ther Adv Vaccines 1:144-152; Reinhardt B, et al. 1998. Development of viremia and humoral and cellular parameters of immune activation after vaccination with yellow fever virus strain 17D: a model of human flavivirus infection. J Med Virol 56:159-167.); and (iii) CD8+ T cells expand massively before nAbs can be detected (and are thus likely involved in the control of viremia) and persist in the memory compartment for decades (Miller J D, et al. 2008. Human effector and memory CD8+ T cell responses to smallpox and yellow fever vaccines. Immunity 28:710-722; Santos A P, et al. 2005. Lymphocyte subset analyses in healthy adults vaccinated with yellow fever 17DD virus. Mem Inst Oswaldo Cruz 100:331-337.).

The current understanding of the CD4+ response to YFV, however, is limited. Although helper T cells are clearly required for the production of YFV-specific Abs (including nAbs), different studies have reported variable levels of induction of CD4+ T cells upon vaccination with YFV (Santos et al. 2005; Kohler S, et al. 2012. The early cellular signatures of protective immunity induced by live viral vaccination. Eur J Immunol 42:2363-2373.). Some analyses have revealed that cytokine producing YFV-specific CD4+ T cells can be detected as early as day 2 post-vaccination and that they return to baseline by day 28, suggesting that the kinetics of CD4+ T cells precede those of CD8+ T cells (Blom K, et al. 2013. Temporal dynamics of the primary human T cell response to yellow fever virus 17D as it matures from an effector- to a memory-type response. J Immunol 190: 2150-2158; Kohler et al. 2012). Recently, James et al. used class II HLA-DR restricted, YFV-specific tetramers to characterize the CD4+ response to YFV in more depth, showing that all 10 proteins in the YFV genome contain antigenic epitopes recognized by CD4+ T cells (James E A, LaFond R E, Gates T J, Mai D T, Malhotra U, Kwok W W. 2013. Yellow fever vaccination elicits broad functional CD4+ T cell responses that recognize structural and nonstructural proteins. J Virol 87: 12794-12804.). This study also revealed a wide range of frequencies of CD4+ T cells specific for a limited number of YFV epitopes in peripheral blood (from 0 to 100 cells per million CD4+ T cells) and established that YFV-specific T cells, which display a predominant Th1-like memory phenotype, occur at ~10- to 100-fold higher frequencies in vaccinated versus unvaccinated individuals, depending on the time point considered. Id. In contrast, there have been several detailed analyses of the kinetics and phenotype of CD8+ T cells induced by vaccination with YFV. For example, Miller et al. showed that activated effector CD8+ T cells (TAE) peak 2 weeks after administration of the YFV and defined the YFV-specific subpopulation of CD8+ CTL cells as CD38+ HLA-DR+Ki-67+ Bcl-2$^{lo}$. In addition, this study established a strong correlation between the levels of CD38+ HLA-DR+ CD8+ T cells and the expression of gamma interferon (IFN-γ) by total CD8+ T cells in response to YF virus-infected cells, and it demonstrated that stimulation of CD8+ T cells from YFV-vaccinated volunteers with a comprehensive pool of peptides that span the YF virus polyprotein also induced IFN-γ. Since unrelated memory CD8+ T cells (such as those specific for chronic viruses like Epstein-Barr virus (EBV) and cytomegalovirus (CMV) and therefore presumed to preexist at the time of vaccination with YFV) were not found among the expanded CD8+ T cell population, these observations suggest that, at least in the case of YFV, the bystander effect is minimal, and they also imply that the vast majority of TAE clones observed after administration of YF-17D are YF virus specific. Finally, those authors showed that Ag specific cells could be identified more than 30 days post-vaccination, indicating that the YFV-specific effector CD8+ T cells had waned and also that a certain proportion of them had entered the memory compartment (Miller et al. 2008). Subsequent work from the same group employed an array of overlapping peptides that spanned the entire YF virus polyprotein to demonstrate that vaccination with YFV induces a broad CD8+T response that targets several epitopes in each of the 10 viral proteins (Akondy R S, et al. 2009. The yellow fever virus vaccine induces a broad and polyfunctional human memory CD8+ T cell response. J Immunol 183:7919-7930.). The use of tetramers carrying an immunodominant epitope from the nonstructural NS4b protein helped define the phenotypes of YFV-specific CD8+ T cells through the expansion, contraction, and memory phases of the immune response, further confirming that CD38+ HLA-DR+CD8+ T cells dramatically expand after YFV-17D administration and produce cytotoxic effector molecules. Id. Similar results were observed by Co et al., who identified YFV-specific proliferation and cytolytic responses on day 14 postvaccination and isolated CD8+ T cell lines that were specific for epitopes from structural and nonstructural YF virus proteins, some of which persisted for up to 19 months postvaccination (Co M D, Terajima M, Cruz J, Ennis F A, Rothman A L. 2002. Human cytotoxic T lymphocyte responses to live attenuated 17D yellow fever vaccine: identification of HLA-B35-restricted CTL epitopes on nonstructural proteins NS1, NS2b, NS3, and the structural protein E. Virology 293:151-163. Again, follow-up data from a tetramer-based approach showed that YFV-specific CD8+ T cells could be identified as early as 7 to 9 days post-vaccination, before IFN-γ production was detectable, that memory cells corresponded mostly to a differentiated effector phenotype (CD45RA$^+$ CCR7-CD62L−), and that these peptide-specific responses lasted for at least 54 months (Co M D, et al. 2009. Dynamics of the CD8 T-cell response following yellow fever virus 17D immunization. Immunology 128:e718-e727.). A more recent study using a limited set of YF virus HLA-tetramer epitopes suggested that the CD8+ response to YFV is broad and complex and that responses to different epitopes vary in magnitude and duration (Blom K, et al. 2013. Temporal dynamics of the primary human T cell response to yellow fever virus 17D as it matures from an effector- to a memory-type response. J Immunol 190: 2150-2158). Those authors also found that YFV-specific effector CD8+ T cells were CD45RA$^{hi}$ CCR7-PD1-CD27$^{hi}$ and that only some of these cells transition to the T cell memory compartment, at which point they became CD45RA+ CCR7-PD1-CD27$^{lo}$ (Blom et al. 2013, Journal of Immunology 190:2150-2158).

Thus, it is essential to characterize the dynamics of the B cell and T cell repertoires in response to an infection to determine the breadth of the immune response, to characterize the formation of immunological memory, and to understand how the human immune system responds to infection or vaccination. The present disclosure addresses these needs and more.

BRIEF SUMMARY OF THE INVENTION

One aspect of the invention provides a method of measuring T cell response to a vaccine in a subject, comprising: performing high-throughput sequencing of nucleic acid molecules comprising rearranged CDR3 regions of TCR loci obtained from a first biological sample of the subject at a first time point prior to vaccination; performing high-throughput sequencing of nucleic acid molecules comprising rearranged CDR3 regions of TCR loci obtained from a second biological sample of the subject at a second time point post vaccination; and identifying T cell clones having CDR3 regions of significantly higher proportional abundance in the second biological sample in comparison to the first biological sample, thereby identifying vaccine-induced responsive clones.

In one embodiment, the TCR loci are selected from the group consisting of the TCR$\alpha$ locus, TCR$\beta$ locus, TCR$\gamma$ locus, and TCR$\delta$ locus. In one embodiment, the biological samples comprise peripheral blood mononuclear cells (PBMCs). In certain embodiments, the biological samples comprise memory T cells. In one embodiment, the second biological sample is obtained at least 10 days post vaccination.

In another embodiment, the method further comprises performing multiplex PCR amplification of genomic templates comprising rearranged CDR3 regions to produce nucleic acid molecules for sequencing. In one embodiment, identifying comprises calculating a false discovery rate, and wherein the calculating comprises performing a computation on a computer.

In one embodiment, the activated T cell clones are vaccine antigen-specific T cells. In another embodiment, the activated T cell clones are CD8$^+$ effector T cells.

In one embodiment, the vaccine is a vaccine for an infectious agent or a cancer vaccine. In a related embodiment, the infectious agent is a virus selected from the group consisting of yellow fever virus, influenza virus, smallpox virus, herpes simplex virus, cytomegalovirus, Epstein-barr virus and human papilloma virus.

In another embodiment, the method further comprises sorting the activated T cell clones in the second biological sample by flow cytometry. In one embodiment, the method further comprises sorting the first biological sample for memory T cells using flow cytometry.

In a related aspect, the method of measuring T cell response to a vaccine in a subject further comprises: performing high-throughput sequencing of nucleic acid molecules comprising rearranged CDR3 regions of TCR loci obtained from a third biological sample of the subject at a third time point post vaccination; and identifying newly recruited memory T cell clones corresponding to the vaccine-induced responsive clones that are not present in the first biological sample and that have been recruited to a memory T cell population post vaccination.

In one embodiment, the identifying newly recruited memory T cell clones comprises sorting memory T cells by flow cytometry. In another embodiment, identifying newly recruited memory T cell clones comprises comparing a first set of memory T cell clones in the first biological sample to a second set of memory T cell clones in the third biological sample to identify one or more newly recruited memory T cell clones that have been recruited to the memory T cell population post vaccination. In a related embodiment, the method further comprises comparing the identified one or more newly recruited memory T cell clones with one or more vaccine-induced responsive clones from the second biological sample to find matches between the newly recruited memory T cell clones and the one or more vaccine-induced responsive clones. In one embodiment, the matched memory T cell clones are a significant proportion of total memory T cell population and are identified as biomarkers for vaccine-specific response. In one embodiment, the memory T cell clones are CD8$^+$CD45RO$^+$CD62L$^{lo}$ effector memory T cells. In another embodiment, the memory T cell clones are CD8$^+$CD45RO$^+$CD62L$^{hi}$ central memory T cells. In one embodiment, the third time point is at least 30 days post vaccination.

In certain embodiments, the method does not require an enrichment step by sorting for effector cells with flow cytometry. In one embodiment, a degree of recruitment of vaccine-induced responsive clones to immunological memory is identified as a biomarker for vaccine efficacy.

Another aspect of the invention provides a method of measuring T cell response to a vaccine in a subject, comprising: performing high-throughput sequencing of nucleic acid molecules comprising rearranged CDR3 regions of TCR loci obtained from a first biological sample of the subject at a first time point post vaccination; sorting activated T cells from a subset of the first biological sample using flow cytometry to generate a set of activated T cells; performing high-throughput sequencing of nucleic acid molecules comprising rearranged CDR3 regions of TCR loci obtained from the set of activated T cells; and identifying activated T cell clones in the set having CDR3 regions of significantly higher proportional abundance in the activated T cell population in comparison to the first biological sample, thereby identifying vaccine-induced responsive clones.

In one embodiment, the TCR loci are selected from the group consisting of the TCR$\alpha$ locus, TCR$\beta$ locus, TCR$\gamma$ locus, and TCR$\delta$ locus. In another embodiment, the biological samples comprise peripheral blood mononuclear cells (PBMCs). In one embodiment, the biological samples comprise memory T cells. In another embodiment, the first biological sample is obtained at least 10 days post vaccination. In one embodiment, the method further comprises performing multiplex PCR amplification of genomic templates comprising rearranged CDR3 regions to produce nucleic acid molecules for sequencing. In another embodiment, identifying comprises calculating a false discovery rate, and wherein the calculating comprises performing a computation on a computer.

In one embodiment, the activated T cell clones are vaccine antigen-specific T cells. In another embodiment, the activated T cell clones are CD8$^+$ effector T cells. In one embodiment, the vaccine is a vaccine for an infectious agent or a cancer vaccine.

In a related aspect, the method of measuring T cell response to a vaccine in a subject further comprises: performing high-throughput sequencing of nucleic acid molecules comprising rearranged CDR3 regions of TCR loci obtained from a second biological sample of the subject at a second time point post vaccination; and identifying newly recruited memory T cell clones corresponding to the vaccine-induced responsive clones that have been recruited to a memory T cell population post vaccination.

In one embodiment, identifying newly recruited memory T cell clones comprises sorting memory T cells by flow cytometry. In another embodiment, identifying newly recruited memory T cell clones comprises comparing a first set of memory T cell clones in the first biological sample to a second set of memory T cell clones in the second biological sample to identify one or more newly recruited memory T cell clones that have been recruited to the memory T cell population post vaccination. In one embodiment, the method further comprises comparing the identified one or more newly recruited memory T cell clones with one or more vaccine-induced responsive clones from the set of activated T cells to find matches between the newly recruited memory T cell clones and the one or more vaccine-induced responsive clones. In a related embodiment, the matched memory T cell clones are a significant number of the vaccine-induced responsive clones and are identified as biomarkers for vaccine-specific response. In another embodiment, the matched memory T cell clones are a significant proportion of total memory T cell population and are identified as biomarkers for vaccine-specific response.

In one embodiment, the memory T cell clones are $CD8^+CD45RO^+CD62L^{lo}$ effector memory T cells. In another embodiment, the memory T cell clones are $CD8^+CD45RO^+CD62L^{hi}$ central memory T cells. In one embodiment, the second time point is at least 30 days post vaccination.

One aspect of the invention provides a method for determining the effectiveness of a vaccine comprising: performing high-throughput sequencing of nucleic acid molecules comprising rearranged CDR3 regions of TCR loci obtained from a first biological sample of the subject at a first time point prior to vaccination; performing high-throughput sequencing of nucleic acid molecules comprising rearranged CDR3 regions of TCR loci obtained from a second biological sample of the subject at a second time point post vaccination; identifying T cell clones having CDR3 regions of significantly higher proportional abundance in the second biological sample in comparison to the first biological sample, thereby identifying vaccine-induced responsive clones; performing high-throughput sequencing of nucleic acid molecules comprising rearranged CDR3 regions of TCR loci obtained from a third biological sample of the subject at a third time point post vaccination; identifying newly recruited memory T cell clones corresponding to the vaccine-induced responsive clones that have been recruited to a memory T cell population post vaccination; and comparing a degree of recruitment of vaccine-induced responsive clones to immunological memory to a reference degree of recruitment, wherein the vaccine is effective when the degree of recruitment is greater than or equal to the reference degree of recruitment.

In one embodiment, identifying newly recruited memory T cell clones comprises comparing the identified one or more newly recruited memory T cell clones with one or more vaccine-induced responsive clones from the second biological sample to find matches between the newly recruited memory T cell clones and the one or more vaccine-specific responsive clones. In another embodiment, the degree of recruitment is a percentage of vaccine-induced responsive clones that match newly recruited memory T cell clones. In one embodiment, the reference degree of recruitment is a degree of recruitment following a candidate vaccine. In another embodiment, the reference degree of recruitment is a degree of recruitment following a reference vaccine. In one embodiment, the reference degree of recruitment is a degree of recruitment following an infection.

Another aspect of the invention provides a method of measuring a T cell response to an infection in a subject, comprising: performing high-throughput sequencing of nucleic acid molecules comprising rearranged CDR3 regions of TCR loci obtained from a first biological sample of the subject at a first time point prior to infection; performing high-throughput sequencing of nucleic acid molecules comprising rearranged CDR3 regions of TCR loci obtained from a second biological sample of the subject at a second time point after infection; and identifying T cell clones having CDR3 regions of significantly higher proportional abundance in the second biological sample in comparison to the first biological sample, thereby identifying infection-induced responsive clones.

In one embodiment, the method of measuring a T cell response to an infection further comprises: performing high-throughput sequencing of nucleic acid molecules comprising rearranged CDR3 regions of TCR loci obtained from a third biological sample of the subject at a third time point post infection; and identifying newly recruited memory T cell clones corresponding to the infection-induced responsive clones that are not present in the first biological sample and that have been recruited to a memory T cell population post infection.

In one embodiment, identifying newly recruited memory T cell clones comprises comparing a first set of memory T cell clones in the first biological sample to a second set of memory T cell clones in the second biological sample to identify one or more newly recruited memory T cell clones that have been recruited to the memory T cell population post infection. In another embodiment, the infection is selected from the group consisting of viral infection, bacterial infection, and parasitic infection. In a related embodiment, the viral infection is an acute viral infection.

One aspect of the invention provides a method of measuring a T cell response to an infection in a subject, comprising: performing high-throughput sequencing of nucleic acid molecules comprising rearranged CDR3 regions of TCR loci obtained from a first biological sample of the subject at a first time point post infection; sorting activated T cells from a subset of the first biological sample using flow cytometry to generate a set of activated T cells; performing high-throughput sequencing of nucleic acid molecules comprising rearranged CDR3 regions of TCR loci obtained from the set of activated T cells; and identifying activated T cell clones in the set having CDR3 regions of significantly higher proportional abundance in the activated T cell population in comparison to the first biological sample, thereby identifying infection-induced responsive clones.

In one embodiment, the method of measuring a T cell response to an infection further comprises: performing high-throughput sequencing of nucleic acid molecules comprising rearranged CDR3 regions of TCR loci obtained from a second biological sample of the subject at a second time point post infection; and identifying newly recruited memory T cell clones corresponding to the infection-induced responsive clones that are not present in the first biological sample and that have been recruited to a memory T cell population post infection. In one embodiment, identifying newly recruited memory T cell clones comprises comparing a first set of memory T cell clones in the first biological sample to a second set of memory T cell clones in the second biological sample to identify one or more newly recruited memory T cell clones that have been recruited to the memory T cell population post infection. In another embodiment, the infection is selected from the group consisting of viral infection, bacterial infection, and parasitic infection. In a related embodiment, the viral infection is an acute viral infection.

Another aspect of the invention provides a method for measuring B cell response to a vaccine in a subject, comprising: performing high-throughput sequencing of nucleic acid molecules comprising rearranged CDR3 regions of immunoglobulin (Ig) loci obtained from a first biological sample of the subject at a first time point prior to vaccination; performing high-throughput sequencing of nucleic acid molecules comprising rearranged CDR3 regions of Ig loci obtained from a second biological sample of the subject at a second time point post vaccination; clustering groups of CDR3 sequences of common descent comprising clones having undergone somatic hypermutation, wherein said clustering employs a clustering algorithm using a string distance metric; and identifying B cell clones having CDR3 sequence clusters of significantly higher proportional abundance in the second biological sample in comparison to the first biological sample, thereby identifying vaccine-induced responsive clones.

In one embodiment, the Ig loci are selected from the group consisting of the Ig heavy chain (IGH) locus, Ig kappa light chain (IGK) locus, and Ig lambda light chain (IGL) locus. In another embodiment, the biological samples comprise PBMCs. In one embodiment, the biological samples comprise memory B cells. In another embodiment, the second biological sample is obtained at least 1 day post vaccination.

In one embodiment, the high-throughput sequencing comprises multiplex PCR amplification of the nucleic acid molecules comprising rearranged CDR3 regions. In another embodiment, identifying comprises calculating a false discovery rate, and wherein the calculating comprises performing a computation on a computer.

In one embodiment, the activated B cell clones are vaccine antigen-specific B cells. In another embodiment, the vaccine is a vaccine for an infectious agent or a cancer vaccine.

In a related aspect, the method of measuring B cell response to a vaccine further comprises: performing high-throughput sequencing of nucleic acid molecules comprising rearranged CDR3 regions of Ig loci obtained from a third biological sample of the subject at a third time point post vaccination; and identifying newly recruited memory B cell clones corresponding to the vaccine-induced responsive clones that are not present in the first biological sample and have been recruited to a memory B cell population post vaccination.

In one embodiment, identifying comprises sorting memory B cells by flow cytometry. In another embodiment, identifying comprises comparing a first set of memory B cell clones in the first biological sample to a second set of memory B cell clones in the third biological sample to identify one or more newly recruited memory B cell clones that have been recruited to the memory B cell population post vaccination.

One embodiment further comprises comparing the identified one or more newly recruited memory B cell clones with one or more vaccine-induced responsive clones from the second biological sample to find matches between the newly recruited memory B cell clones and the one or more vaccine-induced responsive clones. In another embodiment, the matched memory B cell clones are identified as biomarkers for vaccine-specific response.

In one embodiment, the memory B cell clones are $CD19^+$ $CD20^+CD38^-CD40^+$ memory B cells. In another embodiment, the memory B cell clones are non-switched memory B cells. In one embodiment, the memory B cell clones are switched memory B cells. In a related embodiment, the switched memory B cells are $IgG^+$.

One aspect of the invention provides a method of measuring B cell response to a vaccine in a subject, comprising: performing high-throughput sequencing of nucleic acid molecules comprising rearranged CDR3 regions of Ig loci obtained from a first biological sample of the subject at a first time point post vaccination; sorting activated B cells from a subset of the first biological sample using flow cytometry to generate a set of activated B cells; performing high-throughput sequencing of nucleic acid molecules comprising rearranged CDR3 regions of Ig loci obtained from the set of activated B cells; clustering groups of CDR3 sequences of common descent comprising clones having undergone somatic hypermutation, wherein said clustering employs a clustering algorithm using a string distance metric; and identifying activated B cell clones in the set having CDR3 sequence clusters of significantly higher proportional abundance in the activated B cell population in comparison to the first biological sample, thereby identifying vaccine-induced responsive clones.

In one embodiment, the Ig loci are selected from the group consisting of the IGH locus, IGK locus, and IGL locus. In another embodiment, the biological samples comprise peripheral blood mononuclear cells (PBMCs). In one embodiment, the biological samples comprise memory B cells. In another embodiment, the first biological sample is obtained at least 1 day post vaccination.

In one embodiment, the method of measuring B cell response to a vaccine further comprises performing multiplex PCR amplification of genomic templates comprising rearranged CDR3 regions to produce nucleic acid molecules for sequencing. In another embodiment, identifying comprises calculating a false discovery rate, and wherein the calculating comprises performing a computation on a computer.

In one embodiment, the activated B cell clones are vaccine antigen-specific B cells. In another embodiment, the vaccine is a vaccine for an infectious agent or a cancer vaccine.

In a related aspect, the method of measuring B cell response to a vaccine further comprises: performing high-throughput sequencing of nucleic acid molecules comprising rearranged CDR3 regions of Ig loci obtained from a second biological sample of the subject at a second time point post vaccination; and identifying newly recruited memory B cell clones corresponding to the vaccine-induced responsive clones that have been recruited to a memory B cell population post vaccination.

In one embodiment, the identifying newly recruited memory B cell clones comprises sorting memory B cells by flow cytometry. In another embodiment, identifying newly recruited memory B cell clones comprises comparing a first set of memory B cell clones in the first biological sample to a second set of memory B cell clones in the second biological sample to identify one or more newly recruited memory B cell clones that have been recruited to the memory B cell population post vaccination. In another embodiment, the method further comprises comparing the identified one or more newly recruited memory B cell clones with one or more vaccine-induced responsive clones from the set of activated B cells to find matches between the newly recruited memory B cell clones and the one or more vaccine-induced responsive clones. In a related embodiment, the matched memory B cell clones are a significant number of the vaccine-induced responsive clones and are identified as biomarkers for vaccine-specific response. In another embodiment, the matched memory B cell clones are a significant proportion of total memory B cell population and are identified as biomarkers for vaccine-specific response. In one embodiment, the second time point is at least 30 days post vaccination.

Another aspect of the invention provides a method for determining the effectiveness of a vaccine comprising: performing high-throughput sequencing of nucleic acid molecules comprising rearranged CDR3 regions of immunoglobulin (Ig) loci obtained from a first biological sample of the subject at a first time point prior to vaccination; performing high-throughput sequencing of nucleic acid molecules comprising rearranged CDR3 regions of Ig loci obtained from a second biological sample of the subject at a second time point post vaccination; clustering groups of CDR3 sequences of common descent comprising clones having undergone somatic hypermutation, wherein said clustering employs a clustering algorithm using a string distance metric; and identifying B cell clones having CDR3 sequence clusters of significantly higher proportional abundance in the second biological sample in comparison to the first biological sample, thereby identifying vaccine-induced responsive clones; performing high-throughput sequencing of nucleic acid molecules comprising rearranged CDR3 regions of Ig loci obtained from a third biological sample of the subject at a third time point post vaccination; identifying newly recruited memory B cell clones corresponding to the vaccine-induced responsive clones that are not present in the first biological sample and have been recruited to a memory B cell population post vaccination; and comparing a degree of recruitment of vaccine-induced responsive clones to immunological memory to a reference degree of recruitment, wherein the vaccine is effective when the degree of recruitment is greater than or equal to the reference degree of recruitment.

In one embodiment, identifying comprises comparing the identified one or more newly recruited memory B cell clones with one or more vaccine-induced responsive clones from the second biological sample to find matches between the newly recruited memory B cell clones and the one or more vaccine-specific responsive clones. In another embodiment, the degree of recruitment is a percentage of vaccine-induced responsive clones that match newly recruited memory B cell clones. In one embodiment, the reference degree of recruitment is a degree of recruitment following a candidate vaccine. In another embodiment, the reference degree of recruitment is a degree of recruitment following a reference vaccine. In one embodiment, the reference degree of recruitment is a degree of recruitment following an infection.

One aspect of the invention provides a method of measuring a B cell response to an infection in a subject, comprising: performing high-throughput sequencing of nucleic acid molecules comprising rearranged CDR3 regions of immunoglobulin (Ig) loci obtained from a first biological sample of the subject at a first time point prior to infection; performing high-throughput sequencing of nucleic acid molecules comprising rearranged CDR3 regions of Ig loci obtained from a second biological sample of the subject at a second time point post infection; clustering groups of CDR3 sequences of common descent comprising clones having undergone somatic hypermutation, wherein said clustering employs a clustering algorithm using a string distance metric; and identifying B cell clones having CDR3 sequence clusters of significantly higher proportional abundance in the second biological sample in comparison to the first biological sample, thereby identifying vaccine-induced responsive clones.

In one embodiment, the method further comprises: performing high-throughput sequencing of nucleic acid molecules comprising rearranged CDR3 regions of Ig loci obtained from a third biological sample of the subject at a third time point post infection; and identifying newly recruited memory B cell clones corresponding to the infection-induced responsive clones that are not present in the first biological sample and have been recruited to a memory B cell population post infection. In one embodiment, identifying newly recruited memory B cell clones comprises comparing a first set of memory B cell clones in the first biological sample to a second set of memory B cell clones in the second biological sample to identify one or more newly recruited memory T cell clones that have been recruited to the memory B cell population post infection. In another embodiment, the infection is selected from the group consisting of viral infection, bacterial infection, and parasitic infection. In a related embodiment, the viral infection is an acute viral infection.

Another aspect of the invention provides a method of measuring B cell response to an acute viral infection in a subject, comprising: performing high-throughput sequencing of nucleic acid molecules comprising rearranged CDR3 regions of Ig loci obtained from a first biological sample of the subject at a first time point post infection; sorting activated B cells from a subset of the first biological sample using flow cytometry to generate a set of activated B cells; performing high-throughput sequencing of nucleic acid molecules comprising rearranged CDR3 regions of Ig loci obtained from the set of activated B cells; clustering groups of CDR3 sequences of common descent comprising clones having undergone somatic hypermutation, wherein said clustering employs a clustering algorithm using a string distance metric; and identifying activated B cell clones having CDR3 sequence clusters of significantly higher proportional abundance in the activated B cell population in comparison to the first biological sample, thereby identifying infection-induced responsive clones.

In one embodiment, the method further comprises: performing high-throughput sequencing of nucleic acid molecules comprising rearranged CDR3 regions of Ig loci obtained from a second biological sample of the subject at a second time point post infection; and identifying newly recruited memory B cell clones corresponding to the infection-induced responsive clones that have been recruited to a memory B cell population post infection. In another embodiment, identifying newly recruited memory B cell clones comprises comparing a first set of memory B cell clones in the first biological sample to a second set of memory B cell clones in the third biological sample to identify one or more newly recruited memory B cell clones that have been recruited to the memory B cell population post infection. In one embodiment, the infection is selected from the group consisting of viral infection, bacterial infection, and parasitic infection. In a related embodiment, the viral infection is an acute viral infection.

BRIEF DESCRIPTION OF THE DRAWINGS

FIG. 1A shows the number of clones classified as YFV induced for various FDR significance thresholds for all subjects. By examining the number of significant tests at various Q value thresholds (FDR thresholds), an appropriate threshold can be selected. Here, a threshold of 0.01 was selected. FIG. 1B shows the number of clones classified as putatively reactive clones for various FDR significance thresholds for all subjects. A threshold of 0.05 was selected. Each subject is represented by a different tone of gray, as indicated in the legend.

FIGS. 2A-2E show the identification of YFV-induced clones. FIG. 2A shows a graph of the abundance of unique clones identified by statistical enrichment on the activated effector CD38+ HLA-DR+CD8+ T cell compartment on day 14 post-vaccination (TAE-14) versus those present in the corresponding total PBMC sample from the same time point for subject 1. FIGS. 2B-2E show the same for subjects 2 to 9. Clones were classified into four categories based both on their presence in the TAE-14 and the TM-0 compartments. Red clones are present in the TAE-14 compartment, whereas gray clones are not; while clones absent in the TM-0 compartment have a black edge and those present in the TM-0 compartment do not. Darker colors indicate that multiple data points have been superimposed in that particular position. Regions bound by dashed lines indicate clones present in only one sample. YFV-induced clones were significantly enriched in the CD38+ HLA-DR+CD8+ T cell-sorted population compared to the corresponding total PBMC sample.

FIG. 3A shows the efficiency of recruitment of YFV-induced clones to the effector (TEM+ TCM−) and central (TEM− TCM+) memory compartments, or both (TEM+ TCM+) as a percentage of all clones classified as YFV induced. FIG. 3A shows that, respectively, 3.1% and 2.5% of YFV-induced clones absent in $T_{M0}$ were identified exclusively in the $T_{EM}$ or the $T_{CM}$ compartments, while 6.7% were identified in both.

FIGS. 5B-5E show the same for subjects 2 to 9. Significant enrichment (or expansion) was defined based on a q value threshold, with 1% and 5% expected false-positive rates for YFV-induced and putatively reactive clones, respectively, as described above. Clones were classified into four categories based both on their presence in the TAE-14 and the TM-0 compartments, as indicated in the legend. Darker colors indicate that multiple data points are superimposed in that particular position. Regions bound by dashed lines indicate clones present in only one sample.

DETAILED DESCRIPTION

Figure 1:
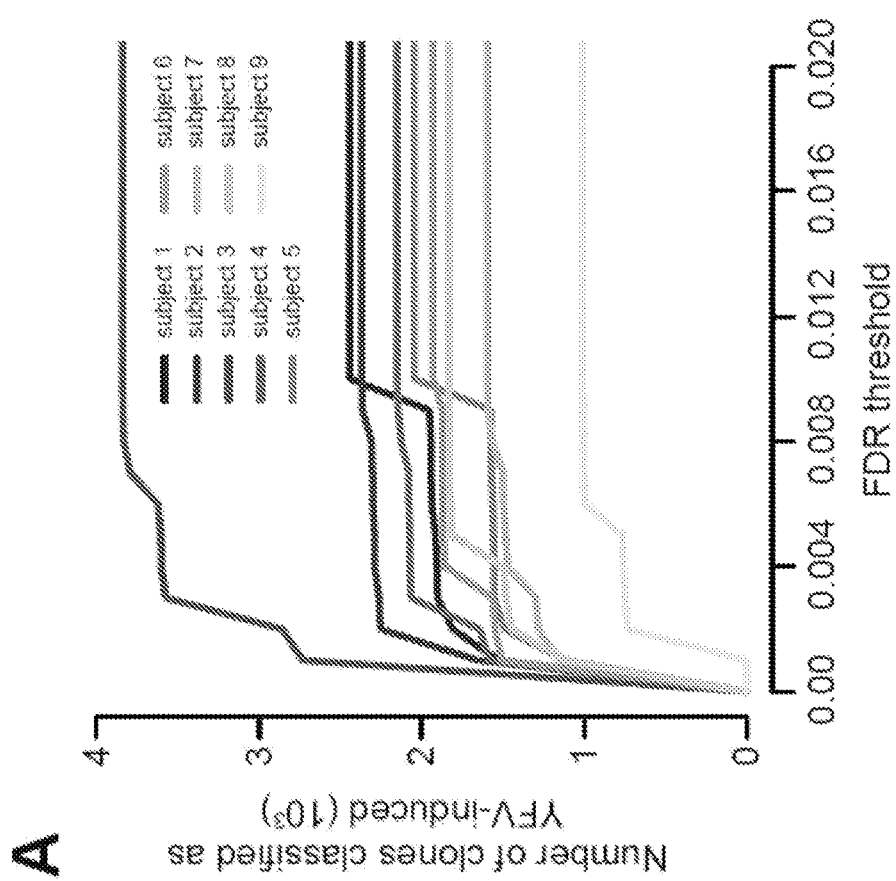
FIG. 1A and FIG. 1B show data used for selection of FDR thresholds.

The present disclosure relates to in-depth analysis of the dynamics of T cell and B cell repertoires before, during, and after an infection. A vaccination model is used to understand the adaptive immune response to a viral infection. The in-depth analysis provides methods for characterizing the adaptive immune response to an infection or vaccination by identification and enumeration of unique T cell and B cell clones specifically induced by the vaccination or infection through a combined experimental and bioinformatics approach. The methods described herein can be used to identify responsive T cell and B cell clones and to further identify which responding clones were recruited to immunological memory. The methods described herein provide certain advantages, including, e.g., the capability to identify responding clones utilizing high throughput sequencing without first enriching the cell population (e.g., sorting using flow cytometry). Additionally, particular methods described herein provide for the identification of responding clones using only a single time point after vaccination or infection.

Recruitment of T cell or B cell clones to immunological memory can be defined as a number of infection-induced T cell or B cell clones that are identified as memory cells at a time point after infection (or vaccination) and were not found in memory at an earlier time point.

These methods apply to analyzing the adaptive immune response for various types of infections, for example, infection caused by a foreign pathogen, such as a virus, bacteria, or parasite. The infection can be an acute viral infection. An acute viral infection is characterized by rapid onset of disease, a relatively brief period of symptoms, and resolution within days. It is usually accompanied by early production of infectious virions and elimination of infection by the host immune system. In some embodiments, the infection is a chronic viral infection.

Definitions

Terms used in the claims and specification are defined as set forth below unless otherwise specified.

As used herein, adaptive immune receptor (AIR) refers to an immune cell receptor, e.g., a T cell receptor (TCR) or an Immunoglobulin (Ig) receptor found in mammalian cells. In certain embodiments, the adaptive immune receptor is encoded by a TCRB, TCRG, TCRA, TCRD, IGH, IGK, and IGL gene or gene segment.

The term "primer," as used herein, refers to an oligonucleotide sequence capable of acting as a point of initiation of DNA synthesis under suitable conditions. A primer is complementary to (or hybridizes to) a target template (e.g., DNA, cDNA or mRNA template). Such conditions include those in which synthesis of a primer extension product complementary to a nucleic acid strand is induced in the presence of four different nucleoside triphosphates and an agent for extension (e.g., a DNA polymerase or reverse transcriptase) in an appropriate buffer and at a suitable temperature.

In some embodiments, as used herein, the term "gene" refers to the segment of DNA involved in producing a polypeptide chain, such as all or a portion of a TCR or Ig polypeptide (e.g., a CDR3-containing polypeptide); it includes regions preceding and following the coding region "leader and trailer" as well as intervening sequences (introns) between individual coding segments (exons), regulatory elements (e.g., promoters, enhancers, repressor binding sites and the like), or recombination signal sequences (RSSs), as described herein.

The nucleic acids of the present embodiments, also referred to herein as polynucleotides, and including oligonucleotides, can be in the form of RNA or in the form of DNA, including cDNA, genomic DNA, and synthetic DNA. The DNA can be double-stranded or single-stranded, and if single stranded can be the coding strand or non-coding (anti-sense) strand. A coding sequence which encodes a TCR or an Ig or a region thereof (e.g., a V region, a D segment, a J region, a C region, etc.) for use according to the present embodiments can be identical to the coding sequence known in the art for any given TCR or immunoglobulin gene regions or polypeptide domains (e.g., V-region domains, CDR3 domains, etc.), or can be a different coding sequence, which as a result of the redundancy or degeneracy of the genetic code, encodes the same TCR or immunoglobulin region or polypeptide.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques can be used for recombinant technology, molecular biological, microbiological, chemical syntheses, chemical analyses, pharmaceutical preparation, formulation, and delivery, and treatment of patients.

Unless the context requires otherwise, throughout the present specification and claims, the word "comprise" and variations thereof, such as, "comprises" and "comprising" are to be construed in an open, inclusive sense, that is, as "including, but not limited to." By "consisting of" is meant including, and typically limited to, whatever follows the phrase "consisting of." By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and can or cannot be present depending upon whether or not they affect the activity or action of the listed elements.

It must be noted that, as used in the specification and the appended claims, the singular forms "a," "an" and "the" include plural referents unless the context clearly dictates otherwise.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

Cells

The sample can include T cells and/or B cells. T cells (T lymphocytes) include, for example, cells that express T cell receptors. T cells include Helper T cells (effector T cells or Th cells), cytotoxic T cells (CTLs), memory T cells, and regulatory T cells. The sample can include a single cell in some applications or more generally at least 1,000, at least 10,000, at least 100,000, at least 250,000, at least 500,000, at least 750,000, at least 1,000,000 T cells, or at least 10,000,000 T cells.

B cells include, for example, plasma B cells, memory B cells, B1 cells, B2 cells, marginal-zone B cells, and follicular B cells. B cells can express immunoglobulins (antibodies, B cell receptor). The sample can include a single cell in some applications or more generally at least 1,000, at least 10,000, at least 100,000, at least 250,000, at least 500,000, at least 750,000, at least 1,000,000 B-cells, or at least 10,000,000 B cells.

The sample can include nucleic acid molecules such as DNA (e.g., genomic DNA or mitochondrial DNA) or RNA (e.g., messenger RNA or microRNA) or cDNA (complementary DNA). In some embodiments, the nucleic acid is cell-free DNA. In other embodiments, the sample is a formalin fixed paraffin embedded tissue.

B cells and T cells can be obtained from a variety of tissue samples including marrow, thymus, lymph glands, peripheral tissues, solid tumors, and blood. Peripheral blood is most easily accessed. Peripheral blood samples are obtained by phlebotomy from subjects. Peripheral blood mononuclear cells (PBMCs) are isolated by techniques known to those of skill in the art, e.g., by Ficoll-Hypaque® density gradient separation. In one embodiment, whole PBMCs are used for analysis.

In one embodiment, the B cells and/or T cells are sorted from the sample into separate populations prior to sequencing. For example, T cells may be separated from non-T cells, and B cells may be separated from non-B cells. PBMCs are referred to herein for illustrative purposes as the sample from which particular cell populations are sorted, however the cells may be sorted in a similar fashion from other types of biological samples. In one embodiment, memory T cells are sorted from PBMCs. In a particular embodiment, central memory T cells are sorted from PBMCs. In another embodiment, effector memory T cells are sorted from PBMCs. In one embodiment, activated effector T cells are sorted from PBMCs. In a particular embodiment, memory T cells and activated effector T cells are sorted from the same PBMC sample. In one embodiment, $CD4^+$ T cells are sorted from PBMCs. In another embodiment, $CD8^+$ T cells are sorted from PBMCs. In another embodiment, memory B cells are sorted from PBMCs. In one embodiment, activated, antibody-producing B cells are sorted from PBMCs. In one embodiment, switched memory B cells (e.g., $IgM^- IgD^-$) are sorted from PBMCs. In another embodiment, non-switched memory B cells (e.g., $IgM^+$ or $IgD^+$) are sorted from PBMCs. In a particular embodiment, memory B cells and activated B cells are sorted from the same PBMC sample. In one embodiment, PBMCs remaining after sorting out one or more populations, or cell types, are a distinct cell population.

Various cell populations may be sorted, or separated, from other cell types using any of a variety of techniques known in art including, e.g., flow cytometry sorting and magnetic bead separation. These techniques often distinguish between different cell types and states of activation based upon markers, such as cell surface markers. In one embodiment, memory B cells are $CD19^+CD20^+CD38^-CD40^+$ cells. In one embodiment, activated effector T cells are identified as $CD38^+HLA-DR^+$. In one embodiment, memory T cells are identified as $CD45RA^-CD45RO^+$. In one embodiment, effector memory T cells are identified as $CD45RA^-CD45RO^+CD62L^{lo}$. In one embodiment, central memory T cells are identified as $CD45RA^-CD45RO^+CD62^{hi}$.

In one embodiment, T cells may be flow sorted into multiple compartments for each time point: e.g., $CD8^+ CD45RO^{+/-}$ and $CD4^+CD45RO^{+/-}$ using fluorescently labeled anti-human antibodies, e.g., CD4 FITC (clone M-T466, Miltenyi Biotec), CD8 PE (clone RPA-T8, BD Biosciences), CD45RO ECD (clone UCHL-1, Beckman Coulter), and CD45RO APC (clone UCHL-1, BD Biosciences). Staining of total PBMCs may be done with the appropriate combination of antibodies, followed by washing cells before analysis. Lymphocyte subsets can be isolated by FACS sorting, e.g., by a BD FACSAria™ cell-sorting system (BD Biosciences) and by analyzing results with FlowJo software (Treestar Inc.), and also by conceptually similar methods involving specific antibodies immobilized to surfaces or beads.

Nucleic Acid Extraction

Total genomic DNA is extracted from cells using any of a variety of methods known in the art, such as, e.g., by using the QIAamp® DNA blood Mini Kit (QIAGEN®). The approximate mass of a single haploid genome is 3 pg. Preferably, at least 100,000 to 200,000 cells are used for analysis of diversity, i.e., about 0.6 to 1.2 μg DNA from diploid T cells. Using PBMCs as a source, the number of T cells can be estimated to be about 30% of total cells. The number of B cells can also be estimated to be about 30% of total cells in a PBMC preparation.

In other embodiments, the nucleic acid is RNA. The RNA molecules can be transcribed to cDNA using known reverse-transcription kits, such as the SMARTer™ Ultra Low RNA kit for Illumina sequencing (Clontech, Mountain View, Calif.) essentially according to the supplier's instructions.

Immune Repertoire Sequencing (Multiplex PCR and High Throughput Sequencing)

The invention includes using compositions and methods for quantitative detection of sequences of substantially all possible TCR and IG gene rearrangements that can be present in a sample containing lymphoid cell DNA. Amplified nucleic acid molecules comprising rearranged TCR or IG regions obtained from a biological sample are sequenced using high-throughput sequencing. In one embodiment, a multiplex PCR system is used to amplify rearranged TCR or IG loci from genomic DNA as described in U.S. Pub. No. 2010/0330571, filed on Jun. 4, 2010, U.S. Pub. No. 2012/0058902, filed on Aug. 24, 2011, International App. No. PCT/US2013/062925, filed on Oct. 1, 2013, which is each incorporated by reference in its entirety.

In one embodiment, the nucleic acid molecule to be sequenced comprises a TCRα, TCRβ, TCRγ or TCRδ CDR3 region. In a particularly preferred embodiment, the nucleic acid to be sequenced comprises a TCRβ CDR3 region. In one embodiment, the nucleic acid to be sequenced comprises an IgH, Igκ or Igλ CDR3 region. In a particularly preferred embodiment, the nucleic acid to be sequenced comprises an IgH CDR3 region.

In general, a multiplex PCR system may use 2, 3, 4, 5, 6, 7, 8, 9, 10, 11, 12, 13 14, 15, 16, 17, 18, 19, 20, 21, 22, 23, 24, or 25, preferably 26, 27, 28, 29, 30, 31, 32, 33, 34, 35, 36, 37, 38, or 39, most preferably 40, 41, 42, 43, 44, or 45 forward primers. In some embodiments, the forward primer is specific to a sequence corresponding to one or more V region segments. "Specific to" can mean complementary to and/or hybridizes to a target sequence. In other embodiments, there are 3, 4, 5, 6, or 7, preferably 8, 9, 10, 11, 12, 13, 14, 15, 16, 17, 18, 19, 20 or more reverse primers. In some embodiments, the reverse primer is specific to a sequence corresponding to one or more J region segments. Most preferably, there is a single J segment primer that is complementary to each J segment. In another embodiment, there are no consensus J primers.

In certain embodiments, the primers are designed not to cross an intron/exon boundary. The forward primers must preferably anneal to the V segments in a region of relatively strong sequence conservation between V segments so as to maximize the conservation of sequence among these primers. Accordingly, this minimizes the potential for differential annealing properties of each primer, and so that the amplified region between V and J primers contains sufficient TCR V sequence information to identify the specific V gene segment used.

Preferably, the J segment primers hybridize with a conserved element of the J segment, and have similar annealing strength. Most preferably, all J segment primers anneal to the same conserved framework region motif.

The forward and reverse primers can have an adaptor sequence on the 5'-end. In some embodiments, the forward and reverse primers comprise a universal sequencing oligonucleotide on the 5'-ends.

Thermal cycling conditions may follow methods of those skilled in the art. For example, using a PCR Express thermal cycler (Hybaid, Ashford, UK), the following cycling conditions may be used: 1 cycle at 95° C. for 15 minutes, 25 to 40 cycles at 94° C. for 30 seconds, 59° C. for 30 seconds and 72° C. for 1 minute, followed by one cycle at 72° C. for 10 minutes.

In some embodiments, the method provides amplification of substantially all of the rearranged adaptive immune receptor (AIR) sequences in a lymphoid cell and is capable of quantifying the diversity of the TCR or IG repertoire of at least $10^6$, $10^5$, $10^4$, or $10^3$ unique rearranged AIR sequences in a sample.

Multiplex quantitative PCR is described further in Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09.001; Sherwood et al. 2011 *Sci. Translat. Med.* 3:90ra61; U.S. Ser. No. 13/217,126, U.S. Ser. No. 12/794,507, WO/2010/151416, WO/2011/106738 (PCT/US2011/026373), WO2012/027503 (PCT/US2011/049012), U.S. Ser. No. 61/550,311, and U.S. Ser. No. 61/569,118, which are incorporated by reference in their entireties. Exemplary V segment and J segment primers are described in U.S. Ser. No. 13/217,126, U.S. Ser. No. 12/794, 507, WO/2010/151416, WO/2011/106738 (PCT/US2011/026373), WO2012/027503 (PCT/US2011/049012), U.S. Ser. No. 61/550,311, and U.S. Ser. No. 61/569,118, which are incorporated by reference in their entireties.

Single Molecule Labeling

In one embodiment, single molecule barcoding is employed to uniquely label DNA target molecules prior to amplification. The barcode is associated with the DNA target sequence throughout the amplification process. Single molecule barcoding may be used in conjunction with high throughput sequencing. Compositions and methods for uniquely tagging rearranged gene segments encoding a TCR and/or an immunoglobulin are described in International App. Pub. Nos. WO 2013/188831 and WO 2014/145992, each of which is incorporated by reference in its entirety.

For mRNA templates, reverse transcription methods can be used to generate cDNA molecules. In one embodiment, reverse transcription can be performed using the SMARTer™ Ultra Low RNA kit for Illumina sequencing (Clontech, Mountain View, Calif.) essentially according to the supplier's instructions. In one embodiment, mRNA molecules can be amplified in multiple wells.

In some embodiments, the cDNA templates can be amplified using non-multiplexed RACE primers and C segment primers. In other embodiments, a plurality of V segment primers and C segment primers are used to amplify mRNA templates.

In some embodiments, the cDNA molecules undergo an additional PCR amplification with tailing primers to incorporate a barcode sequence and a universal primer sequence. In certain embodiments, the tailing primers include a random oligonucleotide sequence (e.g., 6 or 8 bp random oligonucleotide sequence). The resulting cDNA molecules can include at least one barcode sequence, a random oligonucleotide sequence, and universal primer sequences for use with a sequencer. The cDNA templates can then be pooled and sequenced as described herein.

As noted above, further description for methods of single molecule labeling and amplification of mRNA templates can be found in WO 2013/188831 and WO 2014/145992.

Amplification Bias Control

Multiplex PCR assays can result in a bias in the total numbers of amplicons produced from a sample, given that certain primer sets are more efficient in amplification than others. To overcome the problem of such biased utilization of subpopulations of amplification primers, methods can be used that provide a template composition for standardizing the amplification efficiencies of the members of an oligonucleotide primer set, where the primer set is capable of amplifying rearranged DNA encoding a plurality of adaptive immune receptors (TCR or Ig) in a biological sample that comprises DNA from lymphoid cells.

In some embodiments, a template composition is used to standardize the various amplification efficiencies of the primer sets. The template composition can comprise a plurality of diverse template oligonucleotides of general formula (I):

5'-U1-B1-V-B2-R-J-B3-U2-3'     (I)

The template oligonucleotides can vary in nucleotide sequence considerably from one another as a function of significant sequence variability among the large number of possible TCR or BCR variable (V) and joining (J) region polynucleotides. Sequences of individual template oligonucleotide species can also vary from one another as a function of sequence differences in U1, U2, B (B1, B2 and B3) and R oligonucleotides that are included in a particular template within the diverse plurality of templates.

In certain embodiments, V is a polynucleotide comprising at least 20, 30, 60, 90, 120, 150, 180, or 210, and not more than 1000, 900, 800, 700, 600 or 500 contiguous nucleotides of an adaptive immune receptor variable (V) region encoding gene sequence, or the complement thereof, and in each of the plurality of template oligonucleotide sequences V comprises a unique oligonucleotide sequence.

In some embodiments, J is a polynucleotide comprising at least 15-30, 31-60, 61-90, 91-120, or 120-150, and not more than 600, 500, 400, 300 or 200 contiguous nucleotides of an adaptive immune receptor joining (J) region encoding gene sequence, or the complement thereof, and in each of the plurality of template oligonucleotide sequences J comprises a unique oligonucleotide sequence.

U1 and U2 can be each either nothing or each comprise an oligonucleotide having, independently, a sequence that is selected from (i) a universal adaptor oligonucleotide sequence, and (ii) a sequencing platform-specific oligonucleotide sequence that is linked to and positioned 5' to the universal adaptor oligonucleotide sequence.

B1, B2 and B3 can be each either nothing or each comprise an oligonucleotide B that comprises a first and a second oligonucleotide barcode sequence, wherein in each of the plurality of template oligonucleotide sequences B comprises a unique oligonucleotide sequence in which (i) the first barcode sequence uniquely identifies the unique V oligonucleotide sequence of the template oligonucleotide and (ii) the second barcode sequence uniquely identifies the unique J oligonucleotide sequence of the template oligonucleotide.

R can be either nothing or comprises a restriction enzyme recognition site that comprises an oligonucleotide sequence that is absent from V, J, U1, U2, B1, B2 and B3.

In certain embodiments, the template composition includes a random oligonucleotide sequence. The random oligonucleotide sequence may be inserted in various sections between or within the components in the general formula I (5'-U1-B1-V-B2-R-B3-J-B4-U2-3') and be of various lengths in size (e.g., 8 base pairs in length).

Methods are used with the template compositions for determining non-uniform nucleic acid amplification potential among members of a set of oligonucleotide amplification primers that are capable of amplifying productively rearranged DNA encoding one or a plurality of adaptive immune receptors in a biological sample that comprises DNA from lymphoid cells of a subject.

Based on the determined non-uniform nucleic acid amplification potentials of each of the primers, the multiplex primer sets can be adjusted to reduce amplification bias. These bias-controlled primers can then be used on biological templates.

Further description about bias control methods are provided in U.S. Provisional Application No. 61/726,489, filed Nov. 14, 2012, U.S. Provisional Application No. 61/644,294, filed on May 8, 2012, and International Patent App. Publ. No. WO 2013/169957, which are incorporated by reference in their entireties.

High Throughput Sequencing

Sequencing can be performed using any of a variety of available high throughput single molecule sequencing machines and systems. Illustrative sequence systems include sequence-by-synthesis systems, such as the Illumina Genome Analyzer and associated instruments (Illumina HiSeq) (Illumina, Inc., San Diego, Calif.), Helicos Genetic Analysis System (Helicos BioSciences Corp., Cambridge, Mass.), Pacific Biosciences PacBio RS (Pacific Biosciences, Menlo Park, Calif.), or other systems having similar capabilities. Sequencing is achieved using a set of sequencing platform-specific oligonucleotides that hybridize to a defined region within the amplified DNA molecules. The sequencing platform-specific oligonucleotides are designed to sequence up amplicons, such that the V- and J-encoding gene segments can be uniquely identified by the sequences that are generated. See, e.g., U.S. Ser. No. 13/217,126; U.S. Ser. No. 12/794,507; PCT/US2011/026373; or PCT/US2011/049012, which is each incorporated by reference in its entirety.

In some embodiments, the raw sequence data is preprocessed to remove errors in the primary sequence of each read and to compress the data. A nearest neighbor algorithm can be used to collapse the data into unique sequences by merging closely related sequences, to remove both PCR and sequencing errors. See, e.g., U.S. Ser. No. 13/217,126; U.S. Ser. No. 12/794,507; PCT/US2011/026373; or PCT/US2011/049012, which is each incorporated by reference in its entirety.

Processing Sequence Data

Sequenced reads are filtered for those including CDR3 sequences. Sequencer data processing involves a series of steps to remove errors in the primary sequence of each read, and to compress the data. In one embodiment, a complexity filter is used to remove approximately 20% of the sequences that are misreads from the sequencer. Then, sequences are required to have a minimum of a six base match to both one of the J-regions and one of the V-regions. Applying the filter to the control lane containing phage sequence, on average only one sequence in 7-8 million passes these steps. Finally, a nearest neighbor algorithm may be used to collapse the data into unique sequences by merging closely related sequences, in order to remove both PCR error and sequencing error.

Further description for methods of processing sequence reads can be found in US App. Publ. No. 2012/0058902, US App. Publ. No. 2010/0330571, and International Patent App. Publ. No. WO/2010/151416, which are each incorporated by reference in its entirety.

PCR Template Abundance Estimation

In order to estimate the average read coverage per input template in the multiplex PCR and sequencing approach, a set of unique synthetic TCR or Ig analog templates, comprising each possible combination of Vβ and Jβ gene segments is employed (Carlson et al. 2013, Nature Communications 4:2680). These molecules are included in each PCR reaction at a low concentration selected so that most unique synthetic templates are not observed in the sequencing output. Using the known concentration of each synthetic template in the pool, the relationship between the number of observed unique synthetic molecules and the total number of synthetic molecules added to reaction was simulated (which closely matches a one-to-one relationship at the selected concentration). This information is then used to calculate, for each PCR reaction, the mean number of sequencing reads obtained per molecule of PCR template, and finally estimate the number of B cells or T cells in the input material bearing each unique Ig or TCR rearrangement, respectively.

Identification of Expanded and Enriched Effector Cell Clones

A B cell clone or a T cell clone may be defined as the population of cells bearing a unique IgH or TCRβ rearrangement, respectively.

In certain embodiments, a statistic is computed for each clone based on the frequency or size of the clone in a sample population. The statistic can be computed for a clone at different time points. In some embodiments, the clone is determined to be expanded or contracted at a second time point compared to a first time point based on the value of the statistic. In some embodiments, the frequency or size of the clone must be statistically significantly different between the two or more time points to be considered expanded or contracted. In certain embodiments, a proportion or percentage of the total T or B cell population or total number of genomes in the sample can be calculated for each clone.

In one embodiment, to computationally identify those clones whose frequencies differ between samples from a subject at different time points, or between cell populations (e.g., between total PBMCs and a specific sorted T cell population for the same time point), the algorithm described below can be used. The input data consists of the abundance for each clone in each of the two samples.

It is assumed that the repertoire contains S distinct clones, and their proportional abundances at time points 1 and 2 are given by the multinomial vectors $\pi^{(1)}=\{\pi^{(1)}1, \pi^{(1)}2, \ldots, \pi^{(1)}S\}$ and $\pi^{(2)}\{\pi^{(2)}1, \pi^{(2)}2, \ldots, \pi^{(2)}S\}$, with $\Sigma_{i=1}^{S}\pi_i^{(j)}=1$. Supposing that n clones have changed in abundance between the two time points, these clones were identified with the n-element index vector Δ.

Next, it can be assumed that the aggregated proportional change of all truly changed clone abundances is small (i.e., $\Sigma_{i\in\Delta}(\pi_i^{(2)}-\pi_i^{(1)})\ll 1$). In this regime, each observed clone can be independently tested for significance using a 2×2 contingency table. The Fisher exact test is employed to compute a p-value for each clone across the two samples. Specifically, suppose clone i is observed with abundance $k_i^{(1)}$ at time point 1 and $k_i^{(2)}$ at time point 2. A p-value for the 2×2 contingency table containing these abundances in one row was computed, and the remaining abundances (for clones other than i) on the other. By summing over hypergeometric probabilities, the Fisher exact test gives the p-value for the null hypothesis that the proportion of clone i in the repertoire is the same at both time points, that is $\pi_i^{(1)}=\pi_i^{(2)}$.

s is defined as representing the number of distinct clones actually observed across the two samples, where in general s<S. Without loss of generality, indices 1 through s of the repertoire clones correspond to the observed clones. After performing the above analysis on each of the s observed clones, a vector of p-values, $p=\{p_1, p_2, \ldots, p_s\}$, is used.

To choose a rejection region (thereby identifying a set of significantly changed clones between the two samples under consideration), the positive false discovery rate (pFDR) method of Storey, which defines (Storey, 2002, J. R. Statist. Soc. B 64:479-498) the pFDR as the expected proportion of true null hypotheses among all rejected hypothesis, can be used:

$$pFDR(\gamma) = Pr(\pi_i^{(1)} = \pi_i^{(2)} \mid p_i \leq \gamma)$$

$$= \frac{\pi_0 Pr(p_i \leq \gamma \mid \pi_i^{(1)} = \pi_i^{(2)})}{Pr(p_i \leq \gamma)}$$

$$= \frac{\pi_0 \gamma}{Pr(p_i \leq \gamma)}$$

The second equality follows from Bayes' theorem with $\pi_0$ being the prior probability that a hypothesis is null. The last equality follows from the definition of a p-value, if the p-values themselves are regarded as independent and identically distributed random variables.

For each p-value ($p_i$) the associated q-value ($q_i$) may be estimated, which is the minimum pFDR that can occur when rejecting p-values less than or equal to $p_i$. By examining the number of significant tests at various q-value thresholds, an appropriate threshold can be selected (e.g., see FIGS. 1A and 1B). Control of pFDR is preferred to control of the family-wise error rate (FWER), the probability of one or more false alternative hypotheses. The latter, which is typically controlled by the Bonferroni method, is overly conservative, failing to reject many false null hypotheses in order to attain any nontrivial FWER. The pFDR, on the other hand, rejects these hypotheses at the cost of a specifiable, small proportion of rejected true null hypotheses. The resulting set of significance tests allow the identification of B cell and T cell clones whose frequencies vary (i.e., dynamic B cell and T cell clones).

Monitoring T Cell and B Cell Response to Vaccination

Using high-throughput sequencing, lymphocyte clones responding to a vaccine may be detected. The vaccine may be a commonly used reference vaccine, or the vaccine may be a candidate vaccine. In one embodiment, the vaccine is for an infectious agent. Examples of target infectious agents for vaccine include, but are not limited to, influenza, HIV, HPV, malaria, smallpox, CMV, rabies, hepatitis A or B, and HSV. In one embodiment, the vaccine is a cancer vaccine. Examples of target cancers for a cancer vaccine include, but are not limited to, cervical cancer, pancreatic cancer, breast cancer, bladder cancer, and prostate cancer. In another embodiment, the vaccine can be live attenuated vaccines, inactivated vaccines, toxoid vaccines, subunit/conjugate vaccines, or biosynthetic vaccines. The vaccine may comprise DNA, RNA, virion capsule, etc. In one aspect, T cell clones induced by vaccination are detected.

Identifying Vaccine-Induced Responsive Clones

Methods provided herein may be used to identify B cell and T cell clones that are responsive to a vaccine. Vaccine responsive clones expand rapidly upon interacting with antigen, and clones present in a biological sample at a significantly high cell number, frequency, proportion, or abundance, can be identified.

Responsive T Cell Clones

In one embodiment, nucleic acid molecules comprising rearranged CDR3 regions of TCR loci obtained from 1) a first biological sample of a subject at a first time point prior to vaccination are sequenced and 2) a second biological sample of a subject at a second time point post vaccination are sequenced. Individual T cell clones can be detected by the presence of the uniquely rearranged CDR3 region. T cell clones that are responsive to vaccination are expanded, in a statistically significant fashion, in cell number in the second biological sample in comparison to the first biological sample. Relative abundance of the CDR3 region correlates to the number of T cells from the sample for the specific clone. In this way, by identifying T cell clones of significantly high abundance, or higher proportional abundance, in the second sample in comparison to the first sample, vaccine-induced responsive T cell clones are detected.

In one embodiment, the second biological sample is obtained at a time point at or around the peak of the immune response to the vaccine. For example, in one embodiment, the second time point is about 10-14 days post vaccination. In one embodiment, the second biological sample is obtained at least 10 days post vaccination. In one embodiment, the subject has received one dose of the vaccine. In another embodiment, the subject has received more than one dose of the vaccine (e.g., one or more boosters).

In one embodiment, the vaccine-induced responsive T cell clones are vaccine antigen-specific T cells. Antigen specificity can be determined using any of a variety of methods known in the art including, but not limited to, cell proliferation assays (e.g., $^3$H-thymidine incorporation), cytotoxicity assays (e.g., $^{51}$Cr release), MHC-peptide tetramer staining assays, enzyme-linked immunospot (ELISPOT) assays, and intracellular cytokine assays.

In one embodiment, activated effector T cells are sorted from the second biological sample prior to sequencing to identify significantly expanded T cell clones. In one embodiment, activated T cells are CD38$^+$HLA-DR$^+$ cells. In one embodiment, activated T cells are not sorted from the second biological sample, and vaccine-induced responsive T cell clones are identified from whole PBMCs.

In another embodiment, vaccine-induced responsive clones are identified by sequencing rearranged CDR3 regions from a single time point obtained post vaccination without comparison to a sample obtained prior to vaccination. Preferably, the activated effector T cells are sorted from the biological sample prior to sequencing, and the clones from the sort are compared to clones identified in a non-sorted sample from the same time point, with clones expanded (in a statistically significant manner) in the sort compared to the non-sorted sample considered vaccine-induced responsive clones.

For example, in one embodiment, a first biological sample and a second biological sample of a subject are obtained at a first time point post vaccination. The activated effector T cells are sorted from the second biological sample to obtain an activated T cell population. Nucleic acid molecules comprising rearranged CDR3 regions of TCR loci from the first sample and the sorted activated T cell population are sequenced. Vaccine-induced responsive clones are identified by identifying CDR3 regions of significantly high abundance in the activated T cell population in comparison to the first biological sample, wherein the CDR3 regions of high abundance correspond to expanded T cell clones in the activated T cell population.

Responsive B Cell Clones

In one embodiment, nucleic acid molecules comprising rearranged CDR3 regions of Ig loci obtained from 1) a first biological sample of a subject at a first time point prior to vaccination and 2) a second biological sample of a subject at a second time point post vaccination are sequenced. Once the CDR3 regions are sequenced, a clustering algorithm may be applied to cluster groups of CDR3 sequences of common descent comprising clones having undergone somatic hypermutation. B cell clones that are responsive to vaccination are significantly expanded in cell number in the second biological sample in comparison to the first biological sample, and clusters of clonally related B cells are detected by the rearranged CDR3 sequence clusters. Relative abundance of the CDR3 cluster correlates to the number of B cells from the sample for the specific clone. In this way, by identifying B cell clones of significantly high abundance in the second sample in comparison to the first sample, vaccine-induced responsive B cell clones are detected.

In one embodiment, the second biological sample is obtained at a time point at or around the peak of the immune response to the vaccine. For example, in one embodiment, the second time point is about 1-2 days post vaccination. In another embodiment, the second time point is about 10-14 days post vaccination. In one embodiment, the second biological sample is obtained at least 1 day post vaccination. In one embodiment, the subject has received one dose of the vaccine. In another embodiment, the subject has received more than one dose of the vaccine (e.g., one or more boosters).

In one embodiment, the vaccine-induced responsive B cell clones are vaccine antigen-specific B cells. Antigen specificity can be determined using any of a variety of methods known in the art including, but not limited to, capture assays (e.g., antigen-coated solid matrix), fluorescent-labeled antigen staining assays (e.g., microscopy and flow cytometry), and ELISPOT assays.

In one embodiment, activated, effector B cells are sorted from the second biological sample prior to sequencing to identify significantly expanded B cell clones. In one embodiment, activated B cells are CD25$^+$CD69$^+$CD80$^+$CD86$^+$ cells. In one embodiment, activated B cells are not sorted from the second biological sample, and vaccine-induced responsive B cell clones are identified from whole PBMCs.

In another embodiment, vaccine-induced responsive clones are identified by sequencing rearranged CDR3 regions from a single time point obtained post vaccination without comparison to a sample obtained prior to vaccination. Preferably, the activated B cells are sorted from the biological sample prior to sequencing, and the highly abundant clones are compared to clones identified in a non-sorted sample from the same time point.

For example, in one embodiment, a first biological sample and a second biological sample of a subject are obtained at a first time point post vaccination. The activated, effector B cells are sorted from the second biological sample to obtain an activated B cell population. Nucleic acid molecules comprising rearranged CDR3 regions of Ig loci from the first sample and the sorted activated B cell population are sequenced. Clonally related CDR3 regions are clustered. Vaccine-induced responsive clones are identified by identifying CDR3 clusters of significantly high abundance in the activated B cell population in comparison to the first biological sample, wherein the CDR3 clusters of high abundance correspond to expanded B cell clones in the activated B cell population.

Identifying Newly Recruited Memory Clones

The methods described herein may further be utilized to identify vaccine-induced responsive B cell and/or T cell clones that are recruited to the memory compartment. In particular, the number of vaccine-induced responsive effector cell clones recruited to memory may be determined, and the percentage of vaccine-induced responsive effector cell clones that are recruited to memory may also be determined. Furthermore, correlations between the expansion of a particular effector cell clone in response to vaccination and recruitment to the memory compartment can be examined. In order to detect newly recruited memory cells, the biological sample is obtained at a time sufficient for the B cells or T cells to transition from activated cells to memory cells. In one embodiment, the biological sample is obtained at least about 30 days following vaccination. In a particular embodiment, the biological sample is obtained about 90 days following vaccination. In another embodiment, the biological sample is obtained about 1, 2, 3, 4, 5, 6, 7, 8, 9, 10, 11, 12 or more months following vaccination. In one embodiment, the biological sample is obtained about 1, 2, 3, 4, 5, 6, 7, 8, 9, 10 or more years following vaccination.

Memory T Cell Clones

In one embodiment, nucleic acid molecules comprising rearranged CDR3 regions of TCR loci obtained from a third biological sample of a subject at a third time point post vaccination are sequenced in order to identify memory T cells that correspond to the vaccine-induced responsive T cell clones identified in the second sample. In one embodiment, the memory T cells clones of the third sample are compared to memory T cell clones of the first sample in order to identify newly recruited memory T cell clones corresponding to the vaccine-induced responsive T cell clones. Upon identifying newly recruited vaccine-induced memory T cell clones, it can be determined what proportion of the total memory T cell compartment is the newly recruited memory T cell clones. In this way, a degree of recruitment of vaccine-induced responsive clones to immunological memory can be identified. In one embodiment, a degree of recruitment may comprise the proportion of unique clones present in the set of vaccine-induced response clones which have been recruited to memory. In another embodiment, a degree of recruitment may comprise the proportion of T cells in the memory compartment that were recruited from among the vaccine-induced responsive clones. In one embodiment, a degree of recruitment of vaccine-induced responsive clones to the memory compartment is a biomarker for vaccine efficacy.

Memory B Cell Clones

In one embodiment, nucleic acid molecules comprising rearranged CDR3 regions of Ig loci obtained from a third biological sample of a subject at a third time point post vaccination are sequenced in order to identify memory B cells that correspond to the vaccine-induced responsive B cell clones identified in the second sample. In one embodiment, the memory B cells clones of the third sample are compared to memory B cell clones of the first sample in order to identify newly recruited memory B cell clones corresponding to the vaccine-induced responsive B cell clones. Upon identifying newly recruited vaccine-induced memory B cell clones, it can be determined what proportion of the total memory B cell compartment is the newly recruited memory B cell clones. In this way, a degree of recruitment of vaccine-induced responsive clones to immunological memory can be identified. In one embodiment, a degree of recruitment may comprise the proportion of unique clones present in the set of vaccine-induced response clones which have been recruited to memory. In another embodiment, a degree of recruitment may comprise the proportion of B cells in the memory compartment that were recruited from among the vaccine-induced responsive clones. In one embodiment, a degree of recruitment of vaccine-induced responsive clones to the memory compartment is a biomarker for vaccine efficacy.

Monitoring T Cell and B Cell Response to Infection

In another aspect, the adaptive immune response to infection can be monitored to identify T cell and/or B cell clones activated in response to infection. The infection can be caused by a virus, bacteria, parasite, or other pathogen. The infection can be acute (e.g., acute viral infection) or chronic. As used herein, the term "acute infection" refers to an infection characterized by rapid onset and resolution within, e.g., 14 days. In contrast, the term "chronic infection" refers to an infection that does not rapidly resolve. For example, a chronic infection may persist for years. The number of responsive clones and their relative abundance can be determined. Additionally, the recruitment of responsive clones to immunological memory can also be measured. The methods described herein may be used in, e.g., animal models and human patients.

Examples of viruses that cause acute viral infections include, but are not limited to, influenza, yellow fever virus (YFV), and smallpox. Examples of viruses that cause chronic viral infections include, but are not limited to, Epstein-Barr virus (EBV), hepatitis A virus (HAV), hepatitis B virus (HBV), hepatitis C virus (HCV), herpes simplex virus-1 (HSV-1), herpes simplex virus-2 (HSV-2), human immunodeficiency virus (HIV), human papilloma virus (HPV), and varicella zoster virus (VZV).

Identifying Infection-Induced Responsive Clones

Methods provided herein may be utilized to identify B cell and T cell clones that are responsive to an infection. Infection responsive clones expand rapidly upon interacting with antigen from the pathogen (e.g., viral antigen), and clones present in a biological sample at a significantly high cell number, or abundance, can be identified.

Responsive T Cell Clones

In one embodiment, nucleic acid molecules comprising rearranged CDR3 regions of TCR loci obtained from 1) a first biological sample of a subject at a first time point prior to infection are sequenced and 2) a second biological sample of a subject at a second time point post infection. T cell clones that are responsive to infection are significantly expanded in cell number in the second biological sample in comparison to the first biological sample, and individual T cell clones are detected by the presence of the uniquely rearranged CDR3 region. Relative abundance of the CDR3 region correlates to the number of T cells from the sample for the specific clone. In this way, by identifying T cell clones of significantly high abundance in the second sample in comparison to the first sample, infection-induced responsive T cell clones are detected.

In one embodiment, the second biological sample is obtained at a time point at or around the peak of the immune response to the infection. For example, in one embodiment, the second time point is about 1-2 days post inoculation with the virus. In another example, the second time point is 10-14 days post inoculation with a pathogen (e.g., virus or bacteria). In one embodiment, the second biological sample is obtained at least 1 day after inoculation. In another embodiment, the second biological sample is obtained at least 10 days post inoculation with a pathogen. In one embodiment, the second biological sample is obtained at a time point when the subject is experiencing symptomatic infection (e.g., fever, rash, vomiting, or diarrhea).

In one embodiment, the infection-induced responsive T cell clones are pathogen (e.g., viral) antigen-specific T cells. Antigen specificity can be determined using any of a variety of methods known in the art including, but not limited to, cell proliferation assays (e.g., $^3$H-thymidine incorporation), cytotoxicity assays (e.g., $^{51}$Cr release), MHC-peptide tetramer staining assays, ELISPOT assays, and intracellular cytokine assays.

In one embodiment, activated, effector T cells are sorted from the second biological sample prior to sequencing to identify significantly expanded T cell clones. In one embodiment, activated T cells are $CD38^+HLA-DR^+$ cells. In one embodiment, activated T cells are not sorted from the second biological sample, and infection-induced responsive T cell clones are identified from whole PBMCs.

In another embodiment, infection-induced responsive clones are identified by sequencing rearranged CDR3 regions from a single time point obtained post infection without comparison to a sample obtained prior to infection. Preferably, the activated, effector T cells are sorted from the biological sample prior to sequencing, and the highly abundant clones are compared to clones identified in a non-sorted sample from the same time point.

For example, in one embodiment, a first biological sample and a second biological sample of a subject are obtained at a first time point post infection. The activated, effector T cells are sorted from the second biological sample to obtain an activated T cell population. Nucleic acid molecules comprising rearranged CDR3 regions of TCR loci from the first sample and the sorted activated T cell population are sequenced. Infection-induced responsive clones are identified by identifying CDR3 regions of significantly high abundance in the activated T cell population in comparison to the first biological sample, wherein the CDR3 regions of high abundance correspond to expanded T cell clones in the activated T cell population.

Responsive B Cell Clones

In one embodiment, nucleic acid molecules comprising rearranged CDR3 regions of TCR loci obtained from 1) a first biological sample of a subject at a first time point prior to infection are sequenced and 2) a second biological sample of a subject at a second time point post infection. Once the CDR3 regions are sequenced, a clustering algorithm may be applied to cluster groups of CDR3 sequences of common descent comprising clones having undergone somatic hypermutation. B cell clones that are responsive to infection are significantly expanded in cell number in the second biological sample in comparison to the first biological sample, and clusters of clonally related B cells are detected by the rearranged CDR3 sequence clusters. Relative abundance of the CDR3 cluster correlates to the number of B cells from the sample for the specific clone. Relative abundance of the CDR3 clusters correlates to the number of B cells from the sample for the specific clone. In this way, by identifying B cell clones of significantly high abundance in the second sample in comparison to the first sample, infection-induced responsive B cell clones are detected.

In one embodiment, the second biological sample is obtained at a time point at or around the peak of the immune response to the infection. For example, in one embodiment, the second time point is about 1-2 days post inoculation with a pathogen (e.g., virus or bacteria). In another example, in one embodiment, the second time point is about 10 days post inoculation with a pathogen. In another embodiment, the second biological sample is obtained at least one day post inoculation with a pathogen. In another embodiment, the second biological sample is obtained 10 days post inoculation with a virus. In one embodiment, the second biological sample is obtained at a time point when the subject is experiencing symptomatic infection (e.g., fever, rash, vomiting, or diarrhea).

In one embodiment, the infection-induced responsive B cell clones are pathogen (e.g., viral) antigen-specific B cells. Antigen specificity can be determined using any of a variety of methods known in the art including, but not limited to, capture assays (e.g., antigen-coated solid matrix), fluorescent-labeled antigen staining assays (e.g., microscopy and flow cytometry), and ELISPOT assays.

In one embodiment, activated, effector B cells are sorted from the second biological sample prior to sequencing to identify significantly expanded B cell clones. In one embodiment, activated B cells are $CD25^+CD69^+CD80^+CD86^+$ cells. In one embodiment, activated B cells are not sorted from the second biological sample, and infection-induced responsive B cell clones are identified from whole PBMCs.

In another embodiment, infection-induced responsive clones are identified by sequencing rearranged CDR3 clusters from a single time point obtained post infection without comparison to a sample obtained prior to infection. Preferably, the activated, effector B cells are sorted from the biological sample prior to sequencing, and the highly abundant clones are compared to clones identified in a non-sorted sample from the same time point.

For example, in one embodiment, a first biological sample and a second biological sample of a subject are obtained at a first time point post infection. The activated, effector B cells are sorted from the second biological sample to obtain an activated B cell population. Nucleic acid molecules comprising rearranged CDR3 regions of Ig loci from the first sample and the sorted activated B cell population are sequenced. Infection-induced responsive clones are identified by identifying CDR3 clusters of significantly high abundance in the activated B cell population in comparison to the first biological sample, wherein the CDR3 clusters of high abundance correspond to expanded B cell clones in the activated B cell population.

Identifying Newly Recruited Memory Clones

The methods described herein may further be utilized to identify infection-induced responsive T cell clones that are recruited to the memory compartment. In particular, the number of infection-induced responsive effector cell clones recruited to memory may be determined, and the percentage of infection-induced responsive effector cell clones that are recruited to memory may also be determined. Furthermore, correlations between the expansion of a particular effector cell clone in response to infection and recruitment to the memory compartment can be examined. In order to detect newly recruited memory cells, the biological sample is obtained at a time sufficient for the B cells or T cells to transition from activated, effector cells to memory cells. In one embodiment, the biological sample is obtained at least about 30 days following infection. In a particular embodiment, the biological sample is obtained about 90 days following infection. In another embodiment, the biological sample is obtained about 1, 2, 3, 4, 5, 6, 7, 8, 9, 10, 11, 12 or more months following infection. In one embodiment, the biological sample is obtained about 1, 2, 3, 4, 5, 6, 7, 8, 9, 10 or more years following infection.

Memory T Cell Clones

In one embodiment, nucleic acid molecules comprising rearranged CDR3 regions of TCR loci obtained from a third biological sample of a subject at a third time point post infection are sequenced in order to identify memory T cells that correspond to the infection-induced responsive T cell clones identified in the second sample. In one embodiment, the memory T cells clones of the third sample are compared to memory T cell clones of the first sample in order to identify newly recruited memory T cell clones corresponding to the infection-induced responsive T cell clones. Upon identifying newly recruited infection-induced memory T cell clones, it can be determined what proportion of the total memory T cell compartment is the newly recruited memory T cell clones. In this way, a degree of recruitment of infection-induced responsive clones to immunological memory can be identified.

Memory B Cell Clones

In one embodiment, nucleic acid molecules comprising rearranged CDR3 regions of Ig loci obtained from a third biological sample of a subject at a third time point post infection are sequenced in order to identify memory B cells that correspond to the infection-induced responsive B cell clones identified in the second sample. In one embodiment, the memory B cells clones of the third sample are compared to memory B cell clones of the first sample in order to identify newly recruited memory B cell clones corresponding to the infection-induced responsive B cell clones. Upon identifying newly recruited infection-induced memory B cell clones, it can be determined what proportion of the total memory B cell compartment is the newly recruited memory B cell clones. In this way, a degree of recruitment of infection-induced responsive clones to immunological memory can be identified.

Determining Vaccine Effectiveness

In another aspect, the methods described herein are utilized to determine the effectiveness of a vaccine. In particular, a vaccine may be compared to a reference vaccine, e.g., a standard vaccine or a candidate vaccine.

In one embodiment, a method for determining the effectiveness of a vaccine comprises performing high-throughput sequencing of nucleic acid molecules comprising rearranged CDR3 regions of TCR and/or Ig loci obtained from a first biological sample of a subject at a first time point prior to vaccination, a second biological sample of the subject at a second time point post vaccination, and a third biological sample of the subject at a third time point post vaccination. Vaccine-induced responsive clones are identified as activated lymphocytes correlating to CDR3 regions that are of significantly high abundance in the second biological sample in comparison to the first biological sample. Newly recruited memory cell clones corresponding to the vaccine-induced responsive clones are then identified in the third sample. A degree of recruitment of vaccine-induced responsive clones to immunological memory is compared to a reference degree of recruitment, wherein the vaccine is effective when the degree of recruitment is greater than or equal to the reference degree of recruitment.

A degree of recruitment can be measured in relation to breadth and depth. Breadth is defined as how many vaccine responsive clones are recruited it into memory and depth is the strength of the clones that are recruited into memory. Depth can be assessed by either clonal abundance or by a separate test of broad neutralization.

When analyzing B cells, a clustering algorithm may be applied to cluster groups of CDR3 sequences of common descent comprising clones having undergone somatic hypermutation. B cell clones that are responsive to vaccination are significantly expanded in cell number in the second biological sample in comparison to the first biological sample, and clusters of clonally related B cells are detected by the rearranged CDR3 sequence clusters. Relative abundance of the CDR3 cluster correlates to the number of B cells from the sample for the specific clone.

In one embodiment, newly recruited memory cell clones are identified by comparing the one or more newly recruited memory cell clones from the third sample with one or more vaccine-induced responsive clones from the second sample to find matches between the newly recruited memory cell clones and the one or more vaccine-induced responsive clones.

The reference degree of recruitment may be based, e.g., on a degree of recruitment measured following a candidate vaccine, a reference vaccine, or an infection. In one embodiment, the degree of recruitment is a percentage of vaccine-induced responsive clones that match newly recruited memory cell clones. In one embodiment, the degree of recruitment is a percentage of vaccine-induced responsive clones that match newly recruited memory cell clones. In one embodiment, the degree of recruitment is a percentage of the total number of unique vaccine-induced responsive clones identified from the second sample. In one embodiment, the degree of recruitment is a percentage of the total population of vaccine-induced responsive clones identified from the second sample.

In this way, the number of unique vaccine-induced responsive clones, the total number of vaccine-induced responsive clones, and/or the degree of recruitment can be used as a benchmark to screen potential new vaccine candidates. In addition, the dynamics of T cell and B cell responses to a vaccine can be compared to the T cell and B cell responses to the corresponding infectious agent.

EXAMPLES

Example 1

Identifying Vaccine-Induced Activated T Cells

The investigation of pathogen-induced effector T cells is essential to accurately characterize the dynamics and breadth of the human immune response. The Yellow Fever vaccine (YFV) has been broadly used as a model to understand how a controlled, self-resolving acute viral infection induces an effective, long-term protective immune response. In order to analyze the dynamics of the T cell repertoire before, during, and after vaccination, human volunteers with the live attenuated yellow fever vaccine YF-17D, which constitutes an established model of a controlled acute viral infection. High-throughput sequencing was used to characterize the breadth of the anti-viral effector cell response.

In this study, vaccination with the yellow fever vaccine YF-Vax®, which is based on the YF-17D204 attenuated strain, was used as a model of infection, in particular acute viral infection.

In addition, the methods of the invention used to characterize the viral infection are equally applicable for other types of infection, for example, by parasites or bacteria. The methods described here are also applicable to assessing the breadth and depth of an immunoglobulin response to an infection or a vaccination.

The attenuated virus contained in YF-17D only harbors 20 amino acid changes as compared to the wild type strain; most of these are found in the E protein and are thought to result in changes in viral tissue tropism (Lee and Lobigs, 2008, Journal of Virology 82:6024-6033). In addition, this attenuated virus is replication-competent, so that administration of the YFV results in a mild viral infection that is predicted to elicit an immune response that is almost identical in quality to that induced by wild type infection (SanofiPasteur. YF-VAX® prospectus, Document LE6445-LE6446).

Materials and Methods

Vaccination and Sample Collection

Nine volunteers between the ages of 18 and 45 received the yellow fever single dose vaccine YF-VAX® (based on the YF-17D204 strain of the yellow fever virus, (SanofiPasteur. YF-VAX® prospectus, Document LE6445-LE6446)), and to have 200 mL of blood drawn at three different time points: immediately before vaccination (day 0), two weeks post-vaccination (day 14), and 3 months post-vaccination (day 90). Written informed consent to use the blood samples in this study was obtained from each donor. The administration of the YF vaccine and all blood draws and were performed at the UWVRC.

Cell Sorting

Whole blood samples (200 ml) were collected and PBMCs were isolated by Histopaque (Sigma-Aldrich, St. Louis, Mo.) density gradient centrifugation. CD8$^+$ T cells were isolated from total PBMCs by magnetic separation using CD8 MicroBeads and the autoMACs Pro Separator (both from Miltenyl Biotec, Auburn, Calif.), followed by staining with anti-CD3-Alexa Fluor 700, anti-CD8-APC-H7, anti-CD38-PE, HLA-DR-FITC, anti-CD14-Pacific Blue, anti-CD19-V450, anti-CD45RO-PE Cy7, anti-CD45RA-APC, anti-CD62L-PerCP Cy5.5, and DAPI (all obtained from BD BioSciences, San Jose, Calif.). Cells were also stained with propidium iodide (PI) to detect cell viability. T cell subpopulations were sorted using the BD FACSAria II and FACSDiva v6.1.3 software (BD Biosciences). First, cells were gated on PI$^-$CD14$^-$CD19$^-$ to remove dead cells, monocytes and B cells. Cells were then gated on CD3$^+$CD8$^+$ to exclude non-T cell lymphocytes, and finally four different CD8$^+$ T cell subsets were isolated: CD3$^+$CD8$^+$CD14$^-$CD19$^-$CD45RA$^-$CD45RO$^+$ memory T cells ($T_M$, day 0 only); CD3$^+$CD8$^+$CD14$^-$CD19$^-$CD38$^+$HLA$^-$DR$^+$ antigen-experienced, activated effector T cells ($T_{AE}$, day 14 only), CD3$^+$CD8$^+$CD14$^-$CD19$^-$CD45RA$^-$CD45RO$^+$CD62Llo effector memory T cells ($T_{EM}$, day 90 only), and CD3$^+$CD8$^+$CD14$^-$CD19$^-$CD45RA$^-$CD45RO$^+$CD62L$^{hi}$ central memory T cells ($T_{CM}$, day 90 only). To avoid contamination, CD38$^+$HLA-DR$^+$ cells were excluded from the effector memory and central memory T cell populations. Day 90 samples from three of the volunteers were discarded due to contamination.

DNA Extraction and Immune Repertoire Sequencing

Genomic DNA was purified from total PBMC and each sorted T cell population sample using the QIAmp DNA Blood Mini Kit (Qiagen). For each sample, DNA was extracted from ~1 million T cells, and the TCRβ CDR3 regions were amplified and sequenced using the methods described herein, (ImmunoSEQ™, Adaptive Biotechnologies, Seattle, Wash. previously described (Robins et al. 2009, Blood 114:4099-4107)). In brief, bias-controlled V and J gene primers were used to amplify rearranged V(D)J segments for high throughput sequencing at about 20× coverage, as described above. After correcting sequencing errors via a clustering algorithm, CDR3 segments were annotated according to the International ImMunoGeneTics collaboration (Lefranc et al. 2004, In Silico Biol 4:17-29; Yousfi et al. 2004, Bioinformatics (Oxford, England) 20 Suppl 1:i379-385), to identify the V, D, and J genes that contributed to each rearrangement. Sequences were classified as non-productive if it was determined that non-templated insertions or deletions produced frame-shifts or premature stop codons.

PCR Template Abundance Estimation

In order to estimate the average read coverage per input template in the multiplex PCR and sequencing approach, a set of approximately 850 unique synthetic TCR analog templates, comprising each possible combination of Vβ and Jβ gene segments, was employed (Carlson et al. 2013, Nature Communications 4:2680). These molecules were included in each PCR reaction at a low concentration selected so that most unique synthetic templates were not observed in the sequencing output. Using the known concentration of each synthetic template in the pool, the relationship between the number of observed unique synthetic molecules and the total number of synthetic molecules added to reaction was simulated (which closely matches a one-to-one relationship at the selected concentration). This information was then used to calculate, for each PCR reaction, the mean number of sequencing reads obtained per molecule of PCR template, and finally estimate the number of T cells in the input material bearing each unique TCR rearrangement.

Identification of Expanded and Enriched Effector T Cell Clones

A T cell clone was defined as the population of T cells bearing a unique TCRβ rearrangement. To computationally identify those T cell clones whose frequencies differ between samples from a given volunteer taken at different time points, or between cell populations (e.g. between total PBMCs and a specific sorted T cell population for the same time point), the algorithm described below was used. The input data consists of the abundance for each TCRβ clone in the sample.

It was assumed that the repertoire contains S distinct clones, and their proportional abundances at time points 1 and 2 are given by the multinomial vectors $\pi^{(1)}=\{\pi^{(1)}1, \pi^{(1)}2, \ldots, \pi^{(1)}S\}$ and $\pi^{(2)}\{\pi^{(2)}1, \pi^{(2)}2, \ldots, \pi^{(2)}S\}$, with $\Sigma_{i=1}^{S}\pi_i^{(j)}=1$. Supposing that n clones have changed in abundance between the two time points, these clones were identified with the n-element index vector Δ.

Next, it was assumed that the aggregated proportional change of all truly changed clone abundances is small (i.e., $\Sigma_{i\in\Delta}(\pi_i^{(2)}-\pi_i^{(1)})<<1$). In this regime, each observed clone can be independently tested for significance using a 2×2 contingency table. The Fisher exact test was employed to compute a p-value for each clone across the two samples. Specifically, suppose clone i is observed with abundance $k_i^{(1)}$ at time point 1 and $k_i^{(2)}$ at time point 2. A p-value for the 2×2 contingency table containing these abundances in one row was computed, and the remaining abundances (for clones other than i) on the other. By summing over hypergeometric probabilities, the Fisher exact test gives the p-value for the null hypothesis that the proportion of clone i in the repertoire is the same at both time points, that is $\pi_i^{(1)}=\pi_i^{(2)}$.

s was defined as representing the number of distinct clones observed across the two samples, where in general s<S. Without loss of generality, indices 1 through s of the repertoire clones correspond to the observed clones. After performing the above analysis on each of the s observed clones, a vector of p-values, $p=\{p_1, p_2, \ldots, p_s\}$, was used.

To choose a rejection region (thereby identifying a set of significantly changed clones between the two samples under consideration), we use the positive false discovery rate (pFDR) method of Storey, which defines (Storey, 2002, J. R. Statist. Soc. B 64:479-498), the pFDR as the expected proportion of true null hypotheses among all rejected hypothesis:

$$pFDR(\gamma) = Pr(\pi_i^{(1)} = \pi_i^{(2)} \mid p_i \leq \gamma)$$
$$= \frac{\pi_0 Pr(p_i \leq \gamma \mid \pi_i^{(1)} = \pi_i^{(2)})}{Pr(p_i \leq \gamma)}$$
$$= \frac{\pi_0 \gamma}{Pr(p_i \leq \gamma)}$$

The second equality follows from Bayes' theorem with $\pi_0$ being the prior probability that a hypothesis is null. The last equality follows from the definition of a p-value, if the p-values themselves are regarded as independently and identically distributed random variables.

For each p-value ($p_i$) the associated q-value ($q_i$) may be estimated, which is the minimum pFDR that can occur when rejecting p-values less than or equal to $p_i$. By examining the number of significant tests at various q-value thresholds, an appropriate threshold can be selected (e.g., see FIGS. A and 4B1). Control of pFDR is preferred to control of the family-wise error rate (FWER)—the probability of one or more false alternative hypotheses. The latter, which is typically controlled by the Bonferroni method, is overly conservative, failing to reject many false null hypotheses in order to attain any nontrivial FWER. The pFDR, on the other hand, rejects these hypotheses at the cost of a specifiable, small proportion of rejected true null hypotheses.

The resulting set of significance tests allow the identification of T cell clones whose frequencies vary (i.e., dynamic T cell clones). For example, applying this algorithm to the comparison of total PBMCs isolated on day 14 post-vaccination to activated $CD8^+$ T cells purified from the same sample identifies a set of enriched, activated $CD8^+$ T cells that are expected to be YFV-specific. In contrast, the comparison of total PBMCs obtained from the same volunteer on day 0 (pre-vaccination) and on day 14 post-vaccination identifies a set of putative YFV-reactive clones.

Results

It is well established that effector $CD8^+$ T cells expand in response to an acute viral infection (Pulendran and Ahmed, 2011, Nature Immunology 12:509-517). Expanded clones can either bind specifically to a pathogen-derived epitope presented by a type I HLA molecule, or they can be induced to expand non-specifically by cytokines released by other cells, in a process known as bystander effect (Murali-Krishna et al. 1998, Immunity 8:177-187). In the case of the YFV model, which has been extensively used to characterize the human antiviral immune response since it results in a self-limited, acute viral infection (Ahmed and Akondy, 2011, Immunology and Cell Biology 89:340-345; Pulendran, 2009, Nature Reviews Immunology 9:741-747), activated effector $CD8^+$ T cells peak two weeks post-vaccination, and express a particular set of phenotypic markers, including CD38, HLA-DR, Ki-67 and Bcl-2 (Miller et al. 2008, Immunity 28:710-722). The massive expansion of activated effector $CD8^+$ T cells in response to vaccination with YFV is specific since existing memory $CD8^+$ T cells specific for other viruses such as CMV or EBV do not contribute to the activated, proliferating pool of $CD8^+$ T cells (Miller et al. 2008, Immunity 28:710-722).

To further explore the dynamics of the T cell repertoire in response to an acute viral infection, a single dose of the live attenuated YFV (YF-VAX®, based on the YF-17D204 strain of the YF virus (SanofiPasteur. YF-VAX® prospectus, Document LE6445-LE6446)) was administered to nine healthy volunteers, none of whom reported being previously exposed to the YF virus or having received YFV. 200 mL of peripheral blood were drawn from each participant on day 0 (immediately prior to vaccination), and on days 14 and 90 post-vaccination (Table 1, Appendix). To identify $CD8^+$ T cells present in the memory compartment prior to immunization, a fraction of the total PBMCs obtained from all volunteers on day 0 was sorted into $CD8^+$ memory T cells (TM0, defined as $CD3^+CD8^+CD14^-CD19^-CD45RA^-CD45RO^+$ cells). In addition, to characterize the activated effector $CD8^+$ T cells induced by vaccination with YFV, a fraction of the total PBMCs obtained on day 14 post-vaccination was sorted by selecting $CD3^+CD8^+CD14^-CD19^-CD38^+HLA\text{-}DR^+$ activated effector CD8 T cells (TX 14) (Miller et al. 2008, Immunity 28:710-722). Finally, to determine which of these clones enter the memory compartment, a fraction of the total PBMCs obtained on day 90 was sorted into effector memory ($T_{EM-90}$) and central memory ($T_{CM-90}$) $CD8^+$ T cells (respectively $CD8^+CD45RO^+CD62L^{lo}$ and $CD8^+CD45RO^+CD62L^{hi}$) (Sallusto et al. 1999, Nature 401:708-712). Table 1 (Appendix) shows the cell populations studied (including the surface markers used for sorting when applicable), and the days post-immunization that the samples were collected. Three of the samples on day 90 had to be discarded due to contamination.

Genomic DNA was extracted from about 1 million T cells for either total PBMCs or sorted T cell populations (Table 1), and the CDR3 regions of rearranged TCRβ loci were PCR amplified and high-throughput sequenced as previously described (Robins et al. 2009, Blood 114:4099-4107). The resulting TCRβ sequences are nearly unique for each clone, so that the data can be used to assess the dynamics of the cellular adaptive immune response both over time and between T cell subpopulations. Additionally, the number of original templates corresponding to each PCR-amplified clonal sequence was determined by assessing the amplification of a set of synthetic templates, thus providing an estimate of the cellular abundance for each clone in each sample.

Identification of Vaccine-Induced Clones

To assess the dynamics of the YFV-induced effector T cell repertoire, it was determined whether each unique clone (as defined by sequencing the CDR3 region of the TCRβ chain) was enriched in the day 14 post-vaccination, YFV-induced effector T cell compartment (as defined by the expression of CD38 and HLA-DR (Miller et al. 2008, Immunity 28:710-722)), in comparison to the total PBMC sample obtained from the same individual at the same time point.

To do this, a novel statistical method described above was developed to identify clones with significant proportional abundance differences between two samples.

FIGS. 1A and 1B show data used for selection of FDR thresholds. FIG. 1A shows the number of clones classified as YFV induced for various FDR significance thresholds for all subjects. By examining the number of significant tests at various Q value thresholds (FDR thresholds), an appropriate threshold can be selected. Here, a threshold of 0.01 was selected. FIG. 1B shows the number of clones classified as putatively reactive clones for various FDR significance thresholds for all subjects. A threshold of 0.05 was selected. Each subject is represented by a different tone of gray, as indicated in the legend.

This approach controlled for the false positive rate and accounted for experimental errors that result in the presence of false positives in the YFV-induced effector CD8+ T cell population (e.g., cells that do not have the indicated surface markers). This avoided overstating the number of YFV-induced clones, which would result from a simple enumeration of clones present in the sorted population. Instead, a clone was considered to be YFV-induced if (a) it was significantly enriched in the effector CD8+ T cell population with respect to the corresponding total PBMC sample, and (b) it carried a productive TCRβ rearrangement. Since the volunteers who participated in this study had not been previously exposed to either the YF virus or the YFV, it was also taken into consideration whether each unique CD8+ T cell clone identified was present in the day 0 pre-vaccination memory cell population ($T_{M0}$). Based on these criteria, T cell clones were classified into four categories, as follows: YFV-induced clones (i.e. enriched in the day 14 CD38+ HLA-DR+ sort vs. the day 14 PBMC sample from that individual, but absent in the corresponding TM0 sample); cross-reacting or by-stander clones (i.e. enriched in the day 14 CD38+HLA-DR+ sort vs. the corresponding PBMCs but present in $T_{M0}$), and those not enriched in the CD38+HLA-DR+ sort, which could be absent in the $T_{M0}$ sample (i.e. corresponding either to YFV-induced cells that did not express surface markers previously defined for activated effector CD8+ T cells (Miller et al. 2008, Immunity 28:710-722), or to false negatives, i.e. cells that failed to be sorted into the activated effector compartment by flow cytometry) or present in $T_{M0}$ (i.e., clones similar to those in the previous category but pre-existing in the memory compartment at the time of vaccination with YFV).

Figure 2A:
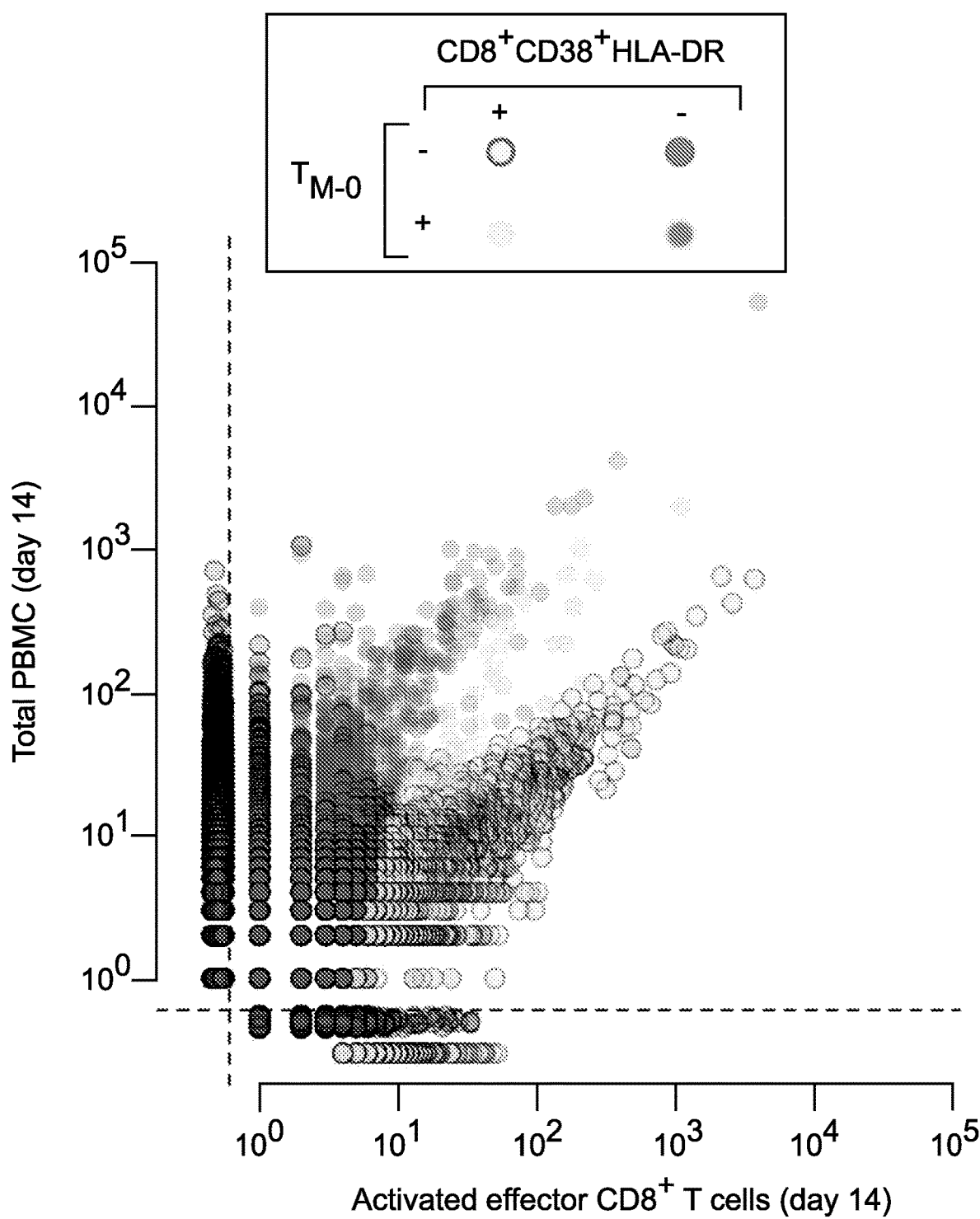
Figure 2B:
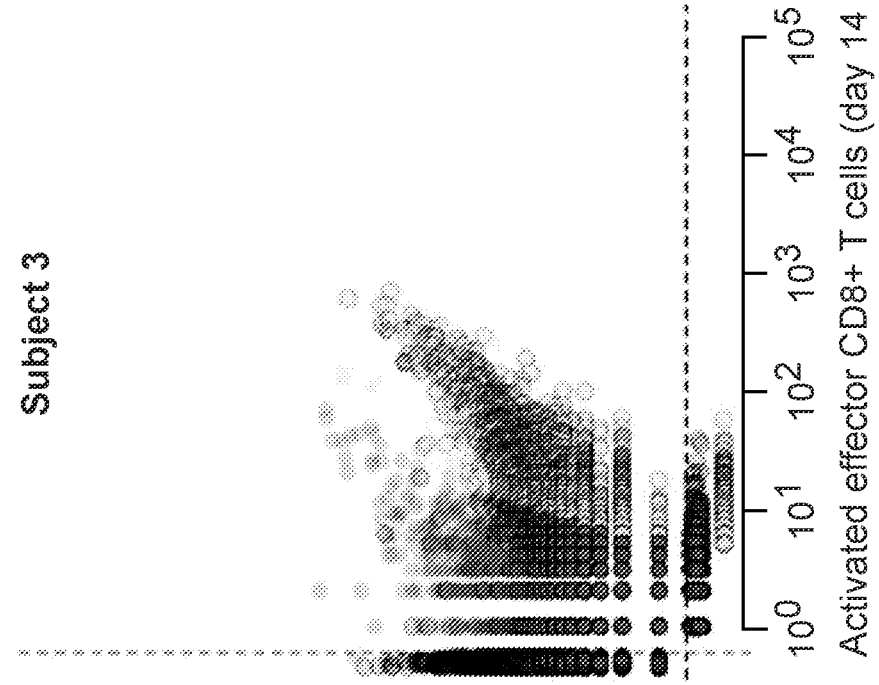
Figure 2B:
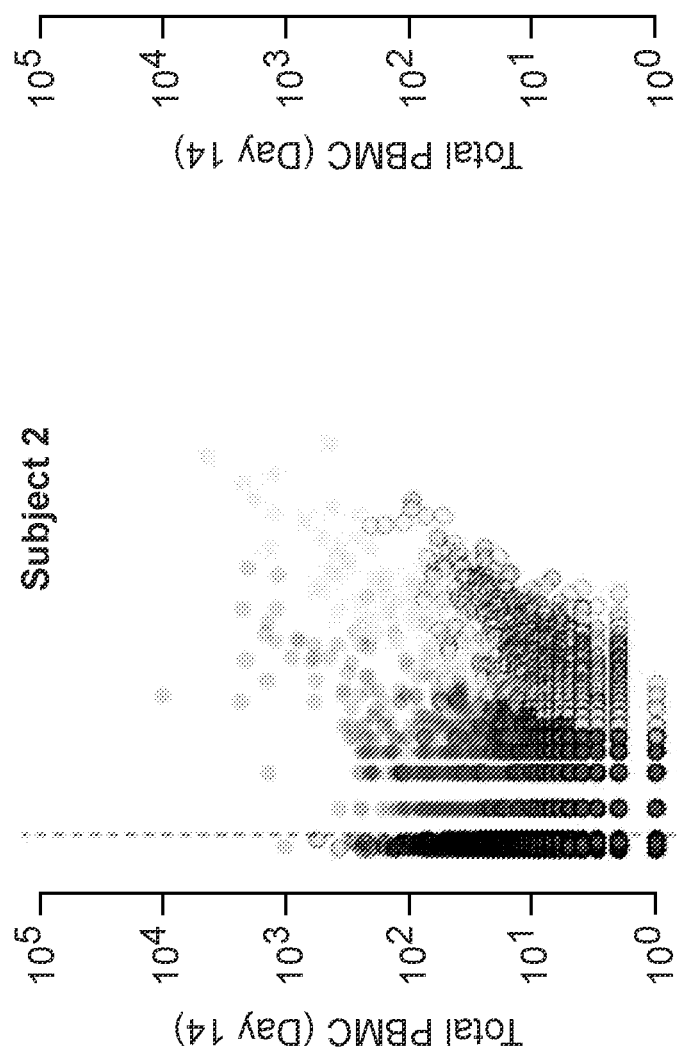
Figure 2C:
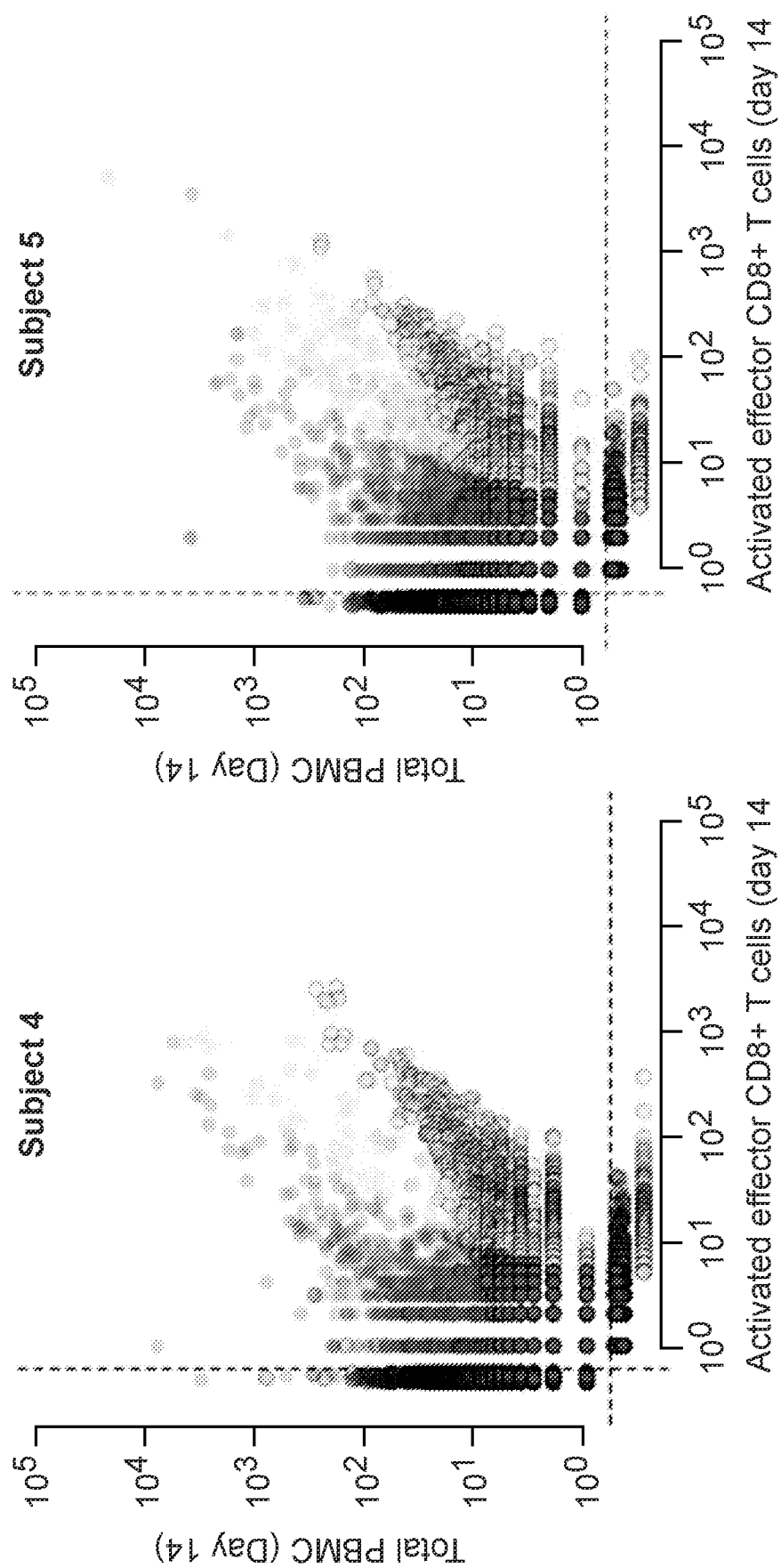
Figure 2E:
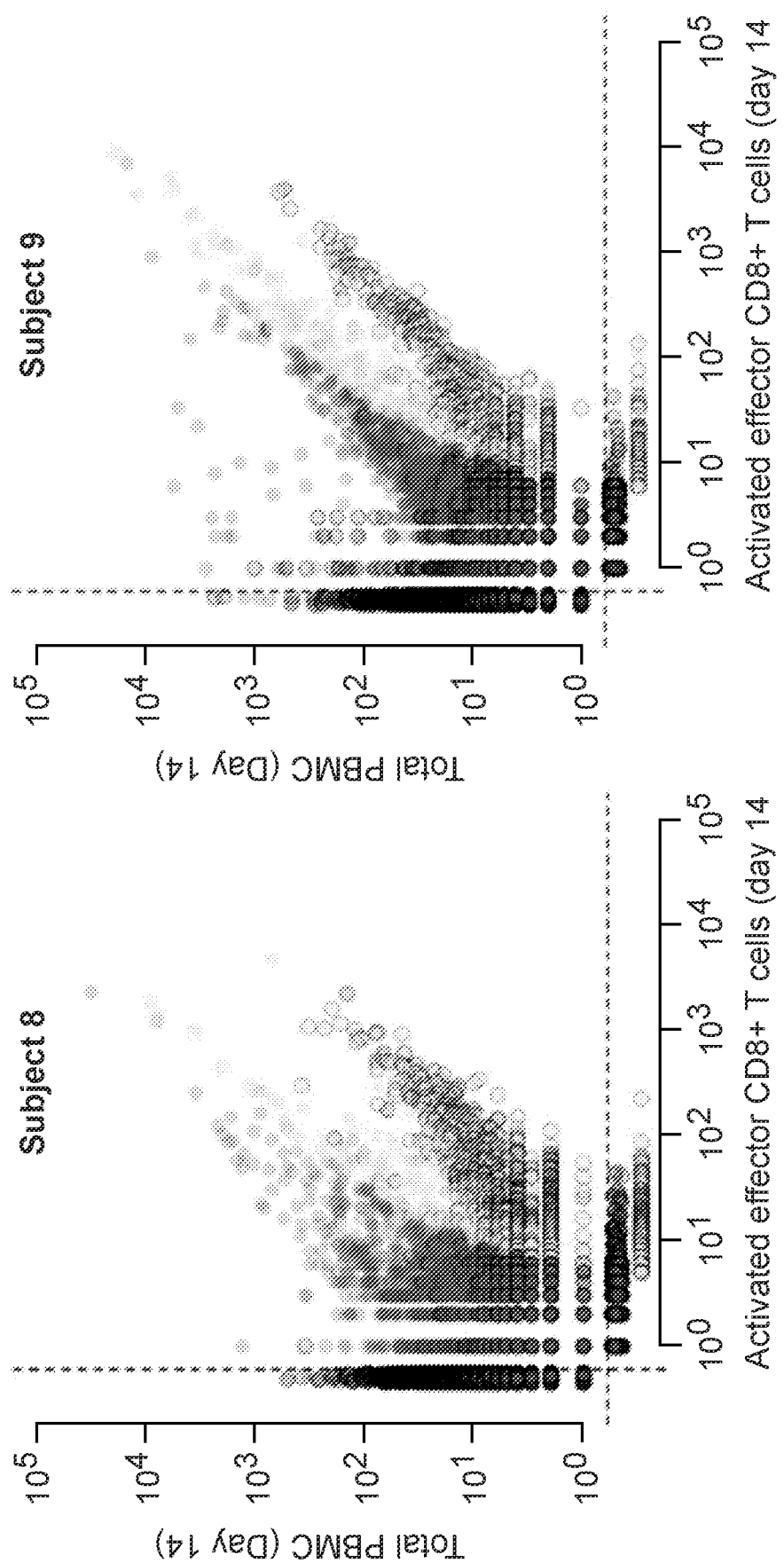

FIGS. 2A and 2B show the identification of YFV-induced clones. FIG. 2A shows a graph of the abundance of unique clones identified by statistical enrichment on the activated effector CD38+ HLA-DR+CD8+ T cell compartment on day 14 post-vaccination (TAE-14) versus those present in the corresponding total PBMC sample from the same time point for subject 1. FIG. 2B shows the same for subjects 2 to 9. Clones were classified into four categories based both on their presence in the TAE-14 and the TM-0 compartments. Red clones are present in the TAE-14 compartment, whereas gray clones are not; while clones absent in the TM-0 compartment have a black edge and those present in the TM-0 compartment do not. Darker colors indicate that multiple data points have been superimposed in that particular position. Regions bound by dashed lines indicate clones present in only one sample. YFV-induced clones were significantly enriched in the CD38+ HLA-DR+CD8+ T cell-sorted population compared to the corresponding total PBMC sample.

For the nine subjects in the study, an average of 2,000 clones were detected that were enriched in the activated, effector CD8+ T cell subpopulation as compared to the corresponding PBMC sample from the same individual (2135+/−770) (Table 2, Appendix). This number, therefore, constitutes a direct estimate of the number of activated effector CD8+ T cell clones that expand upon binding to HLA:YFV-derived epitope complexes. In addition, the vast majority of these clones (on average 91.5%, Table 2, Appendix) were absent in the $T_{M0}$ population, and were thus very likely YFV-specific.

Example 2

Characterization of the Recruitment of Individual Clones to Immunological Memory In order to determine which of the YFV-induced clones identified in the previous example entered the long-term central and effector memory compartments, samples obtained from six of the volunteers ninety days post-vaccination were analyzed (Table 1, Appendix). Preliminary studies have demonstrated that YFV-induced activated effector CD8+ T cells return to baseline levels 30 days post-immunization, and suggest that YFV antigen-specific cells that are detected beyond this time point correspond to memory cells (Miller et al. 2008, Immunity 28:710-722). Therefore, YFV-induced clones identified as enriched on the d14 activated, effector T cell post-immunization compartment, but absent from the $T_{M0}$ compartment in the corresponding day 90 post-immunization samples (i.e., the putative YFV-specific clones) were tracked to determine which clones were contained in the effector memory compartment ($T_{EM}$, defined as CD3+, CD8+ CD14−, CD19−, CD45RA−, CD45RO+ CD62L$^{lo}$), the central memory compartment ($T_{CM}$, defined as CD3+, CD8+ CD14−, CD19−, CD45RA−, CD45RO+ CD62L$^{hi}$), or both.

Figure 3:
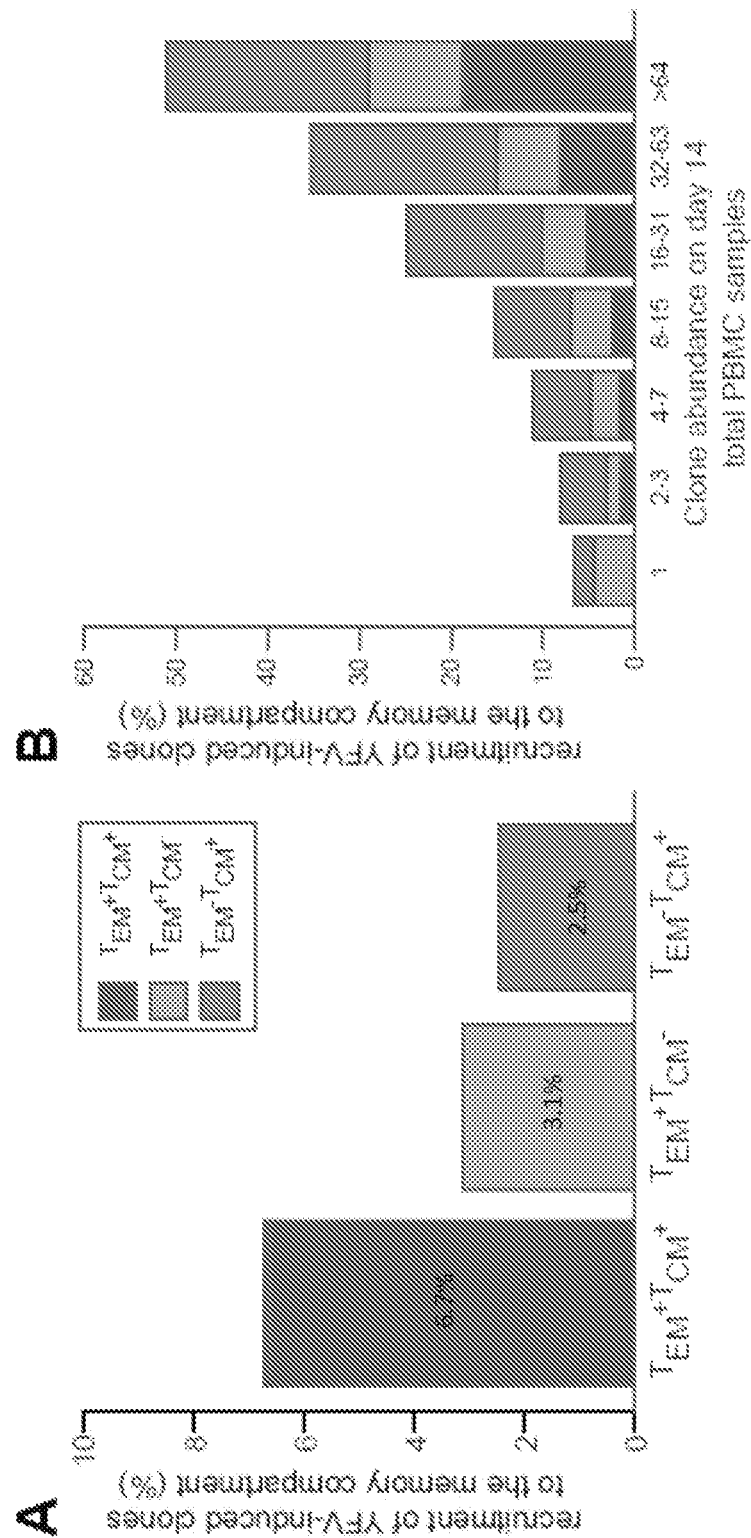
FIGS. 3A and 3B show recruitment of YFV-induced clones to immunological memory compartments.

FIGS. 3A and 3B show recruitment of YFV-induced clones to immunological memory compartments. FIG. 3A shows the efficiency of recruitment of YFV-induced clones to the effector (TEM+ TCM−) and central (TEM− TCM+) memory compartments, or both (TEM+ TCM+) as a percentage of all clones classified as YFV induced. FIG. 3A shows that, respectively, 3.1% and 2.5% of YFV-induced clones absent in $T_{M0}$ were identified exclusively in the $T_{EM}$ or the $T_{CM}$ compartments, while 6.7% were identified in both.

FIG. 3B shows the efficiency of recruitment to the effector and central memory compartments (or both) for YFV-induced clones absent from the day 0 pre-vaccination total PBMC samples, classified into categories based on their abundance in the day 14 post-vaccination total PBMC samples. Clones with a higher degree of expansion are more efficiently recruited to the memory compartment. The aggregated data for all subjects are shown; subject-wise source data can be found in Table 3 (Appendix). Table 3 shows the number of YFV-induced clones absent on the $T_{M-0}$ compartment, classified based on their recruitment to the $T_{CM-90}$ and $T_{EM-90}$ compartments as well as the level of expansion, measured by their abundance on the day 14 post-vaccination total PBMC samples.

Figure 4:
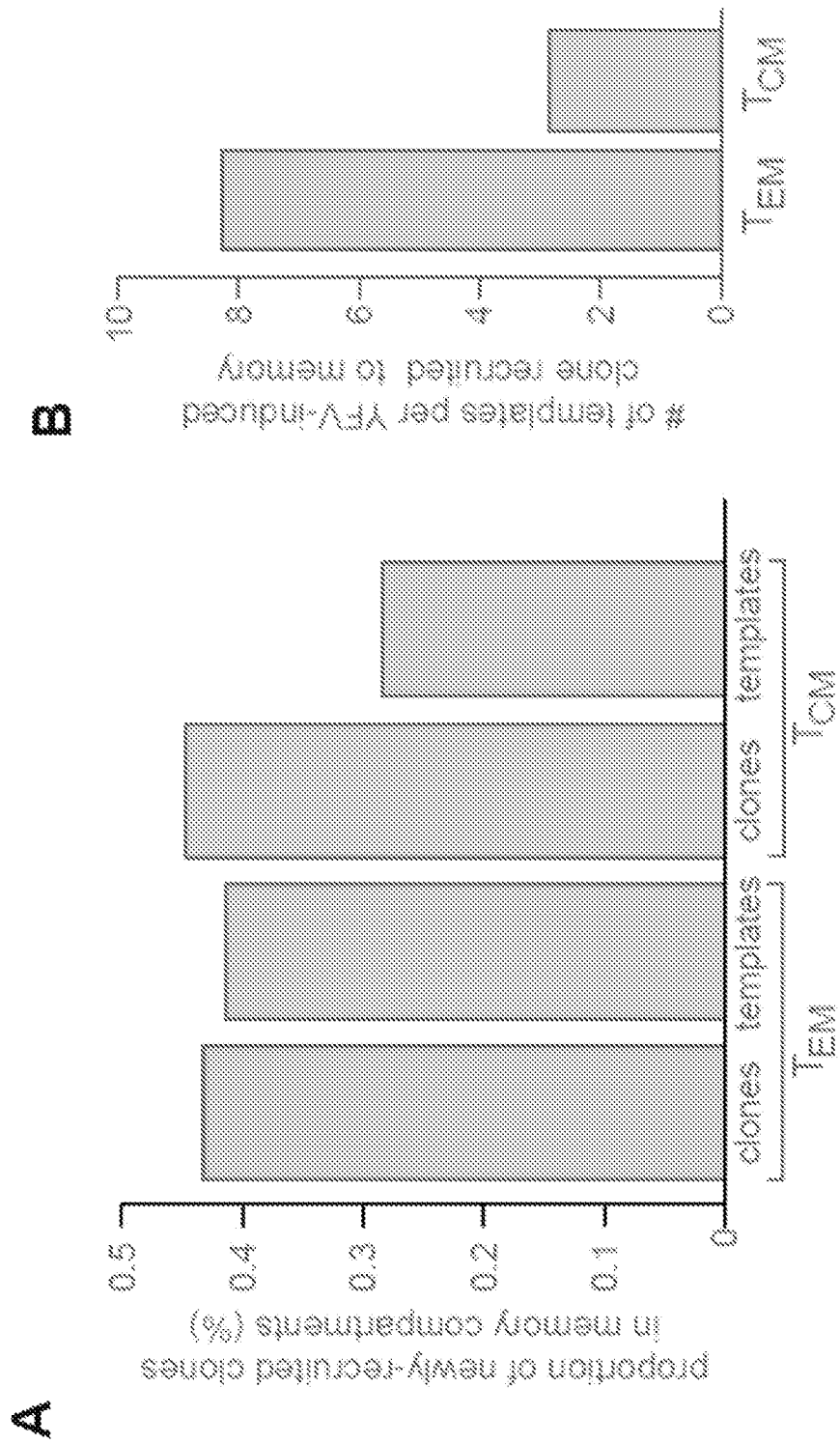
FIG. 4A shows the proportion of YFV-induced clones newly recruited to the effector ($T_{EM-90}$) and central ($T_{CM-90}$) memory compartments on day 90 post-vaccination, computed both by clone and template counts. The YFV-induced clones that were newly recruited to the $T_{EM}$ or the $T_{CM}$ compartments represent 0.43% and 0.45% of their respective memory compartments, as measured by unique clone counts, or 0.41% and 0.28% as measured by template abundance of the corresponding memory compartment aggregated over all samples.
FIG. 4B shows the number of templates per YFV-induced clone identified in the $T_{EM-90}$ and $T_{CM-90}$ memory compartments. More templates per clone were observed in the $T_{EM-90}$ compartment, indicating that these clones were more highly expanded. The aggregated data for all subjects are shown; subject-wise source data can be found in Table 4 in the Appendix.

Composition of the effector and central memory compartments on day 90 post-vaccination. FIG. 4A shows the proportion of YFV-induced clones newly recruited to the effector ($T_{EM-90}$) and central ($T_{CM-90}$) memory compartments on day 90 post-vaccination, computed both by clone and template counts. The YFV-induced clones that were newly recruited to the $T_{EM}$ or the $T_{CM}$ compartments represent 0.43% and 0.45% of their respective memory compartments, as measured by unique clone counts, or 0.41% and 0.28% as measured by template abundance of the corresponding memory compartment aggregated over all samples. FIG. 4B shows the number of templates per YFV-induced clone identified in the $T_{EM-90}$ and $T_{CM-90}$ memory compartments. More templates per clone were observed in the $T_{EM-90}$ compartment, indicating that these clones were more highly expanded. The aggregated data for all subjects are shown; subject-wise source data can be found in Table 4 in the Appendix. While the number of templates per unique CD8+ T cell clone in the $T_{EM}$ compartment averaged 8.3, those in the $T_{CM}$ compartment averaged 2.8, indicating that YFV-induced clones recruited to the effector memory are more significantly expanded than those recruited to the central memory compartment (FIG. 4B). Finally, whether any indicator of specificity (such as CDR3 length or V-J gene usage) correlated with the probability that a given CD8+ T cell clone would be recruited to memory compartment was analyzed. Although no simple indicator showed association, it was found that both the degree of expansion and the specificity determined by effector sorting positively associated with recruitment to memory (Tables 3-5, Appendix).

Example 3

Concordance Between the Expansion in Total PBMCs and Enrichment in the Activated Effector CD8+ T Cell Compartment In addition to the data presented above, the approach disclosed herein also allowed for the identification of activated, effector CD8+ T cells that expanded massively in response to YFV through the direct comparison of the unsorted total PBMC repertoires isolated on days 0 and 14 post-immunization. The statistical method described in detail above can be applied to the identification of T cell clones that have significantly expanded in the d14 PBMC sample as compared to the day 0 pre-immunization sample from the same individual (FIGS. 1B and 5).

Figure 5A:
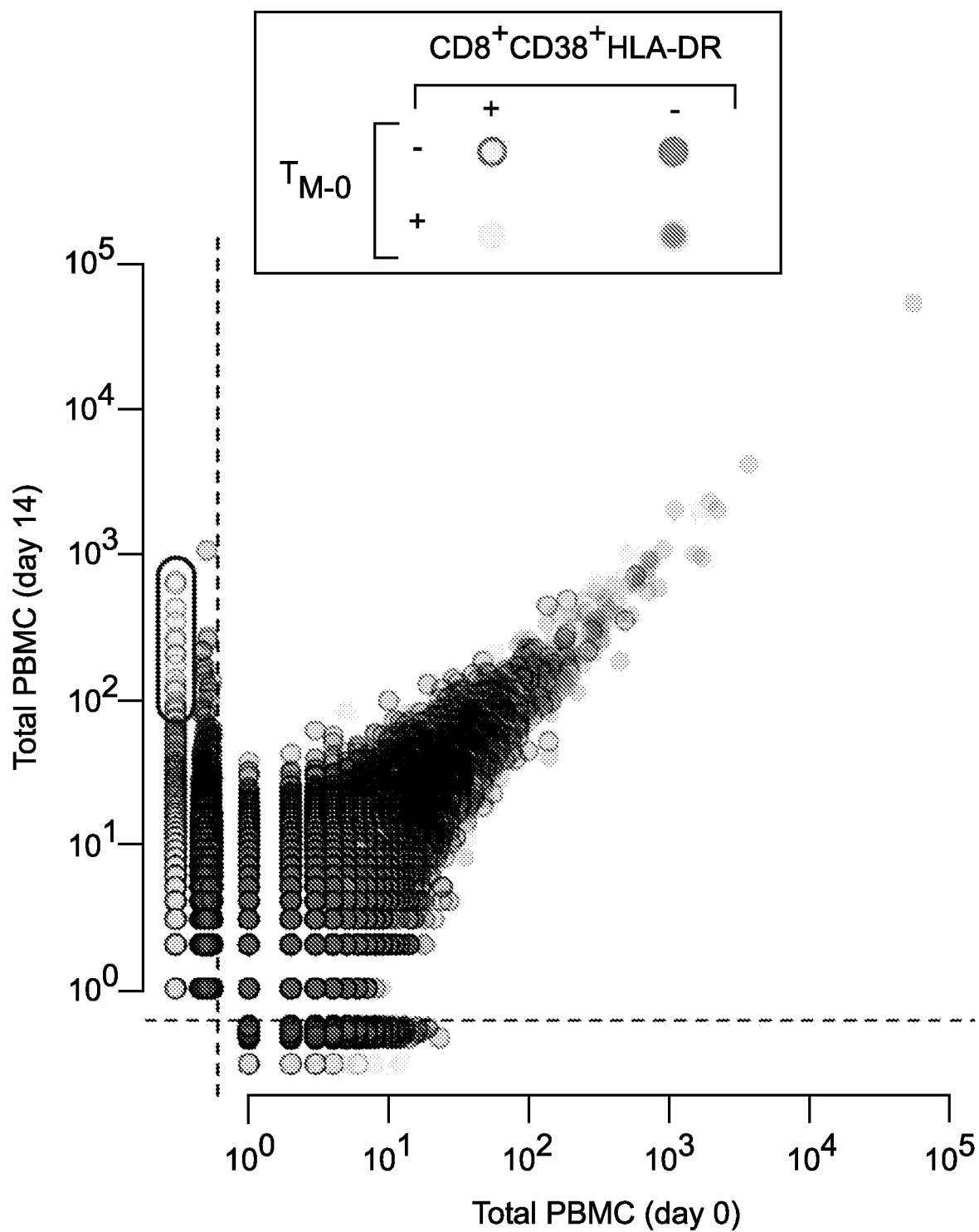
FIG. 5A shows the abundance of unique clones identified by statistical enrichment in the day 14 post-vaccination total PBMC sample compared to the pre-vaccination day 0 total PBMC sample from subject 1. Putatively reactive clones are enclosed by a circle in FIG. 5A.
Figure 5B:
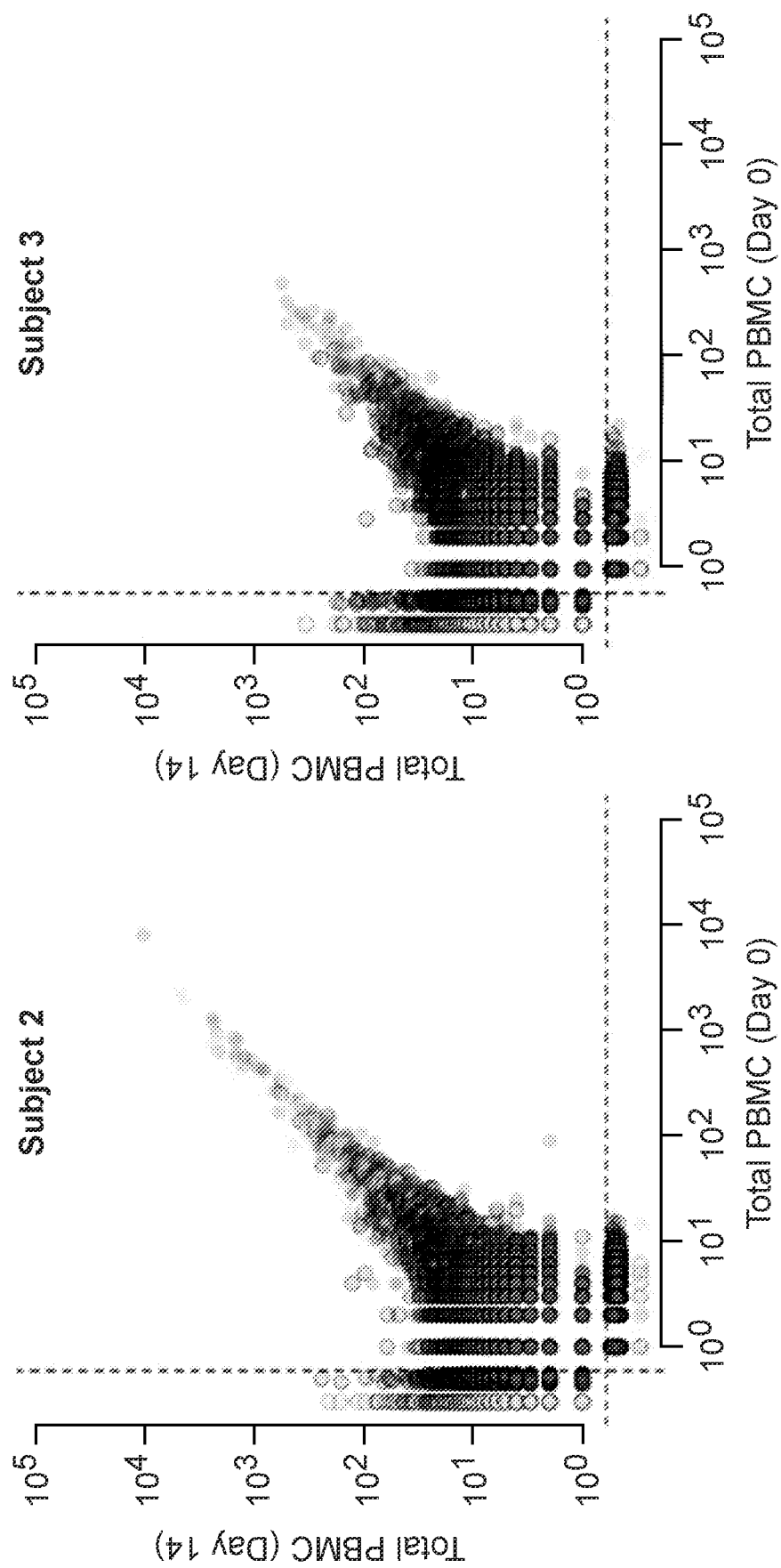
Figure 5D:
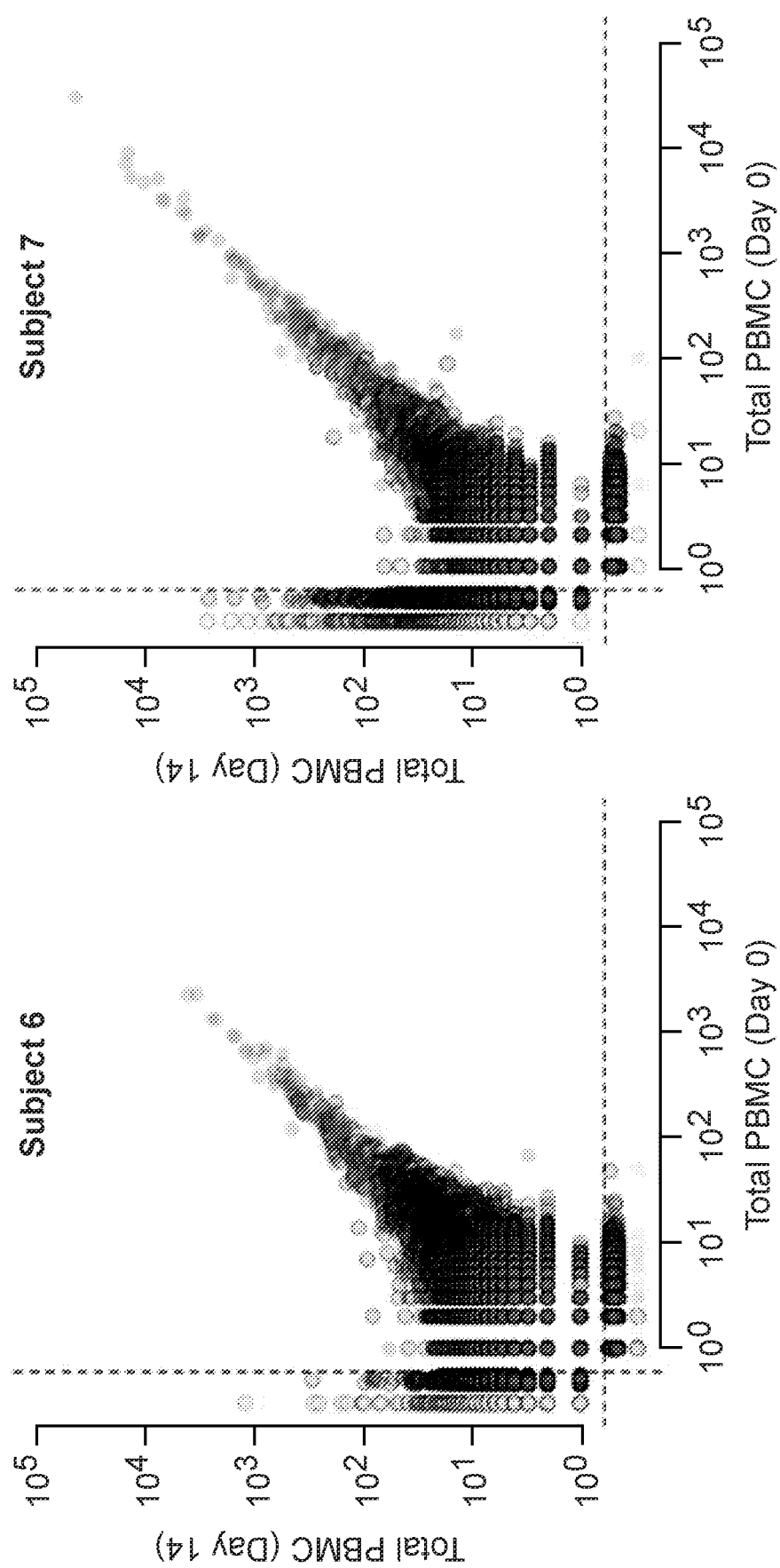
Figure 5E:
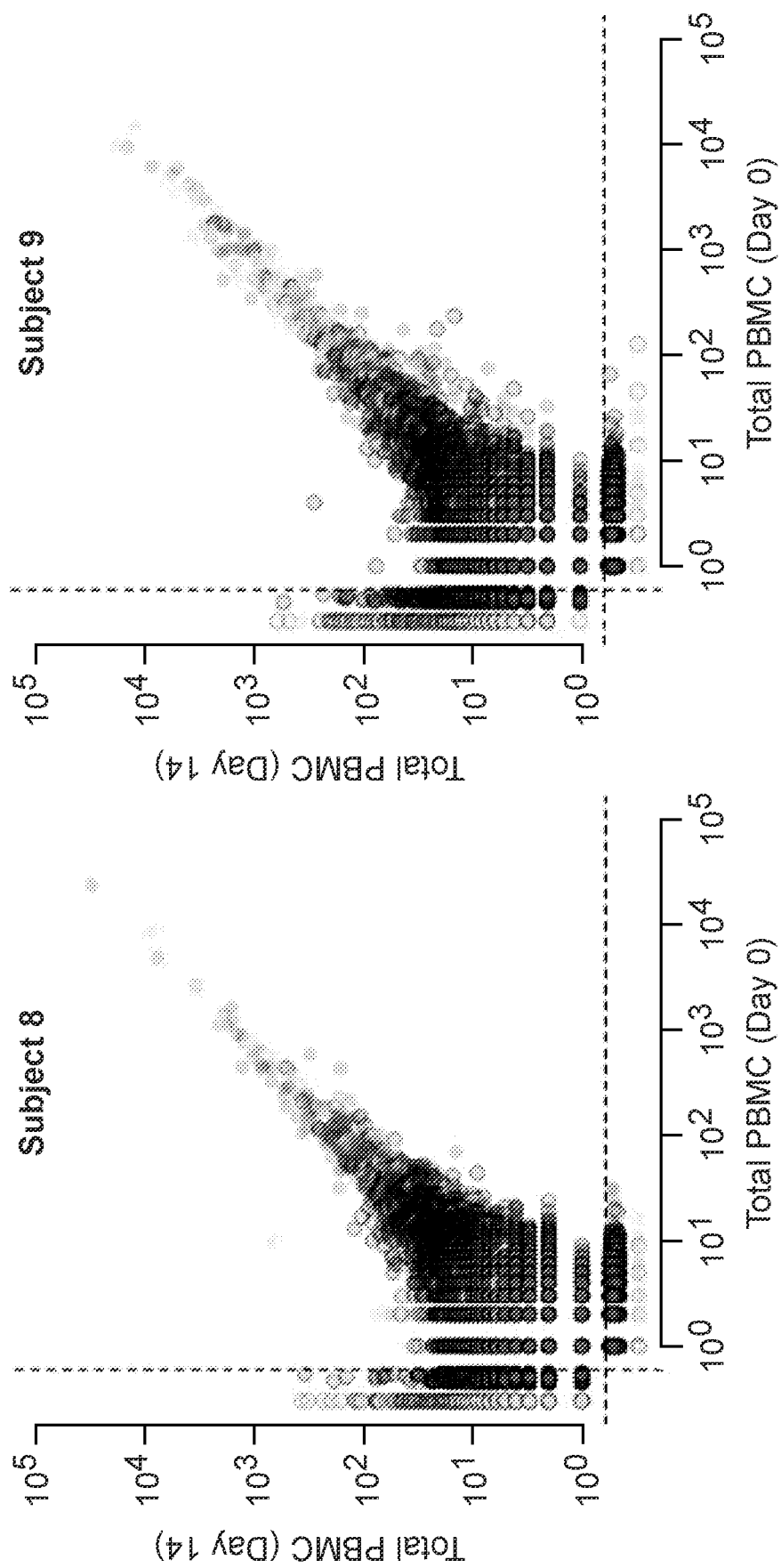

Identification of YFV putatively reactive clones. FIG. 5A shows the abundance of unique clones identified by statistical enrichment in the day 14 post-vaccination total PBMC sample compared to the pre-vaccination day 0 total PBMC sample from subject 1. Putatively reactive clones are enclosed by a circle in FIG. 5A. FIG. 5B shows the same for subjects 2 to 9. Significant enrichment (or expansion) was defined based on a q value threshold, with 1% and 5% expected false-positive rates for YFV-induced and putatively reactive clones, respectively, as described above. Clones were classified into four categories based both on their presence in the TAE-14 and the TM-0 compartments, as indicated in the legend. Darker colors indicate that multiple data points are superimposed in that particular position. Regions bound by dashed lines indicate clones present in only one sample.

Among all the cells present in the day 14 post-immunization sample, a set of clones that were highly expanded, but that were not captured by the antiviral-specific effector sort were identified (i.e., CD38+ HLA-DR+ CD8+ T cells). These clones could correspond to non-CD8+ T cells that express the TCRβ receptor (e.g., CD4+ T cells, NK T cells or γδ T cells), YF-induced CD8+ T cells that possess different surface markers than those previously reported by Miller et al. (2008, Immunity 28:710-722), or non-specific clonal expansions.

Example 4

Identifying Vaccine-Induced Activated T Cells without Enrichment

High-throughput sequencing was used to determine the contribution of all unique virus-specific clones to the long-lived memory T cell repertoire. In order to assess how well the expanded CD8+ T cell clones detected in the PBMC population using only immune repertoire sequencing (i.e., not sorted by flow-cytometry) concord with the previously identified activated effector CD38+ HLA-DR+ CD8+ T cell clones (i.e., those identified statistically after flow-cytometry sorting), it was determined how many expanded CD8+ T cells carrying productive rearrangements identified in the total PBMC sample analysis were classified as YFV-induced through the statistical analysis of flow-cytometry sorted CD38+ HLA-DR+ CD8+ T cell clones described above.

Table 6 (Appendix) shows the concordance between clones identified as putatively reactive in the total PBMC sample and YFV-induced clones identified by presence in the activated, effector CD8+ T cell compartment. Table 6 shows the counts and percentage of clones identified in the total PBMC sample that were also identified in the effector compartment as YFV-induced for each subject, and as a cumulative total.

A significant proportion of these putatively-reactive clones, between 25% and 95.2%, depending on the subject, are present in the CD38+ HLA-DR+ CD8+ T cell sort, suggesting they are induced by the YFV. In aggregate, 62% of the putatively-reactive clones identified as expanded in the d14 post-immunization total PBMC population (as compared to the equivalent population pre-immunization) can be classified as YFV-induced. The analysis demonstrates the potential of identifying vaccine-specific responding clones by identifying clones expanded in the total PBMC population exclusively using immune repertoire sequencing data.

As described herein, the dynamics of the effector and memory CD8+ T cell repertoires across three time points (pre-vaccination, 14 days post-vaccination, and 90 days post-vaccination) for volunteers who received the YF-17D vaccine were examined. Total PBMCs were isolated, and flow cytometry was used to sort a fraction of the samples into CD8+CD38+HLA-DR+ T cells on day 14 at the peak of their abundance, and into memory CD8+ T cells on days 0 and 90. High-throughput sequencing of the rearranged TCRβ locus allowed identification of CD8+ T cell clones in each sample, as well as estimated abundances for each clone. The synthesis of these sorting protocols with high-throughput sequencing enabled measurement of T cell response to infection at unprecedented resolution.

Importantly, it was shown that these YFV-induced CD8+ T cell clones can also be identified from peripheral blood, thus eliminating the need to select particular cellular populations through flow-cytometry.

Thus, it was determined that an average of approximately 2,000 different CD8+ T cell clonal lineages were activated by vaccination with YFV during the acute phase of the immune response, and that about 12% of them were detected in the long-term memory compartment (including both central and effector memory CD8+ T cells).

Using the methods described above, it can be determined if a similar number of CD8+ T cell clonal lineages are induced by other viral vaccines, or by naturally-occurring acute viral infections.

It was also observed that clones that were most expanded on the total PBMC sample from day 14 post-vaccination were more likely to enter the memory compartment 10 weeks later, in agreement with previous data (12). Although it was difficult to identify other defining characteristics that differentiate CD8+ T cell clones that expand in response to YFV vaccination and are present in the memory compartment on day 90 post-vaccination from those that wane during that period, additional studies can be performed to characterize these two populations further, including their epitope specificity, since this would constitute valuable information that could guide the design of vaccines against other pathogens. Interestingly, almost all of the clones that are markedly expanded in the total PBMC sample from day 14 post-vaccination (as compared to the corresponding day 0 pre-vaccination total PBMC sample from the same individual) were classified as YFV-induced CD8$^+$ T cells by the combination of flow cytometry and statistical analysis. In fact, very few clonally-expanded T cells in the periphery were observed that were not identified as YFV-induced clones, in agreement with previous reports showing that while CD8$^+$ T cells greatly expand in response to vaccination with YFV, the CD4$^+$ expansion is much less dramatic (6, 30, 32, 33). It is important to consider that the sampling depth used in this study limits the detection of bystander CD8$^+$ cells, or CD4$^+$ T cells that are only modestly expanded. Thus, the current level of detection is likely not sufficient to distinguish CD4$^+$ T cell expansion above the intrinsic system noise.

A particular pattern of V(D)J gene usage among the expanded CD8$^+$ T clone repertoire was not observed. This result partially agrees with a preliminary study of V gene usage performed by Co et al. (34), which used a limited set of anti-human Vβ antibodies. These authors did not observe a dominant Vβ family that predominated among the tetramer-specific CD8$^+$ T cells in two individuals vaccinated with YFV, but reported that although gene usage changed over time from the acute to the memory phase no particular V genes persisted between the acute and memory phases of the anti-viral response (34).

Finally, it is noteworthy that many of the CD8$^+$ T cell clones identified as expanded through the comparison of the day 14 post-vaccination and the day 0 pre-vaccination total PBMC samples were classified as likely YFV-specific in our initial characterization of clones enriched in the activated effector CD8$^+$ T cells vs. the total PBMC sample on day 14 post-vaccination. Thus, this approach is capable of identifying a fraction of the highly expanded CD8$^+$ T cells by immune repertoire sequencing of total PBMCs prior to infection or vaccination and during the acute response (i.e. 10-14 days post-vaccination), and could be used to ascertain the establishment of long-term memory by sorting memory T cells a few months after infection (or later) and tracking the CD8$^+$ T cells previously identified as being viral-induced. Additional experiments can be performed to address the epitope-specificity of the YFV-induced CD8$^+$ clones, using, for example, tetramer technology to purify clones that bind to previously identified immunodominant YFV epitopes.

Similar methods are applicable to the evaluation of the B cell response to vaccines and viral infections. In conclusion, immune repertoire sequencing methods, as described above, can be used to characterize the strength and breadth of the B and T cell response induced by vaccines and viral infections, and has the potential to be utilized to evaluate novel vaccines in terms of their potential ability to induce effective long-term protective immune responses.

APPENDIX

TABLE 1

| Cell population | Surface markers used for sorting | No. of subjects analyzed on: Day 0 | Day 14 | Day 90[b] |
|---|---|---|---|---|
| Total PBMCs | NA | 9 | 9 | |
| YFV-induced effector CD8$^+$ T cells | CD3$^+$ CD8$^+$ CD14$^-$ CD19$^-$ CD38$^+$ HLA-DR$^+$ | | 9 | |
| CD8$^+$ memory T cells ($T_{M\text{-}0}$) | CD3$^+$ CD8$^+$ CD14$^-$ CD19$^-$ CD45RA$^-$ CD45RO$^+$ | 9 | | |
| CD8$^+$ effector memory T cells ($T_{EM\text{-}90}$) | CD3$^+$ CD8$^+$ CD14$^-$ CD19$^-$ CD45RA$^-$ CD45RO$^+$ CD62L$^{lo}$ | | | 6 |
| CD8$^+$ central memory T cells ($T_{CM\text{-}90}$) | CD3$^+$ CD8$^+$ CD14$^-$ CD19$^-$ CD45RA$^-$ CD45RO$^+$ CD62L$^{hi}$ | | | 6 |

[a]Included are the cell populations studied, the surface markers used for sorting by flow cytometry, the days the samples were collected (day 0 prevaccination and days 14 and 90 postvaccination), and the number of subjects analyzed in each group. NA, not applicable.
[b]Day 90 samples from 3 subjects had to be discarded due to contamination.

TABLE 2

Number of YFV-induced clones separated by presence or absence in the memory compartment before immunization ($M_0$)
TABLE 2 Number of YFV-induced clones[a]

| Presence or absence in $T_{M\text{-}0}$ | No. of YFV-induced clones in subject no.: | | | | |
|---|---|---|---|---|---|
| | 1 | 2 | 3 | 4 | 5 |
| + | 139 | 241 | 36 | 139 | 426 |
| − | 2,303 | 2,126 | 3,804 | 2,010 | 1,618 |
| Total (% absent) | 2,442 (94.3) | 2,367 (89.8) | 3,840 (99.1) | 2,149 (93.5) | 2,044 (79.2) |

| Presence or absence in $T_{M\text{-}0}$ | No. of YFV-induced clones in subject no.: | | | | Avg | Total (%) |
|---|---|---|---|---|---|---|
| | 6 | 7 | 8 | 9 | | |
| + | 163 | 57 | 181 | 256 | 182 | 1,638 (8.5) |
| − | 1,764 | 1,538 | 1,653 | 757 | 1,953 | 17,573 (91.5) |
| Total (% absent) | 1,927 (91.5) | 1,595 (96.4) | 1,834 (90.1) | 1,013 (74.7) | 2,135 (91.5) | 21,346 (82.3) |

[a]For each subject, the table shows the number of YFV-inuced clones present (+) or absent (−) in the memory compartment on day 0 before vaccination ($T_{M\text{-}0}$), as well as the total number of YFV-induced clones identified and the percentage of those that were absent from $T_{M\text{-}0}$. The last two columns correspond to the aggregated dta (average, total, and percentage) from all 9 subjects.

TABLE 3

Number of YFV-induced clones absent on the $T_{M-0}$ compartment, classified based on their recruitment to the $T_{CM-90}$ and $T_{EM-90}$ compartments as well as the level of expansion, measured by their abundance on the day 14 post-vaccination total PBMC samples.

|  |  | Abundance |  |  |  |  |  |  |
|---|---|---|---|---|---|---|---|---|
|  |  | 1 | 2-3 | 4-7 | 8-15 | 16-31 | 32-63 | ≥64 |
| Subject 2 | CM⁻EM⁻ | 14 | 346 | 385 | 231 | 67 | 17 | 6 |
|  | CM⁺EM⁺ | 0 | 4 | 8 | 5 | 6 | 4 | 2 |
|  | CM⁻EM⁺ | 0 | 10 | 13 | 10 | 7 | 2 | 0 |
|  | CM⁺EM⁻ | 0 | 16 | 18 | 20 | 15 | 4 | 1 |
| Subject 4 | CM⁻EM⁻ | 7 | 328 | 304 | 190 | 53 | 11 | 2 |
|  | CM⁺EM⁺ | 0 | 6 | 8 | 6 | 10 | 8 | 8 |
|  | CM⁻EM⁺ | 0 | 4 | 16 | 14 | 5 | 3 | 0 |
|  | CM⁺EM⁻ | 0 | 16 | 24 | 18 | 3 | 2 | 1 |
| Subject 5 | CM⁻EM⁻ | 9 | 172 | 186 | 114 | 46 | 10 | 0 |
|  | CM⁺EM⁺ | 0 | 8 | 6 | 8 | 6 | 2 | 3 |
|  | CM⁻EM⁺ | 2 | 5 | 11 | 15 | 9 | 0 | 1 |
|  | CM⁺EM⁻ | 1 | 21 | 28 | 21 | 16 | 5 | 2 |
| Subject 7 | CM⁻EM⁻ | 1 | 131 | 168 | 274 | 277 | 99 | 76 |
|  | CM⁺EM⁺ | 0 | 0 | 0 | 3 | 8 | 1 | 14 |
|  | CM⁻EM⁺ | 0 | 0 | 2 | 4 | 9 | 6 | 8 |
|  | CM⁺EM⁻ | 0 | 3 | 10 | 18 | 51 | 31 | 27 |
| Subject 8 | CM⁻EM⁻ | 11 | 227 | 219 | 133 | 61 | 17 | 7 |
|  | CM⁺EM⁺ | 0 | 1 | 2 | 4 | 5 | 0 | 1 |
|  | CM⁻EM⁺ | 0 | 3 | 3 | 6 | 2 | 3 | 4 |
|  | CM⁺EM⁻ | 0 | 9 | 8 | 13 | 8 | 6 | 5 |
| Subject 9 | CM⁻EM⁻ | 1 | 74 | 98 | 88 | 42 | 28 | 11 |
|  | CM⁺EM⁺ | 0 | 1 | 2 | 4 | 2 | 8 | 11 |
|  | CM⁻EM⁺ | 0 | 1 | 3 | 6 | 5 | 5 | 8 |
|  | CM⁺EM⁻ | 0 | 4 | 9 | 9 | 14 | 9 | 10 |

TABLE 4

Composition of the day 90 memory compartment. Shown are the number of new, YFV-induced clones contributing to the TEM-90 and TCM-90 memory compartments as compared to the non-YFV-induced clones, counted both by number of clones and by number of templates.

|  |  | clone counts |  | template counts |  |
|---|---|---|---|---|---|
|  |  | new YFV-induced | not YFV-induced | new YFV-induced | not YFV-induced |
| Subject 2 | EM | 96 | 34,584 | 668 | 173,024 |
|  | CM | 144 | 39,683 | 245 | 119,443 |
| Subject 4 | EM | 124 | 20,309 | 431 | 159,933 |
|  | CM | 151 | 37,911 | 321 | 148,867 |
| Subject 5 | EM | 139 | 30,260 | 327 | 132,558 |
|  | CM | 225 | 51,247 | 769 | 136,699 |
| Subject 7 | EM | 66 | 27,295 | 117 | 171,953 |
|  | CM | 184 | 33,914 | 375 | 102,844 |
| Subject 8 | EM | 51 | 11,485 | 135 | 104,340 |
|  | CM | 95 | 18,658 | 563 | 131,258 |
| Subject 9 | EM | 68 | 14,163 | 2818 | 119,083 |
|  | CM | 92 | 27,776 | 251 | 93,823 |

TABLE 5

Number of YFV-induced clones newly recruited to the TCM-90 and TEM-90 memory compartments

|  | Subject |  |  |  |  |  |  |  |
|---|---|---|---|---|---|---|---|---|
|  | 2 | 4 | 5 | 7 | 8 | 9 | Total | % |
| CM⁺EM⁺ | 37 | 59 | 63 | 33 | 19 | 29 | 240 | 2.5% |
| CM⁺EM⁻ | 59 | 65 | 76 | 33 | 32 | 39 | 304 | 3.1% |
| CM⁻EM⁺ | 107 | 92 | 162 | 151 | 76 | 63 | 651 | 6.7% |
| CM⁻EM⁻ | 1,923 | 1,794 | 1,317 | 1,321 | 1,526 | 626 | 8507 | 87.7% |
| Total | 2,126 | 2,010 | 1,618 | 1,321 | 1,653 | 757 | 9702 |  |

For each subject, the table shows the number of YFV-induced clones newly recruited to the TCM-90 and TEM-90 memory compartments (CM+EM+), the TCM-90 only (CM+EM−), the TEM-90 only (CM−EM+.) or neither (CM−EM−), as well as the total number of clones. The last two columns correspond to the aggregated data (total and percentage) from the 6 subjects for whom the memory populations were studied.

TABLE 6

Concordance between identified as "putatively reactive" in the total PBMC sample and YFV-induced clones identified by their presence in the activated effector CD8+ T cell compartment.

| Presence or absence in $T_{AE-14}$ compartment | No. of "putatively reactive" clonse in subject no.: |  |  |  |  |  |
|---|---|---|---|---|---|---|
|  | 1 | 2 | 3 | 4 | 5 | 6 |
| + | 127 | 39 | 118 | 36 | 3 | 44 |
| − | 106 | 20 | 6 | 3 | 9 | 56 |
| Total (% present in $T_{AE-14}$) | 233 (54.5) | 59 (66.1) | 124 (95.2) | 39 (92.3) | 12 (25.0) | 100 (44.0) |

TABLE 6-continued

Concordance between identified as "putatively reactive"
in the total PBMC sample and YFV-induced clones identified by
their presence in the activated effector CD8+ T cell compartment.

| Presence or absence in $T_{AE-14}$ compartment | 7 | 8 | 9 | Avg | Total (%) |
|---|---|---|---|---|---|
| + | 288 | 74 | 119 | 94.2 | 848 (62.2) |
| − | 190 | 38 | 87 | 57.2 | 515 (37.8) |
| Total (% present in $T_{AE-14}$) | 478 (60.3) | 112 (66.1) | 206 (57.8) | 151.4 (62.4) | 1,363 (62.2) |

For each subject, Table 6 shows the number of "putatively reactive" clones identified in the total PBMC sample that were present (+) or absent (−) in the corresponding $T_{AE-14}$. The last two columns correspond to the aggregated data (average, total, percentage) from all 9 subjects.

REFERENCES

1. Kaech S M, Wherry E J. 2007. Heterogeneity and cell-fate decisions in effector and memory CD8+ T cell differentiation during viral infection. Immunity 27:393-405.
2. Wherry E J, Ha S J, Kaech S M, Raining W N, Sarkar S, Kalia V, Subramaniam S, Blattman J N, Barber D L, Ahmed R. 2007. Molecular signature of CD8+ T cell exhaustion during chronic viral infection. Immunity 27:670-684. http://dx.doi.org/10.1016/j.immuni.2007.09.006.
3. Engel I, Hedrick S M. 1988. Site-directed mutations in the VDJ junctional region of a T cell receptor beta chain cause changes in antigenic peptide recognition. Cell 54:473-484.
4. Jorgensen J L, Esser U, Fazekas de St Groth B, Reay P A, Davis M M. 1992. Mapping T- cell receptor-peptide contacts by variant peptide immunization of single-chain transgenics. Nature 355:224-230.
5. McHeyzer-Williams M G, Davis M M. 1995. Antigen-specific development of primary and memory T cells in vivo. Science 268:106-111.
6. Miller J D, van der Most R G, Akondy R S, Glidewell J T, Albott S, Masopust D, Murali-Krishna K, Mahar P L, Edupuganti S, Lalor S, Germon S, Del Rio C, Mulligan M J, Staprans S I, Altman J D, Feinberg M B, Ahmed R. 2008. Human effector and memory CD8+ T cell responses to smallpox and yellow fever vaccines. Immunity 28:710-722.
7. Newell E W, Sigal N, Bendall S C, Nolan G P, Davis M M. 2012. Cytometry by time-of-flight shows combinatorial cytokine expression and virus specific cell niches within a continuum of CD8+ T cell phenotypes. Immunity 36:142-152.
8. Precopio M L, Betts M R, Parrino J, Price D A, Gostick E, Ambrozak D R, Asher T E, Douek D C, Harari A, Pantaleo G, Bailer R, Graham B S, Roederer M, Koup R A. 2007. Immunization with vaccinia virus induces polyfunctional and phenotypically distinctive CD8(+) T cell responses. J Exp Med 204:1405-1416.
9. Akondy R S, Monson N D, Miller J D, Edupuganti S, Teuwen D, Wu H, Quyyumi F, Garg S, Altman J D, Del Rio C, Keyserling H L, Ploss A, Rice C M, Orenstein W A, Mulligan M J, Ahmed R. 2009. The yellow fever virus vaccine induces a broad and polyfunctional human memory CD8+ T cell response. J Immunol 183:7919-7930.
10. Co M D, Terajima M, Cruz J, Ennis F A, Rothman A L. 2002. Human cytotoxic T lymphocyte responses to live attenuated 17D yellow fever vaccine: identification of HLA-B35-restricted CTL epitopes on nonstructural proteins NSI, NS2b, NS3, and the structural protein E. Virology 293:151-163.
11. Turner S J, Diaz G, Cross R, Doherty P C. 2003. Analysis of clonotype distribution and persistence for an influenza virus-specific CD8+ T cell response. Immunity 18:549-559.
12. Blom K, Braun M, lvarsson MA, Gonzalez V D, Falconer K, Moll M, Ljunggren H G, Michaelsson J, Sandberg J K. 2013. Temporal dynamics of the primary human T cell response to yellow fever virus 17D as it matures from an effector- to a memory-type response. J Immunol 190:2150-2158.
13. Manuel E R, Charini W A, Sen P, Peyerl F W, Kuroda M J, Schmitz J E, Autissier P, Sheeter D A, Torbett B E, Letvin N L. 2006. Contribution of T-cell receptor repertoire breadth to the dominance of epitope-specific CD8+ T-lymphocyte responses. J Virol 80:12032-12040.
14. Miconnet 1, Marrau A, Farina A, Taffe P, Vigano S, Harari A, Pantaleo G. 2011. Large TCR diversity of virus-specific CD8 T cells provides the mechanistic basis for massive TCR renewal after antigen exposure. J Immunol 186:7039-7049.
15. Henrickson S E, Perro M, Loughhead S M, Senman B, Stutte S, Quigley M, Alexe G, lannacone M, Flynn M P, Omid S, Jesneck J L, Imam S, Mempel T R, Mazo I B, Raining W N, von Andrian U H. 2013. Antigen availability determines CD8(+) T cell-dendritic cell interaction kinetics and memory fate decisions. Immunity 39:496-507.
16. Ahmed R, Akondy R S. 2011. Insights into human CD8(+) T-cell memory using the yellow fever and smallpox vaccines. Immunol Cell Biot 89: 340-345.
17. Achour A, Michaelsson J, Harris R A, Odeberg J, Grufman P, Sandberg J K, Levitsky V, Karre K, Sandalova T, Schneider G. 2002. A structural basis for LCMV immune evasion: subversion of H-2Db and H-2Kb presentation of gp33 revealed by comparative crystal structure analyses. Immunity 17:757-768.
18. Eckle S B, Turner S J, Rossjohn J, McCluskey J. 2013. Predisposed a T cell antigen receptor recognition of MHC and MHC-1 like molecules? Curr Opin Immunol 25:653-659.
19. Hou S, Hyland L, Ryan K W, Portner A, Doherty P C. 1994. Virus specific CD8+ T-cell memory determined by clonal burst size. Nature 369:652-654.
20. Vezys V, Yates A, Casey K A, Lanier G, Ahmed R, Antia R, Masopust D. 2009. Memory CD8 T-cell compartment grows in size with immunological experience. Nature 457:196-199.

21. Badovinac V P, Porter B B, Harty J T. 2002. Programmed contraction of CD8(+) T cells after infection. Nat Immunol 3:619-626.
22. Sung J H, Zhang H, Moseman E A, Alvarez D, Iannacone M, Henrickson S E, de la Torre J C, Groom J R, Luster A D, von Andrian U H. 2012. Chemokine guidance of central memory T cells is critical for antiviral recall responses in lymph nodes. Cell 150:1249-1263.
23. Flynn K J, Betz G T, Altman J D, Ahmed R, Woodland D L, Doherty P C. 1998. Virus-specific CD8+ T cells in primary and secondary influenza pneumonia. Immunity 8:683-691.
24. Sourdive D J, Murali-Krishna K, Altman J D, Zajac A J, Whitmire J K, Pannetier C, Kourilsky P, Evavold B, Sette A, Ahmed R. 1998. Conserved T cell receptor repertoire in primary and memory CD8 T cell responses to an acute viral infection. J Exp Med 188:71-82.
25. Lee E, Lobigs M. 2008. E protein domain III determinants of yellow fever virus 17D vaccine strain enhance binding to glycosaminoglycans, impede virus spread, and attenuate virulence. J Virol 82:6024-6033.
26. SanofiPasteur. YF-VAX prospectus. Document LE6445-LE6446. SanofiPasteur, Rockville, Md.
27. Pulendran B. 2009. Learning immunology from the yellow fever vaccine: innate immunity to systems vaccinology. Nat Rev Immunol 9:741-747.
28. Querec T, Bennouna S, Alkan S, Laouar Y, Gorden K, Flavell R, Akira S, Ahmed R, Pulendran B. 2006. Yellow fever vaccine YF-17D activates multiple dendritic cell subsets via TLR2, 7, 8, and 9 to stimulate polyvalent immunity. J Exp Med 203:413-424.
29. Jonker E F, Visser L G, Roukens A H. 2013. Advances and controversies in yellow fever vaccination. Ther Adv Vaccines 1:144-152.
30. Reinhardt B, Jaspert R, Niedrig M, Kostner C, L'Age-Stehr J. 1998. Development of viremia and humoral and cellular parameters of immune activation after vaccination with yellow fever virus strain 17D: a model of human flavivirus infection. J Med Virol 56:159-167.
31. Santos A P, Bertho A L, Dias D C, Santos J R, Marcovistz R. 2005. Lymphocyte subset analyses in healthy adults vaccinated with yellow fever 17DD virus. Mem Inst Oswaldo Cruz 100:331-337.
32. Kohler S, Bethke N, Bothe M, Sommerick S, Frentsch M, Romagnani C, Niedrig M, Thiel A. 2012. The early cellular signatures of protective immunity induced by live viral vaccination. Eur J Immunol 42:2363-2373.
33. James E A, LaFond R E, Gates T J, Mai D T, Malhotra U, Kwok W W. 2013. Yellow fever vaccination elicits broad functional CD4+ T cell responses that recognize structural andnonstructural proteins. J Virol 87:12794-12804.
34. Co M D, Kilpatrick E D, Rothman A L. 2009. Dynamics of the CD8 T-cell response following yellow fever virus 17D immunization. Immunology 128:e718-e727.
35. Robins H S, Campregher P V, Srivastava S K, Wacher A, Turtle C J, Kahsai 0, Riddell S R, Warren E H, Carlson C S. 2009. Comprehensive assessment of T-cell receptor beta-chain diversity in a T cells. Blood 114:4099-4107.
36. Lefranc M P, Giudicelli V, Duroux P, Jabado-Michaloud J, Folch G, Aouinti S, Carillon E, Duvergey H, Houles A, Paysan-Lafosse T, Hadi- Saljoqi S, Sasorith S, Lefranc G, Kossida S. 2015. IMGT, the international ImMunoGeneTics information system 25 years on. Nucleic Acids Res 43:D413-D422.
37. Yousfi Monod M, Giudicelli V, Chaume D, Lefranc M P. 2004. IMGT/Junction Analysis: the first tool for the analysis of the immunoglobulin and T cell receptor complex V-J and V-D-J junctions. Bioinformatics (Oxford) 20(Suppl 1):i379-i385.
38. Wu D, Emerson R O, Sherwood A, Loh M L, Angiolillo A, Howie B, Vogt J, Rieder M, Kirsch I, Carlson C, Williamson D, Wood B L, Robins H. 2014. Detection of minimal residual disease in B lymphoblastic leukemia by high-throughput sequencing of IGH. Clin Cancer Res 20:4540-4548.
39. Pulendran B, Ahmed R. 2011. Immunological mechanisms of vaccination. Nat Immunol 12:509-517.
40. Murali-Krishna K, Altman J D, Suresh M, Sourdive D J, Zajac A J, Miller J D, Slansky J, Ahmed R. 1998. Counting antigen-specific CD8 T cells: a reevaluation of bystander activation during viral infection. Immunity 8:177-187.
41. Hamann D, Baars P A, Rep M H, Hooibrink B, Kerkhof-Garde S R, Klein M R, van Lier R A. 1997. Phenotypic and functional separation of memory and effector human CD8+ T cells. J Exp Med 186:1407-1418.
42. Sallusto F, Lenig D, Forster R, Lipp M, Lanzavecchia A. 1999. Two subsets of memory T lymphocytes with distinct homing potentials and effector functions. Nature 401:708-712.

What is claimed:

1. A method of measuring T cell response to a vaccine in a subject, comprising:
performing high-throughput sequencing of nucleic acid molecules comprising rearranged CDR3 regions of TCR loci obtained from a first biological sample of the subject at a first time point post vaccination, wherein the first biological sample is obtained at least 10 days post vaccination;
sorting activated T cells from a subset of the first biological sample using flow cytometry to generate a set of activated T cells;
performing high-throughput sequencing of nucleic acid molecules comprising rearranged CDR3 regions of TCR loci obtained from the set of activated T cells; and
identifying activated T cell clones in the set having CDR3 regions of significantly higher proportional abundance in the activated T cell population in comparison to the first biological sample, thereby identifying vaccine-induced responsive clones.

2. The method of claim 1, wherein the TCR loci are selected from the group consisting of the TCRα locus, TCRβ locus, TCRγ locus, and TCRδ locus.

3. The method of claim 1, wherein the biological samples comprise peripheral blood mononuclear cells (PBMCs).

4. The method of claim 1, wherein the biological samples comprise memory T cells.

5. The method of claim 1, further comprising performing multiplex PCR amplification of genomic templates comprising rearranged CDR3 regions to produce nucleic acid molecules for sequencing.

6. The method of claim 1, wherein identifying comprises calculating a false discovery rate, and wherein the calculating comprises performing a computation on a computer.

7. The method of claim 1, wherein the activated T cell clones are vaccine antigen-specific T cells.

8. The method of claim 1, wherein the activated T cell clones are $CD8^+$ effector T cells.

9. The method of claim 1, wherein the vaccine is a vaccine for an infectious agent or a cancer vaccine.

10. The method of claim 1, further comprising:
performing high-throughput sequencing of nucleic acid molecules comprising rearranged CDR3 regions of TCR loci obtained from a second biological sample of the subject at a second time point post vaccination; and identifying newly recruited memory T cell clones corresponding to the vaccine-induced responsive clones that have been recruited to a memory T cell population post vaccination.

11. The method of claim 10, wherein the identifying newly recruited memory T cell clones comprises sorting memory T cells by flow cytometry.

12. The method of claim 10, wherein identifying newly recruited memory T cell clones comprises comparing a first set of memory T cell clones in the first biological sample to a second set of memory T cell clones in the second biological sample to identify one or more newly recruited memory T cell clones that have been recruited to the memory T cell population post vaccination.

13. The method of claim 12, further comprising comparing the identified one or more newly recruited memory T cell clones with one or more vaccine-induced responsive clones from the set of activated T cells to find matches between the newly recruited memory T cell clones and the one or more vaccine-induced responsive clones.

14. The method of claim 13, wherein the matched memory T cell clones are a significant number of the vaccine-induced responsive clones and are identified as biomarkers for vaccine-specific response.

15. The method of claim 13, wherein the matched memory T cell clones are a significant proportion of total memory T cell population and are identified as biomarkers for vaccine-specific response.

16. The method of claim 10, wherein the memory T cell clones are $CD8^+CD45RO^+CD62L^{lo}$ effector memory T cells.

17. The method of claim 10, wherein the memory T cell clones are $CD8^+CD45RO^+CD62L^{hi}$ central memory T cells.

18. The method of claim 10, wherein the second time point is at least 30 days post vaccination.

19. A method of measuring a T cell response to an infection in a subject, comprising:

performing high-throughput sequencing of nucleic acid molecules comprising rearranged CDR3 regions of TCR loci obtained from a first biological sample of the subject at a first time point post infection, wherein the infection is selected from the group consisting of viral infection, bacterial infection, and parasitic infection;

sorting activated T cells from a subset of the first biological sample using flow cytometry to generate a set of activated T cells;

performing high-throughput sequencing of nucleic acid molecules comprising rearranged CDR3 regions of TCR loci obtained from the set of activated T cells; and identifying activated T cell clones in the set having CDR3 regions of significantly higher proportional abundance in the activated T cell population in comparison to the first biological sample, thereby identifying infection-induced responsive clones.

20. The method of claim 19, further comprising:

performing high-throughput sequencing of nucleic acid molecules comprising rearranged CDR3 regions of TCR loci obtained from a second biological sample of the subject at a second time point post infection; and identifying newly recruited memory T cell clones corresponding to the infection-induced responsive clones that are not present in the first biological sample and that have been recruited to a memory T cell population post infection.

21. The method of claim 20, wherein identifying newly recruited memory T cell clones comprises comparing a first set of memory T cell clones in the first biological sample to a second set of memory T cell clones in the second biological sample to identify one or more newly recruited memory T cell clones that have been recruited to the memory T cell population post infection.

22. The method of claim 19, wherein the viral infection is an acute viral infection.

* * * * *